US009662348B2

(12) United States Patent
Sela et al.

(10) Patent No.: US 9,662,348 B2
(45) **Date of Patent: *May 30, 2017**

(54) **COMPOSITIONS FOR CONTROLLING *VARROA* MITES IN BEES**

(71) Applicants: Yissum Research Development Company of the Hebrew University of Jerusalem Ltd., Jerusalem (IL); Beeologics Inc., St. Louis, MO (US)

(72) Inventors: Ilan Sela, Ramot-HaShavim (IL); Sharoni Shafir, Nes Ziona (IL); Eyal Maori, Rishon-LeZion (IL); Yael Garbian, Rishon-LeZion (IL); Eyal Ben-Chanoch, Miami, FL (US); Gal Yarden, Nir-Moshe (IL); Haim Kalev, Kfar-HaNagid (IL)

(73) Assignees: Yissum Research Development Company of the Hebrew University of Jerusalem Ltd., Jerusalem (IL); Beeologics Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/606,328

(22) Filed: Jan. 27, 2015

(65) Prior Publication Data

US 2015/0133532 A1 May 14, 2015

Related U.S. Application Data

(63) Continuation of application No. 13/446,557, filed on Apr. 13, 2012, now Pat. No. 8,962,584, which is a continuation-in-part of application No. PCT/IL2010/000844, filed on Oct. 14, 2010.

(60) Provisional application No. 61/251,339, filed on Oct. 14, 2009.

(51) Int. Cl.
*C12N 15/11* (2006.01)
*A61K 31/713* (2006.01)
*C12N 15/113* (2010.01)

(52) U.S. Cl.
CPC .......... *A61K 31/713* (2013.01); *C12N 15/113* (2013.01); *C12N 15/1137* (2013.01); *C12N 2310/11* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 4,732,250 | A | 3/1988 | Maucher et al. |
| 5,898,031 | A | 4/1999 | Crooke |
| 6,107,094 | A | 8/2000 | Crooke |
| 6,506,559 | B1 | 1/2003 | Fire et al. |
| 7,056,704 | B2 | 6/2006 | Tuschl et al. |
| 7,078,196 | B2 | 7/2006 | Tuschl et al. |
| 8,097,712 | B2 | 1/2012 | Paldi et al. |
| 8,507,457 | B2 | 8/2013 | Paldi et al. |
| 2002/0086356 | A1 | 7/2002 | Tuschl et al. |
| 2003/0044443 | A1 | 3/2003 | Erickson et al. |
| 2003/0092651 | A1 | 5/2003 | Norris et al. |
| 2003/0180945 | A1 | 9/2003 | Wang et al. |
| 2004/0259247 | A1 | 12/2004 | Tuschl et al. |
| 2005/0080032 | A1 | 4/2005 | Gross et al. |
| 2005/0095199 | A1 | 5/2005 | Whyard et al. |
| 2007/0011448 | A1 | 1/2007 | Chhabra et al. |
| 2007/0219151 | A1 | 9/2007 | Satishchandran et al. |
| 2007/0232188 | A1 | 10/2007 | Probasco |
| 2008/0194512 | A1 | 8/2008 | John et al. |
| 2008/0261303 | A1 | 10/2008 | Kreutzer et al. |
| 2009/0118214 | A1 | 5/2009 | Paldi et al. |
| 2012/0053231 | A1 | 3/2012 | Paldi et al. |
| 2012/0108497 | A1 | 5/2012 | Paldi et al. |
| 2012/0258646 | A1 | 10/2012 | Sela et al. |
| 2013/0289097 | A1 | 10/2013 | Paldi et al. |

FOREIGN PATENT DOCUMENTS

| | | | | |
|---|---|---|---|---|
| AU | 2008325989 | A1 | 5/2009 | |
| CN | 1505504 | A | 6/2004 | |
| CN | 101139607 | A | 3/2008 | |
| EP | 1416049 | A1 | 5/2004 | |
| EP | 2703489 | A1 | 3/2014 | |
| EP | 2703490 | A1 | 3/2014 | |
| EP | 2706114 | A1 | 3/2014 | |
| KR | WO 2007074976 | A1 * | 7/2007 | .......... A23K 1/1612 |
| WO | 97/47193 | A1 | 12/1997 | |
| WO | 99/32619 | A1 | 7/1999 | |
| WO | 00/04176 | A1 | 1/2000 | |
| WO | 01/34815 | A1 | 5/2001 | |
| WO | 2009/060429 | A2 | 5/2009 | |
| WO | 2010/128465 | A1 | 11/2010 | |

(Continued)

OTHER PUBLICATIONS

Taylor et al. "Validation of Spermidine Synthase as a Drug Target in African Trypanosomes", Biochemical Journal, 409 (2): 563-569, Jan. 15, 2008.
Translation Dated Feb. 9, 2015 of Office Action Dated Jan. 26, 2015 From the Israel Patent Office Re. Application No. 219193.
Translation Dated Jan. 15, 2015 of Office Action Dated Dec. 18, 2014 From the Israel Patent Office Re. Application No. 216154.
Translation Dated Jan. 20, 2015 of Office Action Dated Dec. 31, 2014 From the Israel Patent Office Re. Application No. 205594.

(Continued)

*Primary Examiner* — Kate Poliakova-Georgantas
(74) *Attorney, Agent, or Firm* — Arnold & Porter Kaye Scholer LLP

(57) ABSTRACT

An isolated nucleic acid agent is disclosed comprising a nucleic acid sequence which downregulates expression of a gene product of a *Varroa destructor* mite. Compositions comprising same and uses thereof are also disclosed.

18 Claims, 11 Drawing Sheets

(56) References Cited

FOREIGN PATENT DOCUMENTS

| | | | |
|---|---|---|---|
| WO | 2011/045796 | A1 | 4/2011 |
| WO | 2013153553 | A2 | 10/2013 |

OTHER PUBLICATIONS

Translation of CN Office Action dated Jul. 2, 2013 from the State Intellectual Property Office of the People's Republic of China re Application No. 201080056585.9.
Translation of Search Report dated Jul. 2, 2013 from the State Intellectual Property Office of the People's Republic of China re Application No. 201080056585.9.
Tsaousis et al. "A Novel Route for ATP Acquisition by the Remnant Mitochondria of Encephalitozoon Cuniculi", Nature, 453(7194): May 22, 2008. Abstract.
Ullu et al. "RNA Interference in Protozoan Parasites", Cellular Microbiology, 6(6): 509-519, 2004.
Van Engelsdorp "Colony Collapse Disorder: A Descriptive Study", PLoS One, 4(8): e6481: 1-17, 2009.
Wang et al. "Molecular Characterization of an Arachnid Sodium Channel Gene From the Varroa Mite (*Varroa destructor*)", Insect Biochemistry and Molecular Biology, XP002621492, 33(7): 733-739, Jul. 2003. Abstract.
Whitfield et al., "BB170006B20C05.5 Bee Brain Normalized/Subtracted Library, BB17 Apis Mellifera cDNA Clone BB170006B20C05 5', mRNA Sequence", Database EMBL [Online], XP002719131, Retrieved IBIS, Database Accession No. BI503250, Aug. 30, 2001.
Williams "Unique Physiology of Host-Parasite Interactions in Microsporidia Infections", Cellular Microbiology, XP002589428, 11(11): 1551-1560, Nov. 2009.
Williams et al. "Genome Sequence Surveys of Brachiola Algerae and Edhazardia Aedis Reveal Micriosporidia With Low Gene Densities", BMC Genomics, 9(200): 1-9, Apr. 29, 2008.
Written Opinion Dated Aug. 13, 2009 From the International Searching Authority Re.: Application No. PCT/IL2008/001440.
Yadav et al. "Host-Generated Double Stranded RNA Induces RNAi in Plant-Parasitic Nematodes and Protects the Host From Infection", Molecular & Biochemical Parasitology, 148: 219-222, 2006.
Zhou et al., "The Effects of Brood Comb Cell Size on the Reproductive Behavior of the Ectoparasitic Mite *Varroa destructor* on Honey Bees", Chinese Journal of Entomology, 2006, pp. 89-93, vol. 43, No. 1.
International Search Report Dated Aug. 13, 2009 From the International Searching Authority Re.: Application No. PCT/IL2008/001440.
Katinka et al. "Genome Sequence and Gene Compaction of the Eukaryote Parasite Encephalitozoon Cuniculi", Nature, 414(6862): 450-453, Nov. 22, 2001. Abstract.
Liu et al. "Effect of a Fluvalinate-Resistance-Associated Sodium Chennel Mutation From Varroa Mites on Cockroach Sodium Channel Sensitivity to Fluvalinate, A Pyrethroid Insecticide", Insect Biochemistry and Molecular Biology, XP025014535, 36(11): 885-889, Nov. 1, 2006. Abstract.
Liu et al. "Prevention of Chinese Sacbrood Virus Infection in Apis Cerana Using RNA Interference", Current Microbiology, 61(5): 422-428, Nov. 2010. Abstract.
Maggi et al. "Resistance Phenomena to Amitraz From Population of the Ectoparasitic Mite *Varroa destructor* of Argentina", Parasitology Research, 107(5): 1189-1192, Oct. 2010. Abstract.
Malhotra et al. "Double-Stranded RNA-Mediated Gene Silencing of Cysteine Proteases (Falcipain-1 and -2) of Plasmodium Falciparum", Molecular Microbiology, 45(5): 1245-1254, 2002.
Malone et al. "Effects of Transgene Products on Honey Bees (*Apis mellifera*) and Bumblebees (*bombus* Sp.)", Apidologie, XP009141014, 32(4): 287-304, Jul. 2001. p. 288, col. 1-h, § 3—p. 289, col. 1-h, § 2.
Maori et al. "IAPV, A Bee-Affecting Virus Associated With Colony Collapse Disorder Can Be Silenced by DsRNA Ingestion", Insect Molecular Biology, XP002523701, 18(1): 55-60, Feb. 2009. Abstract.
Maori et al. "Isolation and Characterization of Israeli Acute Paralysis Virus, A Dicistrovirus Affecting Honeybees in Israel: Evidence for Diversity Due to Intra•and Inter-Species Recombination", Journal of General Virology, XP002533679, 88(Part 12): 3428-3438, Dec. 2007. Database EMBL [Online], Retrieved From EBI, Database Accession No. EF219380, Nov. 21, 2007.
Maori et al. "Israel Acute Paralysis Virus of Bees, Complete Genome", GenBank EMBL, EBI Dbfetch, XP002533679, Accession No. EF219380, Nov. 21, 2007.
Maori et al. "Reciprocal Sequence Exchange Between Non-Retro Viruses and Hosts Leading to the Appearance of New Host Phenotypes", Virology, XP022065066, 362(2): 342-349, 2007.
Mayack et al. "Energetic Stress in the Honeybee *Apis mellifera* From Nosema Ceranae Infection", Journal of Invertebrate Pathology, 100(3): 185-188, Mar. 2009.
Mutti et al. "IRS and TOR Nutrient-Signaling Pathways Act Via Juvenile Hormone to Influence Honey Bee Caste Fate", Journal of Experimental Biology, 214(Pt.23): 3977-3984, Dec. 1, 2011. Abstract.
Nakayashiki et al. "Evolution and Diversification of RNA Silencing Proteins in Fungi", Journal of Molecular Evolution, 63(1): 127-135, Jul. 2006.
Nielsen et al, "Sacbrood Virus Isolate T73/05A Polyprotein Gene, Partial CDs", Database EMBL [Online], XP002719130, Retrieved From IBIS, Database Accession No. EF570887, May 12, 2007.
Nunes et al. "A Non-Invasive Method for Silencing Gene Transcription in Honeybees Maintained Under Natural Conditions", Insect Biochemistry and Molecular Biology, XP002523702, 39(2): 157-160, Feb. 1, 2009.
O'Riordan et al., "Inhibitor of Apoptosis (IAP) Proteins in Eukaryotic Evolution and Development: A Model of Thematic Conservation", Developmental Cell, Oct. 2008, pp. 497-508, vol. 15 No. 4.
Office Action (restriction) for U.S. Appl. No. 13/318,636 dated Nov. 21, 2012.
Office Action CN Application 201080056585.9 dated Nov. 25, 2014.
Office Action Dated May 12, 2014 From the State Intellectual Property Office of the People's Republic of China Re. Application No. 201080056585.9 and its Translation Into English.
Office Action Dated Jan. 19, 2014 From the Israel Patent Office Re. Application No. 205594 and its Translation Into English.
Office Action Dated Mar. 19, 2012 From the Israel Patent Office Re. Application No. 205594 and its Translation Into English.
Office Action Dated Jan. 26, 2015 From the Israel Patent Office Re. Application No. 219193.
Office Action Dated Dec. 31, 2014 From the Israel Patent Office Re. Application No. 205594.
Office Action for EP Application 10779855.5 dated Nov. 10, 2014.
Office Action for EP Application 13156180.5 dated Sep. 29, 2014.
Office Action for EP Application 13156185.4 dated Sep. 29, 2014.
Office Action for IL Application 216154 dated Dec. 18, 2014.
Office Action for U.S. Appl. No. 13/332,430 dated May 30, 2012.
Office Action for U.S. Appl. No. 13/332,430 dated Oct. 15, 2012.
Official Action Dated Aug. 1, 2013 From the US Patent and Trademark Office re U.S. Appl. No. 13/318,636.
Official Action Dated Jan. 7, 2013 From the US Patent and Trademark Office Re: U.S. Appl. No. 13/318,636.
Official Action Dated Apr. 15, 2014 From the US Patent and Trademark Office Re. U.S. Appl. No. 13/446,557.
Official Action Dated Mar. 18, 2011 From the US Patent and Trademark Office Re. U.S. Appl. No. 12/222,949.
Official Action Dated Sep. 23, 2010 From the US Patent and Trademark Office Re. U.S. Appl. No. 12/222,949.
Official Action Dated Jun. 28, 2010 From the US Patent and Trademark Office Re. U.S. Appl. No. 12/222,949.
Palacios et al. "Genetic analysis of Israel Acute Paralysis Virus: Distinct Clusters Are Circulating in the United States", Journal of

(56) References Cited

OTHER PUBLICATIONS

Virology, XP002533681, 82(13): 6209-6217, Jul. 2008. Database EMBL [Online], Retrieved From EBI, Database Accession No. EU436456, Jun. 19, 2008.
Palacios et al. "Israel Acute Paralysis Virus of Bees Strain OZ6-AUSTRALIA-2007, Complete Genome", Database EMBL [Online], XP002533681, Retrieved From EBI, Database Accession No. EU436456, Jun. 19, 2008.
Paldi et al. "Effective Gene Silencing in a Microsporidian Parasite Associated With Honeybee (*Apis mellifera*) Colony Declines", Applied and Environmental Microbiology, 76(17): 5960-5964, Sep. 2010.
Patel et al. "The Making of a Queen: TOR Pathway is a Key Player in Diphenic Caste Development", PLoS One, 2(6): e509-1-e509-7, Jun. 2007.
Patent Examination Report Dated Nov. 6, 2014 From the Australian Government, IP Australia Re. Application No. 2010244122.
Patent Examination Report dated Oct. 23, 2013 from the Australian Government, IP Australia re Application No. 2008325989.
Peyretaillade et al. "Microsporidian Encephalitozoon Cuniculi, A Unicellular Eukaryote With an Unusual Chromosomal Dispersion of Ribosomal Genes and A LSU rRNA Reduced to the Universal Core", Nucleic Acids Research, 26(15): 3513-3520, 1998.
Price et al. "RNAi-Mediated Crop Protection Against Insects", Trends in Biotechnology, XP022757296, 26(7): 393-400, Jul. 2008.
Restriction Official Action Dated Feb. 5, 2014 From the US Patent and Trademark Office Re. U.S. Appl. No. 13/446,557.
Robalino et al. "Double-Stranded RNA and Antiviral Immunity in Marine Shrimp: Inducible Host Mechanisms and Evidence for the Evolution of Viral Counter-Responses", Developmental & Comparative Immunology, 31: 539-547, 2007.
Siomi et al. "On the Road to Reading the RNA-Interference Code", Nature, 457(7228): 396-404, Jan. 22, 2009. Abstract.
Slamovits et al. "Genome Compaction and Stability in Microsporidian Intracellular Parasites", Current Biology, 14(10): 891-896, May 25, 2004.
Standifer "Honey Bee Nutrition and Supplemental Feeding", Beekeeping in the United States Agriculture Handbook, 335; 39-45, Oct. 1980.
Steeves et al. "Transgenic Soybeans Expressing SiRNAs Specific to a Major Sperm Protein Gene Suppress Heterodera Glycines Reproduction", Functional Plant Biology, 33(11): 991-999, Nov. 1, 2006. Abstract.
Requisition by the Examiner and Examination Search Report Dated Mar. 19, 2015 From the Canadian Intellectual Property Office Re. Application No. 2,704,858.
Communication Pursuant to Article 94(3) EPC Dated May 29, 2015 From the European Patent Office Re. Application No. 13156180.5.
Office Action for IN Application 1150/MUMNP/2010 dated Mar. 20, 2015.
Office Action for U.S. Appl. No. 13/932,051 dated May 4, 2015.
Shen et al., "The Role of Varroa Mites in Infections of Kashmir Bee Virus (KBV) and Deformed Wing Virus (DMV) in Honey Bees", Virology, 2005, pp. 141-149, vol. 342.
Communication Pursuant to Article 94(3) EPC Dated Jun. 8, 2015 From the European Patent Office Re. Application No. 13156185.4.
Decision on Rejection Dated Aug. 3, 2015 From the State Intellectual Property Office of the People's Republic of China Re. Application No. 201080056585.9 and its Translation Into English.
Communication Pursuant to Article 94(3) EPC Dated Sep. 1, 2015 From the European Patent Office Re. Application No. 10779855.5.
Communication Pursuant to Article 94(3) EPC Dated Sep. 4, 2015 From the European Patent Office Re. Application No. 13156183.9.
Examination Report Dated Aug. 25, 2015 From the Intellectual Property Office of New Zealand Re. Application No. 700791.
Office Action Dated Sep. 28, 2015 From the US Patent and Trademark Office Re. U.S. Appl. No. 13/932,051.
Advisory Action Before the Filing of an Appeal Brief Dated Feb. 22, 2013 From the US Patent and Trademark Office Re: U.S. Appl. No. 13/332,430.
Akiyoshi et al. "Genomic Survey of the Non-Cultivatable Opportunistic Human Pathogen, Enterocytozoon Bieneusi", PLoS Pathogens, 5(1): e1000261: 1-10, Jan. 2009.
Amdam et al. "The Hive Bee to Forager Transition in Honeybee Colonies: The Double Repressor Hypothesis", Journal of Theoretical Biology, 223: 451-464, 2003.
Amdam et al., "Altered Physiology in Worker Honey Bees (*Hymenoptera*: Apidae) Infested with the Mite *Varroa destructor* (*Acari*: Varroidae): A Factor in Colony Loss During Overwintering", Journal of Economic Entomology, 2004, pp. 741-747, vol. 97 No. 3.
Applicant-Initiated Interview Summary Dated Mar. 5, 2013 From the US Patent and Trademark Office Re: U.S. Appl. No. 13/332,430.
Aronstein et al. "SID-I is Implicated in Systemic Gene Silencing in the Honey Bee", Journal of Agricultural Research and Bee World, XP009115329, 45(1): 20•-24, Jan. 2006.
Baum et al. "Control of Coleopteran Insect Pests Through RNA Interference", Nature Biotechnology, 25(11): 1322-1326, Nov. 2007, Advance Online Publication, Nov. 4, 2007.
Burri et al. "Microsporidian Mitosomes Retain Elements of the General Mitochondrial Targeting System", Proc. Natl. Acad. Sci. USA, 103(43): 15916-15920, Oct. 24, 2006.
Campbell et al. "Gene-Knockdown in the Honey Bee Mite *Varroa destructor* by a Non-Invasive Approach: Studies on a Glutathione S-Transferase", Parasites & Vectors, XP002621493, 3(73): 1-10, Aug. 16, 2010. Abstract.
Carthew "Gene Silencing by Double-Stranded RNA", Current Opinion in Cell Biology, XP002263320, 13: 244-248, 2001.
Chawla-Sarkar et al., "Downregulation of Bcl-2, FLIP or IAPs (XIAP and Survivin) by siRNAs Sensitizes Resistant Melanoma Cells to Apo2L/TRAIL-Induced Apoptosis", Cell Death and Differentiation, 2004, pp. 915-923, vol. 11.
Chen et al. "High Throughput Genome-Wide Survey of Small RNAs From the Parasitic Protists Giardia Intestinalis and Trichomonas Vaginalis", Genome, Biology and Evolution, p. 165-175, Jul. 6, 2009.
Chen et al. "Nosema Ceranae is a Long-Present and Wide-Spread Microsporidian Infection of the European Honey Bee (*Apis mellifera*) in the United States", Journal of Invertebrate Pathology, XP022438643, 97(2): 186-188, Jan. 29, 2008.
Communication Pursuant to Article 94(3) EPC Dated Feb. 5, 2015 From the European Patent Office Re. Application No. 13156183.9.
Communication Pursuant to Article 94(3) EPC Dated Feb. 6, 2015 From the European Patent Office Re. Application No. 10719620.6.
Communication Pursuant to Article 94(3) EPC dated Oct. 8, 2013 from the European Patent Office re Application No. 10719620.6.
Communication Pursuant to Article 94(3) EPC Dated Jul. 12, 2013 From the European Patent Office Re. Application No. 08847971.2.
Communication Pursuant to Article 94(3) EPC Dated Feb. 17, 2011 From the European Patent Office Re. Application No. 08847971.2.
Communication Pursuant to Article 94(3) EPC Dated Feb. 17, 2014 from the European Patent Office Re. Application No. 08847971.2.
Communication Pursuant to Article 94(3) EPC for EP Application No. 08847971.2 dated Jun. 29, 2012.
Communication Relating to the Results of the Partial International Search Dated May 13, 2009 From the International Searching Authority Re.: Application No. PCT/IL2008/001440.
Communication Relating to the Results of the Partial International Search Dated Jul. 24, 2013 From the International Searching Authority re Application No. PCT/IL2013/050321.
Cornman et al. "Genomic Analyses of the Microsporidian Nosema Ceranae, An Emergent Pathogen of Honey Bees", PLoS Pathogens, 5(6): e1000466: 1-14, Jun. 2009.
Cox-Foster et al. "A Metagenomic Survey of Microbes in Honey Bee Colony Collapse Disorder", Science, XP002533680, 318(5848): 283-287, Oct. 2007. Database EMBL [Online], Retrieved From EBI, Database Accession No. EU122366, Nov. 15, 2007.
Cox-Foster et al. "Israel Acute Paralysis Virus of Bees Isolate IAPV.OP2 RNA-Dependent RNA Polymerase and Structural Polyprotein Genes, Partial CDs", Database EMBL [Online], XP002533680, Retrieved From EBI, Database Accession No. EU122366, Nov. 15, 2007.

(56) References Cited

OTHER PUBLICATIONS

Cox-Foster et al. "Saving the Honeybee. The Mysterious Ailment Called Colony Collapse Disorder Has Wiped Out Large Numbers of the Bees That Pollinate a Third of Our Crops", Scientific American, p. 40-47, Apr. 2009.
De La Fuente et al. "RNA Interference for the Study and Genetic Manipulation of Ticks", Trends in Parasitology, 23(9): 427-433, Sep. 2007. Abstract.
Di Prisco et al. "Varroa Destructor is an Effective Vector of Israeli Acute Paralysis Virus in the Honeybee, *Apis Mellifera*", Journal of General Virology, 92: 151-155, 2011.
Dietemann et al., "Varroa Destructor: Research Avenues Toward Sustainable Control", Journal of Apicultural Research, XP055069108, 2012, pp. 125-132, vol. 51, No. 1.
European Search Report and the European Search Opinion Dated Feb. 3, 2014 From the European Patent Office Re. Application No. 13156180.5.
European Search Report and the European Search Opinion Dated Feb. 3, 2014 From the European Patent Office Re. Application No. 13156185.4.
European Search Report and the European Search Opinion Dated Feb. 6, 2014 From the European Patent Office Re. Application No. 13156183.9.
Examination Report Dated May 12, 2014 From the Instituto Mexicano de la Propiedad Industrial Re. Application No. MX/a/2012/004378 and its Translation Into English.
Examination Report Dated Jan. 30, 2015 From the Instituto Mexicano de la Propiedad Industrial Re. Application No. MX/a/2012/004378 and its Translation Into English.
Examination Report Dated Oct. 31, 2013 From the Instituto Mexicano de la Propiedad Industrial re Application No. MX/a/2012/004378 and its Summary in English.
Fairbairn et al. "Host-Delivered RNAi: An Effective Strategy to Silence Genes in Plant Parasitic Nematodes", Planta, 226(6): 1525-1533, Nov. 2007. Abstract.
Franco Nunes et al. "A Non-Invasive Method for Silencing Gene Transcription in Honeybees Maintained Under Natural Conditions", Insect Biochemistry and Molecular Biology, XP002523702, 39(2): 157-160, Feb. 2009.
Garbian et al., "Bidirectional Transfer of RNAi Between Honey Bee and *Varroa destructor: Varroa* Gene Silencing Reduces *Varroa* Population", PLOS Pathogens, XP055069058, 2012, pp. 1-9, vol. 8, Issue 12.
Gill et al. "Stripped-Down DNA Repair in a High Reduced Parasite", BMC Molecular Biology, 8(24): 1-14, Mar. 20, 2007.
Henderson et al. "U.S. National Bee Colony Loss Survey, www.beesurvey.com, Preliminary Findings With Respect to Colony Collapse Disorder (CCD)", Bee Alert Technology, Inc., Mar. 26, 2007.
Hunter et al. "Large-Scale Field Application of RNAi Technology Reducing Israeli Acute Paralysis Virus Disease in Honey Bees (*Apis mellifera, Hymenoptera*: apidae)", PLoS Pathogens, 6(12): e1001160-1-e1001160-10, Dec. 2010.
International Preliminary Report on Patentability (Chapter I) for PCT/IL2013/050321 issued Oct. 23, 2014.
International Preliminary Report on Patentability Dated Feb. 1, 2010 From the International Preliminary Examining Authority Re.: Application No. PCT/IL2008/001440.
International Preliminary Report on Patentability Dated Mar. 1, 2012 From the International Bureau of WIPO Re. Application No. PCT/IB2010/053776.
International Preliminary Report on Patentability Dated Nov. 17, 2011 From the International Bureau of WIPO Re. Application No. PCT/IB2010/051980.
International Preliminary Report on Patentability Dated Apr. 26, 2012 From the International Bureau of WIPO Re. Application No. PCT/IL2010/000844.
International Search Report and the Written Opinion Dated Jul. 19, 2010 From the International Searching Authority Re.: Application No. PCT/IB2010/051980.
International Search Report and the Written Opinion Dated Feb. 24, 2011 From the International Searching Authority Re. Application No. PCT/IL2010/000844.
International Search Report and the Written Opinion Dated Oct. 28, 2013 from the International Searching Authority re Application No. PCT/IL2013/8050321.
International Search Report and the Written Opinion Dated Nov. 30, 2010 From the International Searching Authority Re. Application No. PCT/IB2010/053776.
Baum et al., "Progress Towards RNAi-Mediated Insect Pest Management," *Advances in Insect Physiology*, 47:249-295 (2014).

* cited by examiner

COMPOSITIONS FOR CONTROLLING *VARROA* MITES IN BEES

RELATED APPLICATIONS

This application is continuation of U.S. patent application Ser. No. 13/446,557 filed on Apr. 13, 2012, which is a continuation-in-part (CIP) of PCT Patent Application No. PCT/IL2010/000844 filed Oct. 14, 2010, which claims the benefit of priority under 35 USC §119(e) of U.S. Provisional Patent Application No. 61/251,339 filed Oct. 14, 2009. The contents of the above applications are incorporated herein by reference in their entirety.

FIELD AND BACKGROUND OF THE INVENTION

The invention relates to compositions for controlling *Varroa* mite infestation in bees.

Honey bees, *Apis mellifera*, are required for the effective pollination of crops and are therefore critical to world agriculture. Honey bees also produce economically important products, including honey and bees wax. Honey bees are susceptible to a number of parasites and pathogens, including the ectoparasitic mite, *Varroa destructor.*

Colony Collapse Disorder (CCD) of honeybees is threatening to annihilate U.S. and world agriculture. Indeed, in the recent outbreak of CCD in the U.S. in the winter of 2006-2007, an estimated 25% or more of the 2.4 million honeybee hives were lost because of CCD. An estimated 23% of beekeeping operations in the United States suffered from CCD over the winter of 2006-2007, affecting an average of 45% of the beekeepers operations. In the winter of 2007-2008, the CCD action group of the USDA-ARS estimated that a total of 36% of all hives from commercial operations were destroyed by CCD.

CCD is characterized by the rapid loss from a colony of its adult bee population, with dead adult bees usually found at a distance from the colony. At the final stages of collapse, a queen is attended only by a few newly emerged adult bees. Collapsed colonies often have considerable capped brood and food reserves. The phenomenon of CCD was first reported in 2006; however, beekeepers noted unique colony declines consistent with CCD as early as 2004. Various factors such as mites and infectious agents, weather patterns, electromagnetic (cellular antennas) radiation, pesticides, poor nutrition and stress have been postulated as causes. To date, control of CCD has focused on *Varroa* mite control, sanitation and removal of affected hives, treating for opportunistic infections (such as *Nosema*) and improved nutrition. No effective preventative measures have been developed to date.

*Varroa* mites parasitize pupae and adult bees and reproduce in the pupal brood cells. The mites use their mouths to puncture the exoskeleton and feed on the bee's hemolymph. These wound sites in the exoskeleton harbor bacterial infections, such as Melissococcus pluton, which causes European foulbrood. In addition, to their parasitic effects, *Varroa* mites are suspected of acting as vectors for a number of honey bee pathogens, including deformed wing virus (DWV), Kashmir bee virus (KBV), acute bee paralysis virus (ABPV) and black queen cell virus (BQCV), and may weaken the immune systems of their hosts, leaving them vulnerable to infections. If left untreated *Varroa* infestations typically result in colony-level mortality.

Current methods of treating *Varroa* infestations are proving to be ineffective as the mites develop resistance to existing miticides. In addition, the use of such miticides may introduce injurious chemicals into honey that is intended for human consumption.

U.S. Patent Application 20090118214 teaches the use of dsRNA for prevention and treatment of viral infections in honeybees.

SUMMARY OF THE INVENTION

According to an aspect of some embodiments of the present invention there is provided an isolated nucleic acid agent comprising a nucleic acid sequence which downregulates expression of a gene product of a *Varroa destructor* mite.

According to an aspect of some embodiments of the present invention there is provided a nucleic acid construct comprising a nucleic acid sequence encoding the isolated nucleic acid agent of the present invention.

According to an aspect of some embodiments of the present invention there is provided a bee-ingestible composition comprising at least one nucleic acid agent which comprises a nucleic acid sequence which downregulates expression of a gene product of a *Varroa destructor* mite.

According to an aspect of some embodiments of the present invention there is provided a method of preventing or treating a *Varroa destructor* mite infestation of a bee hive, the method comprising administering to the bee an effective amount of least one nucleic acid agent which comprises a nucleic acid sequence which downregulates expression of a gene product of a *Varroa destructor* mite, thereby preventing or treating a *Varroa destructor* mite infestation of a bee hive.

According to an aspect of some embodiments of the present invention there is provided a method of preventing or treating a *Varroa destructor* mite infestation of a bee hive, the method comprising administering to the bee an effective amount of the nucleic acid construct of the present invention, thereby preventing or treating a *Varroa destructor* mite infestation of a bee hive.

According to an aspect of some embodiments of the present invention there is provided a method of reducing the susceptibility of honeybees to Colony Collapse Disorder (CCD), the method comprising administering to the honeybee an effective amount of at least one double-stranded ribonucleic nucleic acid (dsRNA), the at least one dsRNA comprising a sequence complementary to at least 21 nucleotides of *Varroa destructor* mite mRNA and capable of inducing degradation of the *Varroa destructor*-specific mRNA.

According to some embodiments of the invention, the nucleic acid sequence is complementary to at least 21 nucleotides of *Varroa destructor* mite specific RNA and capable of inducing degradation of the *Varroa destructor* mite RNA.

According to some embodiments of the invention, the agent is selected from the group consisting of a dsRNA, an antisense RNA and a ribozyme.

According to some embodiments of the invention, the dsRNA is selected from the group consisting of siRNA, shRNA and miRNA.

According to some embodiments of the invention, the gene product is an mRNA encoding a polypeptide selected from the group consisting of ATPase subunit A, RNA polymerase I, RNA polymerase III, Inhibitor of apoptosis (IAP), FAS apoptotic inhibitor and α-Tubulin.

According to some embodiments of the invention, the at least one nucleic acid agent comprises at least five nucleic acid agents, for down-regulating ATPase subunit A, RNA polymerase III, Inhibitor of apoptosis (IAP), FAS apoptotic inhibitor and α-Tubulin, each of the at least five nucleic acid agent targeting a different gene.

According to some embodiments of the invention, the at least one nucleic acid agent comprises at least six nucleic acid agents, for down-regulating ATPase subunit A, RNA polymerase I, RNA polymerase III, Inhibitor of apoptosis (IAP), FAS apoptotic inhibitor and α-Tubulin, each of the at least six nucleic acid agents for targeting a different gene.

According to some embodiments of the invention, the nucleic acid agents are as set forth in SEQ ID Nos: 1, 13, 27, 30 and 39.

According to some embodiments of the invention, the nucleic acid agents are as set forth in SEQ ID Nos: 93, 96, 100, 104 and 106.

According to some embodiments of the invention, the nucleic acid agents are as set forth in SEQ ID Nos: 1, 4, 7, 10, 13, 16, 19, 22, 25, 27, 30, 33, 36 and 39.

According to some embodiments of the invention, the nucleic acid agents are as set forth in SEQ ID Nos: 93-106.

According to some embodiments of the invention, the nucleic acid sequence is greater than 15 base pairs in length.

According to some embodiments of the invention, the nucleic acid sequence is 19 to 25 base pairs in length.

According to some embodiments of the invention, the nucleic acid sequence is greater than 30 base pairs in length.

According to some embodiments of the invention, the composition is in solid form.

According to some embodiments of the invention, the composition is in liquid form.

According to some embodiments of the invention, the composition comprises protein.

According to some embodiments of the invention, the protein is in the form of pollen and/or soy patties.

According to some embodiments of the invention, the liquid is a sucrose solution.

According to some embodiments of the invention, the liquid is a corn syrup solution.

According to some embodiments of the invention, the liquid further comprises a carbohydrate or sugar supplement.

According to some embodiments of the invention, the bee is a honeybee.

According to some embodiments of the invention, the honeybee is a forager.

According to some embodiments of the invention, the honeybee is a hive bee.

According to some embodiments of the invention, the honeybee is a bee of a colony, and wherein the administering reduces the susceptibility of the bee colony to Colony Collapse Disorder.

According to some embodiments of the invention, the administering is effected by feeding.

According to some embodiments of the invention, the feeding comprises providing a liquid bee-ingestible composition.

According to some embodiments of the invention, the feeding comprises providing a solid bee-ingestible composition.

According to some embodiments of the invention, the *Varroa destructor* mite mRNA encodes a polypeptide selected from the group consisting of NADH dehydrogenase subunit 2, ATP synthetase subunit 8, ATP synthetase subunit 6, sodium channel and cytochrome oxydase subunit I.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 9A-9C are graphs representing the means (±SE) of results of real-time RT-PCR of *Varroa* RNA with probes for *Varroa* gene mRNA: RNA polymerase III (9A, probes SEQ ID NOs. 137 and 138), IAP1 and IAP2 (9B, probes SEQ ID NOs. 141 and 142) and vacuolar proton ATPase (9C, probes SEQ ID NOs. 139 and 140), respectively. The *Varroa* RNA was extracted from mites infesting bees fed a mixture of 5 *Varroa*-specific dsRNAs (Mixture I), or from mites infesting bees fed a mixture of 14 *Varroa*-specific dsRNAs (Mixture II). Controls represent *Varroa* RNA extracted from mites infesting untreated bees or mites infesting bees fed irrelevant (GFP) dsRNA. FIGS. 9D-9F are photographs showing semi-quantitative RT-PCR of *Varroa* RNA illustrating specific silencing of *Varroa* apoptosis inhibitor FAS gene expression in mites infesting bees fed on *Varroa*-specific dsRNA. Apoptosis inhibitor FAS RNA was amplified (using primers SEQ ID NOs. 145 and 146) in *Varroa* RNA extracted from mites infesting bees fed a mixture of 5 *Varroa*-specific dsRNAs (9D, Mixture I), or from mites infesting bees fed a mixture of 14 *Varroa*-specific dsRNAs (9D, Mixture II). Controls represent amplification of Apoptosis inhibitor FAS RNA in *Varroa* RNA extracted from mites infesting untreated bees (9E, Untreated) or mites infesting bees fed irrelevant (9E, dsRNA-GFP) dsRNA. 9F is a control showing amplification of the housekeeping gene actin (using primers SEQ ID NOs. 147 and 148). Numbers indicate the number of cycles of amplification. −RT reactions serve as controls for DNA contamination. Note strong silencing of Apoptosis inhibitor FAS expression in mites infesting bees fed Mixture I or Mixture II (FIG. 9D);

DESCRIPTION OF EMBODIMENTS OF THE INVENTION

The present invention, in some embodiments thereof, relates to methods and compositions for reducing the susceptibility of bees to *Varroa* mite infestation.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Bees are susceptible to a myriad of viral infections. Treatment of such infections by down-regulation of a particular viral gene product has shown to be successful in eliminating virally induced infections in the bee (see U.S. Patent Application 20090118214).

The present inventors now propose treatment of *Varroa* mite infestations in bees by down-regulating particular *Varroa* mite gene products.

*Varroa* mites parasitize pupae and adult bees and reproduce in the pupal brood cells. The mites use their mouths to puncture the exoskeleton and feed on the bee's hemolymph. The present inventors unexpectedly found that polynucleotide agents administered to the bees to treat *Varroa* mite infestations presented in the bee's hemolymph thereby becoming available to the mite.

Figure 4:
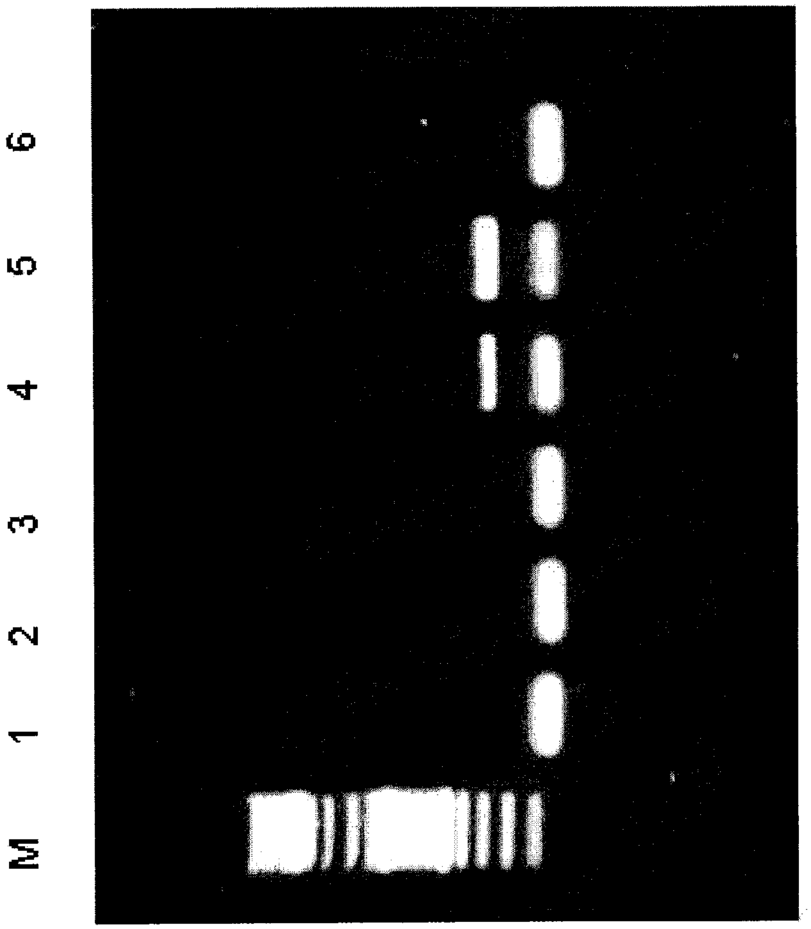
FIG. 4 is a photograph illustrating RT-PCR of *Varroa* RNA with primers to apoptosis inhibitor protein (IAP; sequence 27). M: size markers. Lanes 1-3: Template RNA of *Varroa* from hives treated with dsRNA of sequences 27. Lane 4: Template RNA of *Varroa* from control hives. Lane 5: Positive control (a IAP-carrying plasmid). Lane 6: Negative control (no template).
Figure 5:
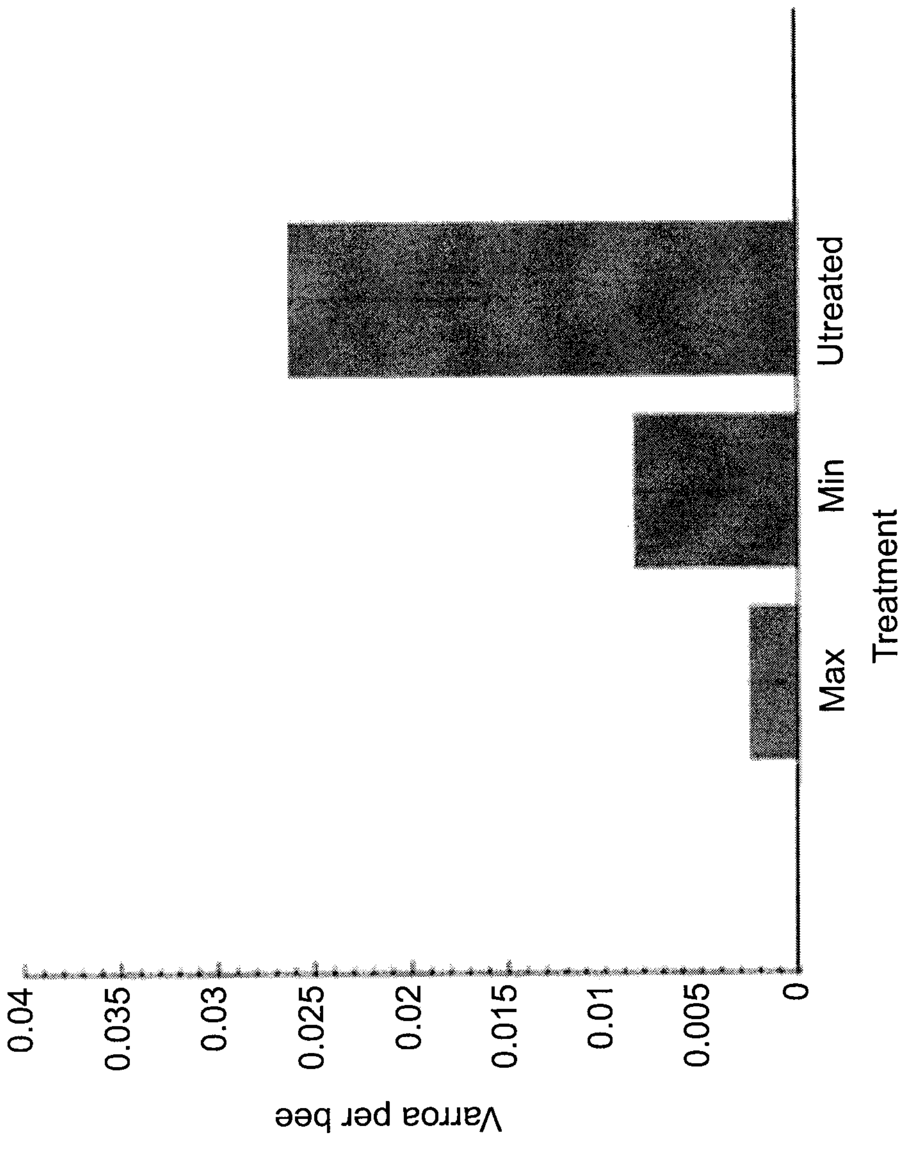
FIG. 5 is a bar graph illustrating the *Varroa* count per bee (adult bees plus larvae inside sealed cells) in control hives and in hives treated with dsRNA mixture I (Min) and with dsRNA mixture II (Max).
Figure 11:
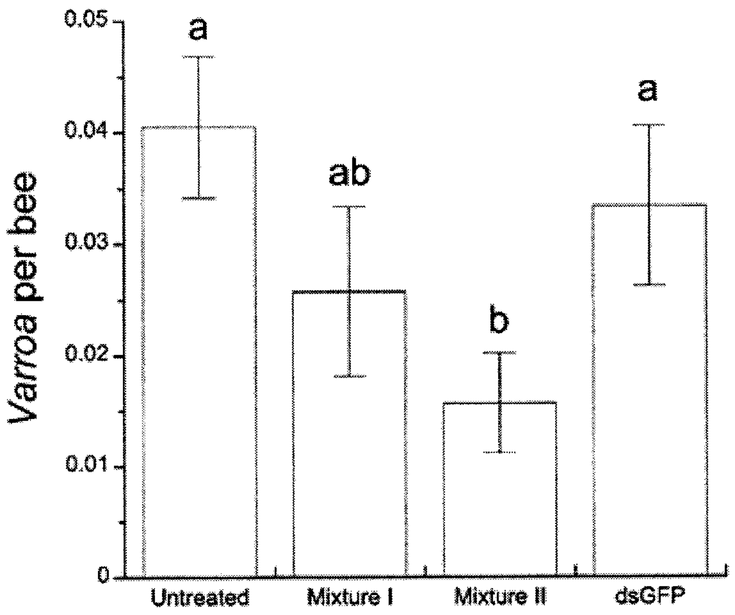
FIG. 11 is a graph showing *Varroa* infestation (number of mites) in treated bees and controls (as in FIG. 10), indicating significant reduction in susceptibility to *Varroa* infestation following feeding of the bees with Mixture I or Mixture II.

The present inventors have shown that dsRNA can successfully be transferred to Vorroa mites (FIGS. 2A-E, 6 and 7), that the dsRNA can serve to down-regulate expression of a particular gene in the *Varroa* mite (FIGS. 4 and 9A-9E) and further that targeting of particular genes for down-regulation can result in a reduction in the number of *Varroa* mites (FIGS. 5 and 11). Yet further, the present inventors have shown that RNA sequences transferred to mites from bees fed dsRNA can be transferred back to untreated, "naïve" bees via *Varroa* infestation (FIG. 7).

Thus, according to one aspect of the present invention there is provided a method of preventing or treating a *Varroa destructor* mite infestation of a bee, the method comprising administering to the bee an effective amount of a nucleic acid agent comprising a nucleic acid sequence which down-regulates expression of a gene product of a *Varroa destructor* mite, thereby preventing or treating a *Varroa destructor* mite infestation of a bee.

As used herein, the term "bee" refers to both an adult bee and pupal cells thereof. According to one embodiment, the bee is in a hive.

An adult bee is defined as any of several winged, hairy-bodied, usually stinging insects of the superfamily Apoidea in the order Hymenoptera, including both solitary and social species and characterized by sucking and chewing mouthparts for gathering nectar and pollen. Exemplary bee species include, but are not limited to, *Apis, Bombus, Trigona, Osmia* and the like. In one embodiment, bees include, but are not limited to bumblebees (*Bombus terrestris*), honeybees (*Apis mellifera*) (including foragers and hive bees) and *Apis cerana.*

According to one embodiment, the bee is part of a colony.

The term "colony" refers to a population of bees comprising dozens to typically several tens of thousand bees that cooperate in nest building, food collection, and brood rearing. A colony normally has a single queen, the remainder of the bees being either "workers" (females) or "drones" (males). The social structure of the colony is maintained by the queen and workers and depends on an effective system of communication. Division of labor within the worker caste primarily depends on the age of the bee but varies with the needs of the colony. Reproduction and colony strength depend on the queen, the quantity of food stores, and the size of the worker force. Honeybees can also be subdivided into the categories of "hive bees", usually for the first part of a workers lifetime, during which the "hive bee" performs tasks within the hive, and "forager bee", during the latter part of the bee's lifetime, during which the "forager" locates and collects pollen and nectar from outside the hive, and brings the nectar or pollen into the hive for consumption and storage.

According to this aspect of the present invention the agents of the present invention are used to prevent the *Varroa destructor* mite from living as a parasite on the bee, or larvae thereof.

The phrase "*Varroa destructor* mite" refers to the external parasitic mite that attacks honey bees *Apis cerana* and *Apis mellifera*. The mite may be at an adult stage, feeding off the bee, or at a larval stage, inside the honey bee brood cell.

As mentioned, the agents of the present invention are capable of downregulating expression of a gene product of a *Varroa destructor* mite.

As used herein, the phrase "gene product" refers to an RNA molecule or a protein.

According to one embodiment, the *Varroa destructor* mite gene product is one which is essential for mite viability. Down-regulation of such a gene product would typically result in killing of the *Varroa* mite. According to another embodiment, the *Varroa destructor* mite gene product is one which is essential for mite reproduction. Down-regulation of such a gene product would typically result in the prevention of reproduction of the *Varroa* mite and the eventual extermination of the mite population. According to yet another embodiment, the *Varroa destructor* mite gene product is one which is required to generate pathogenic symptoms in the bee.

Exemplary gene products that may be down-regulated according to this aspect of the present invention include, but are not limited to NADH dehydrogenase; subunit 2—Genbank accession NC_004454; ATP synthetase; subunit 8—NC_004454; ATP synthetase; subunit 6—NC_004454; sodium channel gene—Genbank accession No. FJ216963; Cytochrome oxydase subunit I—Genbank accession No. EF025469.

It will be appreciated that whilst the agents of the present invention are capable of downregulating expression of a gene product of a *Varroa destructor* mite, it is preferable that they downregulate to a lesser extent expression of the gene product in other animals, such as the bee. Accordingly, the agents of the present invention must be able to distinguish between the mite gene and the bee gene, down-regulating the former to a greater extent than the latter. According to another embodiment the agents of the present invention do not down-regulate the bee gene whatsoever. This may be effected by targeting a gene that is expressed differentially in the mite and not in the bee e.g. the mite sodium channel gene—FJ216963. Alternatively, the agents of the present invention may be targeted to mite-specific sequences of a gene that is expressed both in the mite and in the bee.

According to one embodiment the agents of the present invention target segments of *Varroa* genes that are at least 100 bases long and do not carry any sequence longer than 19 bases that is entirely homologous to any bee-genome sequence or human-genome sequence.

Examples of such gene segments are provided herein below:

SEQ ID NO: 1. *Varroa* gene homologous to ATPase subunit A (segment 1); SEQ ID NO: 2. *Varroa* gene homologous to ATPase subunit A (segment 2); SEQ ID NO: 3. *Varroa* gene homologous to ATPase subunit A (segment 3); SEQ ID NO: 4. *Varroa* gene homologous to ATPase subunit A (segment 4); SEQ ID NO: 5. *Varroa* gene homologous to ATPase subunit A (segment 5); SEQ ID NO: 6. *Varroa* gene homologous to ATPase subunit A (segment 6); SEQ ID NO: 7. *Varroa* gene homologous to ATPase subunit A (segment 7); SEQ ID NO: 8. *Varroa* gene homologous to ATPase subunit A (segment 8); SEQ ID NO: 9. *Varroa* gene homologous to ATPase subunit A (segment 9); SEQ ID NO: 10. *Varroa* gene homologous to RNA polymerase I (segment 1); SEQ ID NO: 11. *Varroa* gene homologous to RNA polymerase I (segment 2); SEQ ID NO: 12. *Varroa* gene homologous to RNA polymerase I (segment 3); SEQ ID NO: 13. *Varroa* gene homologous to RNA polymerase III (segment 1); SEQ ID NO: 14. *Varroa* gene homologous to RNA polymerase III (segment 2); SEQ ID NO: 15. *Varroa* gene homologous to RNA polymerase III (segment 3); SEQ ID NO: 16. *Varroa* gene homologous to RNA polymerase III (segment 4); SEQ ID NO: 17. *Varroa* gene homologous to RNA polymerase III (segment 5); SEQ ID NO: 18. *Varroa* gene homologous to RNA polymerase III (segment 6); SEQ ID NO: 19. *Varroa* gene homologous to RNA polymerase III (segment 7) SEQ ID NO: 20. *Varroa* gene homologous to RNA polymerase III (segment 8); SEQ ID NO: 21. *Varroa* gene homologous to RNA polymerase III (segment 9); SEQ ID NO: 22. *Varroa* gene homologous to Inhibitor of apoptosis (IAP; segment 1); SEQ ID NO: 23. *Varroa* gene homologous to Inhibitor of apoptosis (IAP; segment 2); SEQ ID NO: 24. *Varroa* gene homologous to Inhibitor of apoptosis (IAP; segment 3); SEQ ID NO: 25. *Varroa* gene homologous to Inhibitor of apoptosis (IAP; segment 4); SEQ ID NO: 26. *Varroa* gene homologous to Inhibitor of apoptosis (IAP; segment 5); SEQ ID NO: 27. *Varroa* gene homologous to Inhibitor of apoptosis (IAP; segment 6); SEQ ID NO: 28. *Varroa* gene homologous to Inhibitor of apoptosis (IAP; segment 7); SEQ ID NO: 29. *Varroa* gene homologous to Inhibitor of apoptosis (IAP; segment 8); SEQ ID NO: 30. *Varroa* gene homologous to FAS apoptotic inhibitor (segment 1); SEQ ID NO: 31. *Varroa* gene homologous to FAS apoptotic inhibitor (segment 2); SEQ ID NO: 32. *Varroa* gene homologous to FAS apoptotic inhibitor (segment 3); SEQ ID NO: 33. Varoa gene homologous to α-Tubulin (segment 1); SEQ ID NO: 34. Varoa gene homologous to α-Tubulin (segment 2); SEQ ID NO: 35. Varoa gene homologous to α-Tubulin (segment 3); SEQ ID NO: 36. Varoa gene homologous to α-Tubulin (segment 4); SEQ ID NO: 37. Varoa gene homologous to α-Tubulin (segment 5); SEQ ID NO: 38. Varoa gene homologous to α-Tubulin (segment 6); SEQ ID NO: 39. Varoa gene homologous to α-Tubulin (segment 7); SEQ ID NO: 40. Varoa gene homologous to α-Tubulin (segment 8); SEQ ID NO: 41. Varoa gene homologous to α-Tubulin (segment 9); SEQ ID NO: 42.NADH dehydrogenase; subunit 2 (NC_004454): bases 709 to 974; SEQ ID NO: 43. ATP synthetase; subunit 8 (NC_004454): bases 3545 to 3643; SEQ ID NO: 44. Sodium channel protein (AY259834): bases 3336-3836.

Additional examples of sequences representing target *Varroa* gene segments include, but are not limited to the nucleic acid sequences of *Varroa* genes flanked by T7 promoter sequences in the following sequences (length of *Varroa*-specific sequence is indicated in parentheses):

SEQ ID NO: 93-*Varroa* gene homologous to α-tubulin (411 bases); SEQ ID NO: 94-*Varroa* gene homologous to α-tubulin (277 bases); SEQ ID NO: 95-*Varroa* gene homologous to α-tubulin (329 bases); SEQ ID NO: 96-*Varroa* gene homologous to RNA polymerase III (380 bases); SEQ ID NO: 97-*Varroa* gene homologous to RNA polymerase III (426 bases); SEQ ID NO: 98-*Varroa* gene homologous to RNA polymerase II (366 bases); SEQ ID NO: 99-*Varroa* gene homologous to RNA polymerase I (324 bases); SEQ ID NO: 100-*Varroa* gene homologous to vacuolar translocating ATPase (311 bases); SEQ ID NO: 101-*Varroa* gene homologous to vacuolar proton ATPase (210 bases); SEQ ID NO: 102-*Varroa* gene homologous to Na+/K+ ATPase (307 bases); SEQ ID NO: 103-*Varroa* gene homologous to apoptosis inhibitor IAP (263 bases); SEQ ID NO: 104-*Varroa* gene homologous to apoptosis inhibitor FAS (277 bases); SEQ ID NO: 105-*Varroa* gene homologous to apoptosis inhibitor IAP 1 and IAP2 (263 bases); SEQ ID NO: 106-*Varroa* gene homologous to apoptosis inhibitor IAP 1 and IAP2, reverse orientation (282 bases).

It will be appreciated that more than one gene may be targeted in order to maximize the cytotoxic effect on the *Varroa* mites.

Thus, according to one embodiment, the following group of genes are targeted—ATPase subunit A, RNA polymerase III, Inhibitor of apoptosis (IAP), FAS apoptotic inhibitor and α-Tubulin (e.g. using nucleic acid agents having the sequence as set forth in 1, 13, 27, 30 and 39, or nucleic acid agents having the sequence as set forth in SEQ ID Nos. 93, 96, 100, 104 and 106).

According to another embodiment, the following group of genes are targeted—ATPase subunit A, RNA polymerase I, RNA polymerase III, Inhibitor of apoptosis (IAP), FAS apoptotic inhibitor and α-Tubulin.

It will be appreciated that as well as down-regulating a number of genes, the present invention further contemplates using a number of agents to down-regulate the same gene (e.g. a number of dsRNAs each hybridizing to a different segment of the same gene). Thus, for example, the present inventors showed maximal cytotoxic activity when the following mixture of dsRNAs was used: SEQ ID Nos:1, 4, 7, 10, 13, 16, 19, 22, 25, 27, 30, 33, 36 and 39, or SEQ ID Nos. 93-106 and less of a cytotoxic activity when the following mixture of dsRNAs was used: SEQ ID Nos: 1, 13, 27, 30 and 39, or SEQ ID Nos. 93, 96, 100, 104 and 106.

Tools which are capable of identifying species-specific sequences may be used for this purpose—e.g. BLASTN and other such computer programs As used herein, the term "downregulating expression" refers to causing, directly or indirectly, reduction in the transcription of a desired gene, reduction in the amount, stability or translatability of transcription products (e.g. RNA) of the gene, and/or reduction in translation of the polypeptide(s) encoded by the desired gene.

Downregulating expression of a gene product of a *Varroa destructor* mite can be monitored, for example, by direct detection of gene transcripts (for example, by PCR), by detection of polypeptide(s) encoded by the gene or bee pathogen RNA (for example, by Western blot or immunoprecipitation), by detection of biological activity of polypeptides encode by the gene (for example, catalytic activity, ligand binding, and the like), or by monitoring changes in the Vaarroa destructor mite (for example, reduced proliferation of the mite, reduced virulence of the mite, reduced motility of the mite etc) and by testing bee infectivity/pathogenicity.

Downregulation of a *Varroa destructor* mite gene product can be effected on the genomic and/or the transcript level using a variety of agents which interfere with transcription and/or translation (e.g., RNA silencing agents, Ribozyme, DNAzyme and antisense).

According to one embodiment, the agent which down-regulates expression of a *Varroa destructor* mite gene product is a polynucleotide agent, such as an RNA silencing agent According to this embodiment, the polynucleotide agent is greater than 15 base pairs in length.

As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene or bee pathogen RNA sequence. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

According to one embodiment, the dsRNA is greater than 30 bp. The use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

Another method of downregulating a *Varroa* mite gene product is by introduction of small inhibitory RNAs (siRNAs).

The term "siRNA" refers to small inhibitory RNA duplexes (generally between 18-30 basepairs, between 19 and 25 basepairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is theorized to result from providing Dicer with a substrate (27 mer) instead of a product (21 mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

The term “shRNA”, as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (SEQ ID NO: 4; Brummelkamp, T. R. et al. (2002) Science 296: 550) and 5'-UUUGUGUAG-3' (SEQ ID NO: 5; Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the “pri-miRNA”) is processed through various nucleolytic steps to a shorter precursor miRNA, or “pre-miRNA.” The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

In one embodiment of the present invention, synthesis of RNA silencing agents suitable for use with the present invention can be effected as follows. First, the *Varroa* mite target mRNA is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (wwwdotambiondotcom/techlib/tn/91/912dothtml).

Second, potential target sites are compared to an appropriate genomic database (e.g., human, bee, mouse, rat etc.) using any sequence alignment software, such as the BLAST software available from the NCBI server (wwwdotncbidotnlmdotnihdotgov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene or sequence for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene or bee pathogen target sequence.

For example, a siRNA that may be used in this aspect of the present invention is one which targets a mite-specific gene. Exemplary siRNAs are provided in SEQ ID NOs: 45-47.

SEQ ID NO: 45: attttattcaattaaagtatt

SEQ ID NO: 46: atacctcaaatgtatccttca

SEQ ID NO: 47: ggccaatcccgattccggcga

It will be appreciated that the RNA silencing agent of the present invention need not be limited to those molecules containing only RNA, but further encompasses chemically-modified nucleotides and non-nucleotides.

In some embodiments, the RNA silencing agent provided herein can be functionally associated with a cell-penetrating peptide. As used herein, a “cell-penetrating peptide” is a peptide that comprises a short (about 12-30 residues) amino acid sequence or functional motif that confers the energyindependent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cystein residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pIsl, TAT (48-60), pVEC, MTS, and MAP.

Another agent capable of downregulating a *Varroa* mite gene product is a DNAzyme molecule capable of specifically cleaving an mRNA transcript or DNA sequence of the bee pathogen polypeptide. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Downregulation of Varrao mite gene products can also be effected by using an antisense polynucleotide capable of specifically hybridizing with an mRNA transcript encoding the *Varroa* mite gene product.

Design of antisense molecules which can be used to efficiently downregulate a Varrao mite gene product must be effected while considering two aspects important to the antisense approach. The first aspect is delivery of the oligonucleotide into the cytoplasm of the appropriate cells, while the second aspect is design of an oligonucleotide which specifically binds the designated mRNA or RNA target sequence within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Another agent capable of downregulating a *Varroa* mite gene product is a ribozyme molecule capable of specifically cleaving an mRNA transcript encoding the *Varroa* mite gene product.

Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA, including viral RNA, has rendered them valuable tools in both basic research and therapeutic applications.

An additional method of downregulating the expression of a *Varroa* mite gene product in cells is via triplex forming oligonuclotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonuclotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| | | | | |
|---|---|---|---|---|
| oligo | 3'--A | G | G | T |
| duplex | 5'--A | G | C | T |
| duplex | 3'-T | C | G | A |

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression.

Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

The polynucleotide down-regulating agents of the present invention may be generated according to any polynucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the polynucleotides is well within the capabilities of one skilled in the art and can be accomplished via established methodologies as detailed in, for example, “Molecular Cloning: A laboratory Manual” Sambrook et al., (1989); “Current Protocols in Molecular Biology” Volumes I-III Ausubel, R. M., ed. (1994); Ausubel et al., “Current Protocols in Molecular Biology”, John Wiley and Sons, Baltimore, Md. (1989); Perbal, “A Practical Guide to Molecular Cloning”, John Wiley & Sons, New York (1988) and “Oligonucleotide Synthesis” Gait, M. J., ed. (1984) utilizing solid phase chemistry, e.g. cyanoethyl phosphoramidite followed by deprotection, desalting and purification by for example, an automated trityl-on method or HPLC.

The polynucleotide agents of the present invention may comprise heterocylic nucleosides consisting of purines and the pyrimidines bases, bonded in a 3' to 5' phosphodiester linkage.

Preferably used polynucleotide agents are those modified in either backbone, internucleoside linkages or bases, as is broadly described hereinunder.

Specific examples of preferred polynucleotide agents useful according to this aspect of the present invention include polynucleotide agents containing modified backbones or non-natural internucleoside linkages. Polynucleotide agents having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466, 677; 5,476,925; 5,519,126; 5,536,821; 5,541,306; 5,550,111; 5,563,253; 5,571,799; 5,587,361; and 5,625,050.

Preferred modified polynucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other polynucleotide agents which can be used according to the present invention, are those modified in both sugar and the internucleoside linkage, i.e., the backbone, of the nucleotide units are replaced with novel groups. The base units are maintained for complementation with the appropriate polynucleotide target. An example for such an polynucleotide mimetic, includes peptide nucleic acid (PNA). A PNA polynucleotide refers to a polynucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Polynucleotide agents of the present invention may also include base modifications or substitutions. As used herein, “unmodified” or “natural” bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

Following synthesis, the polynucleotide agents of the present invention may optionally be purified. For example, polynucleotides can be purified from a mixture by extraction with a solvent or resin, precipitation, electrophoresis, chromatography, or a combination thereof. Alternatively, polynucleotides may be used with no, or a minimum of, purification to avoid losses due to sample processing. The polynucleotides may be dried for storage or dissolved in an aqueous solution. The solution may contain buffers or salts to promote annealing, and/or stabilization of the duplex strands.

It will be appreciated that a polynucleotide agent of the present invention may be provided per se, or as a nucleic acid construct comprising a nucleic acid sequence encoding the polynucleotide agent.

Typically, the nucleic acid construct comprises a promoter sequence which is functional in the host cell, as detailed herein below.

The polynucleotide sequences of the present invention, under the control of an operably linked promoter sequence, may further be flanked by additional sequences that advantageously affect its transcription and/or the stability of a resulting transcript. Such sequences are generally located upstream of the promoter and/or downstream of the 3' end of the expression construct.

The term “operably linked”, as used in reference to a regulatory sequence and a structural nucleotide sequence, means that the regulatory sequence causes regulated expression of the linked structural nucleotide sequence. “Regulatory sequences” or “control elements” refer to nucleotide sequences located upstream, within, or downstream of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, termination sequences, pausing sequences, polyadenylation recognition sequences, and the like.

It will be appreciated that the nucleic acid agents can be delivered to the *Varroa* mites in a great variety of ways.

According to one embodiment, the nucleic acid agents are delivered directly to the mites (e.g. by spraying an infested hive). The nucleic acid agents, or constructs encoding same may enter the mites bodies by diffusion. In this embodiment, the promoter of the nucleic acid construct is typically operational in mite cells.

It will be appreciated that since *Varroa* mites use their mouths to puncture the bee exoskeleton and feed on the bee’s hemolymph, the present invention contemplates delivering the polynucleotide agents of the present invention to the bees, whereby they become presented in the bee’s hemolymph thereby becoming available to the mite. Thus, according to another embodiment, the nucleic acid agents are delivered indirectly to the mites (e.g. via the bee). In this embodiment, the promoter of the nucleic acid construct is typically operational in bee cells.

According to one embodiment, the nucleic acid agents are delivered to the bees by spraying. The nucleic acid agents, or constructs encoding same may enter the bees bodies by diffusion.

According to another embodiment, the nucleic acid agents are delivered to the bees via its food. The present inventors consider that following ingestion of the nucleic acid agents of the present invention, the agents will be presented in the bee’s hemolymph, whereby it becomes available to the *Varroa* mite.

Thus the polynucleotides of the present invention may be synthesized in vitro and added to the food. For example double stranded RNA may be synthesized by adding two opposing promoters (e.g. T7 promoters; SEQ ID NOs: 48 and 49) to the ends of the gene segments, wherein SEQ ID NO: 48 is placed immediately 5' to the gene and SEQ ID NO: 49 is placed immediately 3' to the gene segment. The dsRNA may then be transcribed in vitro with the T7 RNA polymerase.

Exemplary sequences for synthesizing dsRNA according to embodiments of the present invention are provided in SEQ ID NOs: 50-91 and 93-106.

Exemplary primers for synthesizing dsRNA, according to embodiments of the present invention are provided in SEQ ID NOs: 107-134 (each pair represents a forward and a reverse primer, see Table 1 in the Examples section).

As detailed herein, bee feeding is common practice amongst bee-keepers, for providing both nutritional and other, for example, supplemental needs. Bees typically feed on honey and pollen, but have been known to ingest non-natural feeds as well. Bees can be fed various foodstuffs including, but not limited to Wheast (a dairy yeast grown on cottage cheese), soybean flour, yeast (e.g. brewer’s yeast, torula yeast) and yeast products products-fed singly or in combination and soybean flour fed as a dry mix or moist cake inside the hive or as a dry mix in open feeders outside the hive. Also useful is sugar, or a sugar syrup. The addition of 10 to 12 percent pollen to a supplement fed to bees improves palatability. The addition of 25 to 30 percent pollen improves the quality and quantity of essential nutrients that are required by bees for vital activity.

Cane or beet sugar, isomerized corn syrup, and type-50 sugar syrup are satisfactory substitutes for honey in the natural diet of honey bees. The last two can be supplied only as a liquid to bees.

Liquid feed can be supplied to bees inside the hive by, for example, any of the following methods: friction-top pail, combs within the brood chamber, division board feeder, boardman feeder, etc. Dry sugar may be fed by placing a pound or two on the inverted inner cover. A supply of water must be available to bees at all times. In one embodiment, pan or trays in which floating supports—such as wood chips, cork, or plastic sponge—are present are envisaged. Detailed descriptions of supplemental feeds for bees can be found in, for example, USDA publication by Standifer, et al 1977, entitled “Supplemental Feeding of Honey Bee Colonies” (USDA, Agriculture Information Bulletin No. 413).

It will be appreciated that Varro mites cause wound sites in the exoskeleton of bees. Such wound sites harbor bacterial infections, such as Melissococcus pluton, which causes European foulbrood. In addition, to their parasitic effects, *Varroa* mites are suspected of acting as vectors for a number of honey bee pathogens, including deformed wing virus (DWV), Kashmir bee virus (KBV), acute bee paralysis virus (ABPV) and black queen cell virus (BQCV), and may weaken the immune systems of their hosts, leaving them vulnerable to infections.

Thus, by killing the mites (or preventing reproduction thereof), the agents of the present invention may be used to prevent and/or treat bacterial infections such as Melissococcus pluton and viral infections caused by the above named viruses.

Since *Varroa* mite infestation and viral infections are thought to be responsible for colony collapse disorder (CCD), the present agents may also be used to prevent or reduce the susceptibility of a bee colony to CCD.

It will be appreciated that in addition to feeding of oligonucleotides and/or polynucleotides for reduction of the bee pathogen infection and infestation, enforcement of proper sanitation (for example, refraining from reuse of infested hives) can augment the effectiveness of treatment and prevention of infections.

It is expected that during the life of a patent maturing from this application many relevant methods for downregulating expression of gene products will be developed and the scope of the term "downregulating expression of a gene product of a *Varroa destructor* mite" is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Feeding *Varroa*-Specific dsRNA Prevents *Varroa* Mite Infestation

Figure 1:
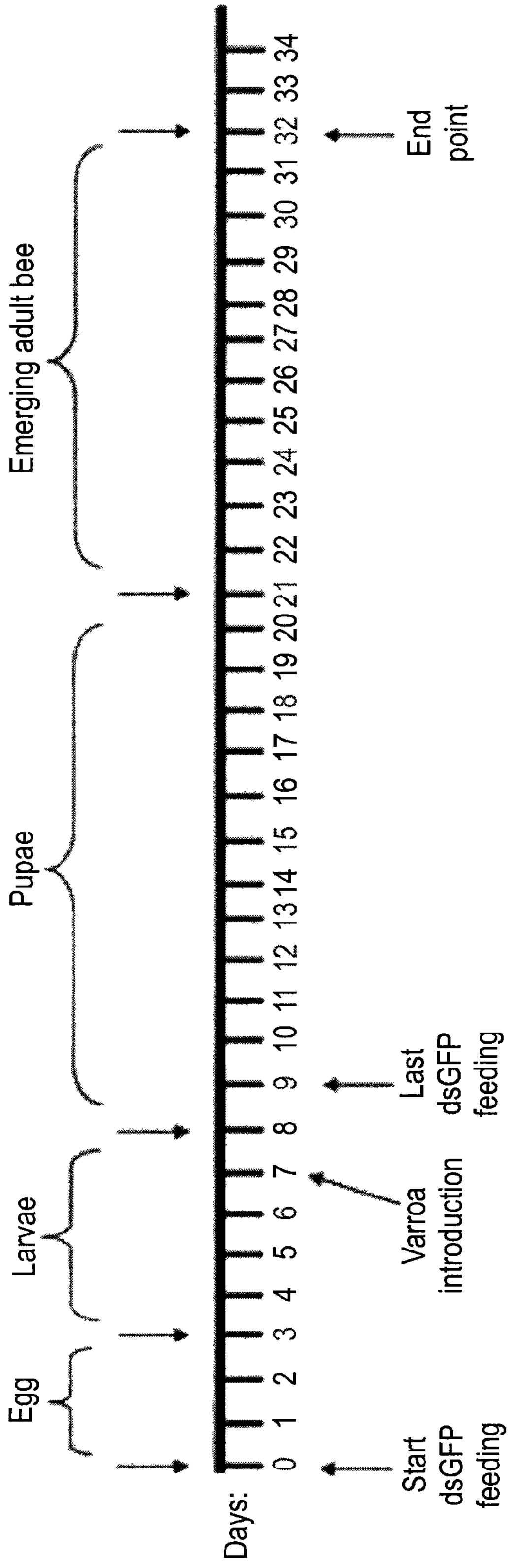
FIG. 1 is a schematic representation of the time-course of various experiment for dsRNA transfer to *Varroa* mites.
Figure 2A:
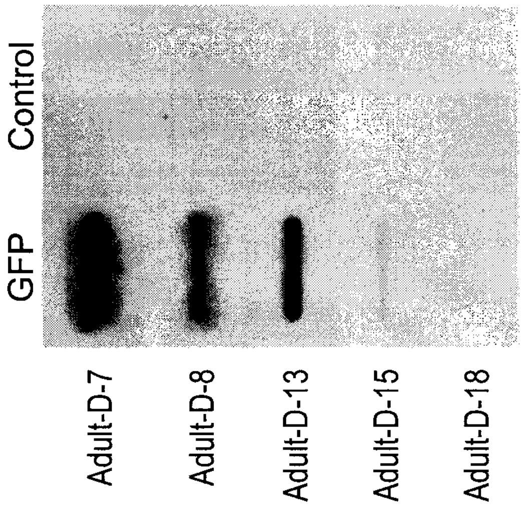
FIGS. 2A-E are photographs of the results of Slot blot analysis of the presence of dsRNA-GFP in ingested bees (FIG. 2A), in larvae fed by adult bees (FIG. 2B), in pupae (FIG. 2C), and in the newly-emerge bees (FIG. 2D). The presence of dsRNA-GFP and of siRNA derived from it was analyzed by Northern blots (FIG. 2E). D=days after administration of dsRNA-GFP to the hive.
Figure 2B:
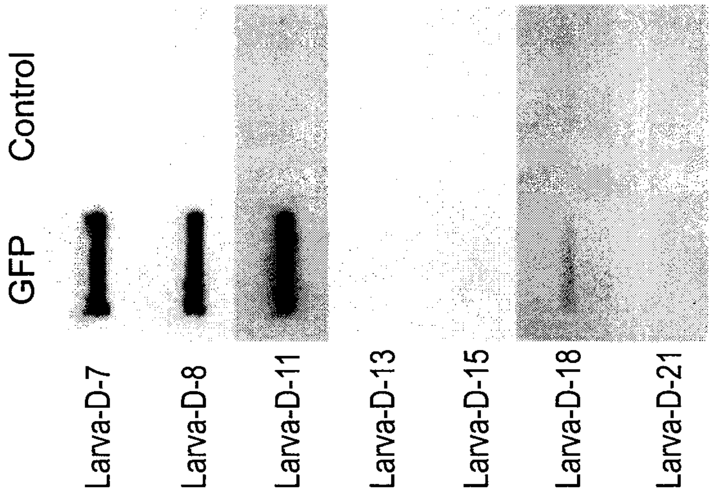
Figure 2C:
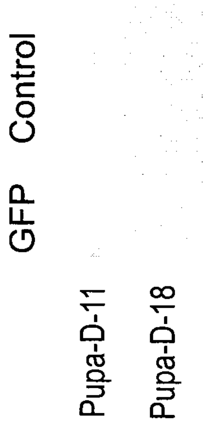
Figure 2D:
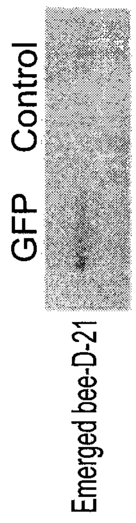
Figure 2E:
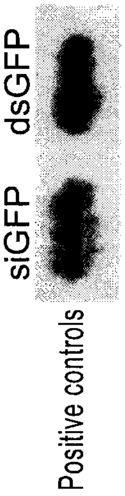

In order to determine the effectiveness of ingested dsRNA on *Varroa* mite infestation, honeybees are provided with *Varroa* mite-specific and control dsRNA in the feed for 7 days before, and 2 days following contact with the *Varroa* mite, as illustrated in FIG. 1. Numbers of dead *Varroa* per experimental hive are counted, and sample live and dead *Varroa* are collected for molecular analysis.

Materials and Methods

Establishment of Mini-Hive Colonies:

Young, approximately 2-month-old queens, together with approximately 200 worker bees are collected from hives in a local apiary. The bees are transferred into mini-hives fitted with one mini comb that was previously built by a regular hive. All of the mini-hives are closed and placed in a temperature-controlled room (30° C.).

dsRNA Preparation:

*Varroa* mite sequences are cloned into a plasmid between two opposing T7 promoters. Following propagation of plasmid DNA, the viral fragments, including the T7 promoters, are excised and gel-purified. These serve as templates for T7-directed in-vitro transcription (MEGAscript™, Ambion, Austin Tex.). The reaction product is submitted to DNase digestion followed by phenol extraction and ethanol precipitation. The final preparation is dissolved in nuclease-free water.

dsRNA Feeding in Minihives:

5 gr. pollen supplement patties are placed on top of each comb and 10 ml of 50% sucrose solution is introduced into the hive in a sterile Petri dish nightly. The feeding is continued for 9 days and subsequently only hives in which queens had begun to lay eggs are included in the trial.

Following establishment of active hives (queens laying eggs), some of the mini-hives are supplemented with *Varroa* mite-specific (apoptosis inhibitor (IAP) gene (SEQ ID NO: 27) or non-specific control (e.g. GFP SEQ ID NO: 91) dsRNA, which is added to the 10 ml 50% sugar solution given to the hives, adjusted to approximately 1 microgram dsRNA per feed per bee, assuming all bees consume approximately the same amount of sucrose solution. dsRNA feeding is continued for six days.

*Varroa* Mite Infestation in Minihives:

7 days after feeding in active hives, some of the colonies are placed in contact with a population of *Varroa* mites. Thereafter, dsRNA treatment is continued for a further 2 days. Samples of live and dead bees (larvae and adults) are collected daily from each mini-hive post introduction of the *Varroa* mite population for 32 consecutive days. Every bee collected is frozen in liquid nitrogen and preserved at −70° C. pending molecular analysis. Vitality of the colonies are monitored by opening the hives (without smoke), withdrawing the mini-comb and photographing the mini-comb from both sides. The hive-combs are photographed daily, and the numbers of remaining live bees are monitored. The photographs are downloaded onto a computer and the total number of bees is counted for every mini-hive.

To test dsRNA toxicity, another group of hives are provided with *Varroa* mite-specific dsRNA, but is not placed in contact with the *Varroa* mite population. Two sets of hives serve as additional controls: hives that are not treated with dsRNA and are not inoculated with *Varroa* mites, and hives that were not treated with dsRNA, but were inoculated with *Varroa* mites.

RT-PCR Analysis:

Extraction of Nucleic Acids:

Total RNA is extracted from the preserved bees using the TRIREAGENT method (Sigma, St. Louis Mo., USA). Briefly, RNA is extracted by precipitation and separation by centrifugation, then resuspended in RNAsecure solution.

Real-Time RT-PCR:

Measured amounts of RNA (100 ng for viral expression analyses and 100 pg for 18S rRNA internal controls) are subjected to one-step RT-PCR using the SYBR Green PCR master mix with Taqman reverse transcriptase (Applied Biosystems, Foster City, Calif.). Real-time RT-PCR is conducted in GeneAmp PCR System 5700 (Applied Biosystems). Reactions performed without reverse transcriptase or without template should not result in any product.

Northern-Blot Analysis:

Total RNA is extracted from treated and control bees. Formaldehyde is added to the RNA to 1.8% and warmed to 65° C. The RNA, 15 μg per lane is electrophoresed on a 1.2% agarose gel at 70 V, 4° C. with stirring. The previously described amplified *Varroa* mite-RNA product is digoxigenin labeled and serves as a probe for hybridization. Detection is performed with the DIG luminescent detection kit (Roche Diagnostics GmbH, Mannheim, Germany). RNA sizes are estimated by comparison to electrophoresed RNA Molecular Weight Markers I (Roche). Hybridization is carried out at high stringency (0.1×SSC; 65° C.).

The Fate of Ingested *Varroa* Mite-Specific dsRNA in Honeybees:

In order to better understand the mechanism(s) of action by which dsRNA-*Varroa* mite protects the bees against *Varroa* mite infestation and its consequences, total RNA is extracted from dsRNA-*Varroa* mite treated, and non-treated control bees, submitted to digestion by a panel of nucleases, and separated on PAGE.

Results

The presence of dsRNA in the adult bee body in the bee larvae (fed by adult bees), in the bee pupa was determined by slot-blot hybridization with a probe for GFP. The processing of the dsRNA to siRNA was determined by Northern blots detecting small RNAs (FIGS. 2A-E).

Figure 3:
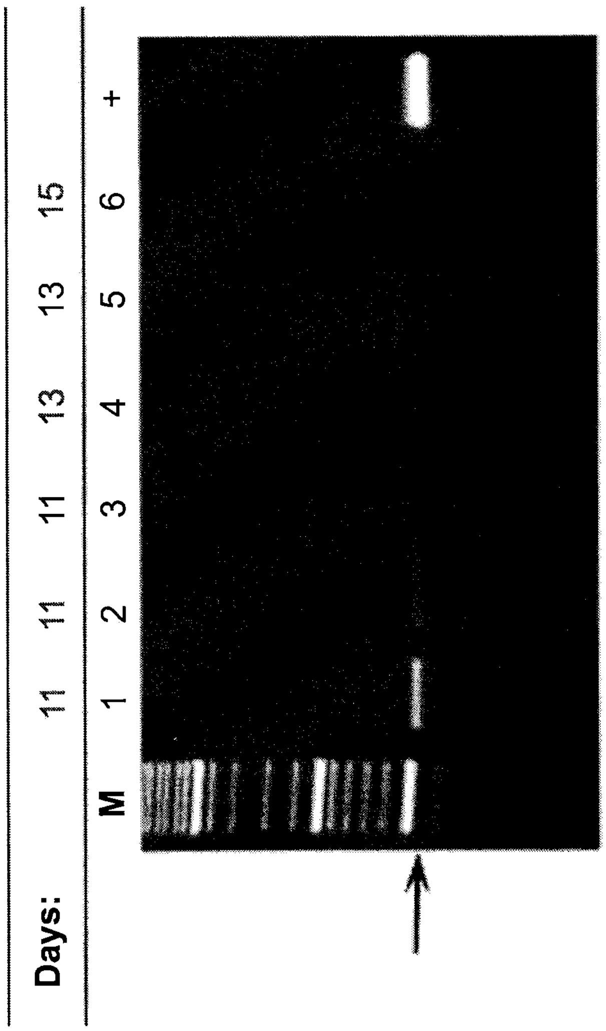
FIG. 3 is a photograph illustrating the results of RT-PCR analysis of *Varroa*-extracted RNA at the days indicated in the top row (time as indicated in FIG. 1). Green numbers (top row) indicate *Varroa* individuals which had been placed on dsRNA-GFP-ingested bees and black numbers indicate RNA from *Varroa* placed on control bees. +=positive control (a GFP-carrying plasmid).

*Varroa* individuals were placed on adult bees that had been fed for 7 days with dsRNA-GFP and on control (unfed) bees. RNA was extracted from *Varroa* at the indicated times (FIG. 1) and subjected to RT-PCR with GFP primers. The results are illustrated in FIG. 3.

Bees were fed with a segment of dsRNA for apoptosis inhibitor (IAP) gene (SEQ ID NO: 27). *Varroa* collected from that hive were analyzed by RT-PCR for the expression of the IAP gene (FIG. 4).

Example 2

Materials and Methods

Hives were fed by two different mixtures of dsRNAs corresponding to *Varroa* gene segments. All dsRNA were corresponding to gene segments that are not homologous to bee or human sequences (not carrying stretches of homologous sequences longer than 19 bases). Mixture I (Minimum treatment) contained SEQ ID NOs: 1, 13, 27, 30 and 39. Mixture II (Maximum treatment) contained SEQ ID NOs: 1, 4, 7, 10, 13, 16, 19, 22, 25, 27, 30, 33, 36 and 39. Thirty *Varroa* individuals were placed in each hive and two months later *Varroa* and bees were counted in each hive. Each treatment was repeated 3 times.

Results

No visible damage to the strength of the hive was noticed among the various hives. FIG. 5 demonstrates the reduction of *Varroa* population following treatment with dsRNAs of *Varroa*'s gene sequences.

Example 3

Large-Scale Field Trials of *Varroa*-Specific dsRNA for Prevention of *Varroa* Mite-Associated Disease of Honeybees In order to determine the effectiveness of ingested *Varroa* mite dsRNA on *Varroa* mite infestation under actual field conditions, and to assess effects on important parameters of colony health, bees in sample full size hives are provided with *Varroa* mite-specific dsRNA in the feed for 5 days before, and 4 days following infestation with *Varroa* mite.

Materials and Methods

Insect Material:

Pools of five bees from the following treatments; Remote control, *Varroa* mite-dsRNA only, *Varroa* mite only and *Varroa* mite-specific dsRNA+ *Varroa* mite at each time point day 0-(day of virus application), day 7 and end point (day 42). The test was repeated several times.

RNA Extraction:

RNA is extracted using Tri-Reagent (Sigma, USA) according to protocol provided by the manufacturer. All samples are treated with DNaseI and resuspended with loading buffer (90% Formamide, 0.05 Bromophenol Blue, 0.05% Xylene cyanol) prior to loading on gel.

Gel Electrophoresis and Blot:

10 μg of freshly prepared RNA is measured using the nanodrop spectrophotometer and loaded on 12% Acrylamide gel (1:19 acrylamide:Bis acrylamide ratio) in denturation environment (gel contains 7M Urea). After electrophoresis samples are transferred to positively charged nylon membrane (Roch, USA) using electroblotting method.

Hybridization and Signal Detection:

Membrane is hybridized with freshly prepared DNA probe of *Varroa* mite segment, taken from a region that does not correspond to the dsRNA of the *Varroa* mite-specific dsRNA itself. This is made using DIG PCR probe preparation Kit (Roch, USA) o/n 42° C. in DIG easyhyb solution (Roch, USA) according to manufacturer protocol. The membrane is washed twice with 2×SSC/0.1 SDS, than washed for stringency with 0.1×SSC/0.1% SDS in 65° C. Membranes are further washed using DIG Wash and Block Kit (Roch, USA) according to manufacturer protocol. Detection is preformed using CSPD-star substrate (Roch, USA). Positive control is 21nt DNA primers corresponding to the hybridized sequence.

Signal is detected using membrane exposure for 2-12 hours in chemiluminator manufactured by Kodak.

Basic parameters of bee colony health (numbers of capped brood, numbers of bees in the hive, returning foragers and honey production) are assessed in hives fed *Varroa* mite-dsRNA and control hives, in the absence of *Varroa* mite infestation.

Example 4

Bi-Directional Transfer of Bee-Ingested dsRNA from Bee to *Varroa* Mite and Back to Bee Via *Varroa* Infestation In Examples 1 and 2 it was shown that dsRNA can be transferred from bees to *Varroa* directly into mites infesting bees ingesting the dsRNA, or indirectly into mites infesting larva fed by bees which ingested the dsRNA. In order to uncover whether the mites can further serve as an additional vector, transferring the dsRNA or siRNA from the mite back to a "naïve" bee via parasitisation, "naïve" bees were infested with *Varroa* following infestation of dsRNA-fed bees.

Materials and Methods dsRNA Preparation:

*Varroa*-specific and GFP dsRNA was prepared from sequences cloned into plasmids between opposing T7 promoters, as described in Example 1. Segments of selected *Varroa* genes, 200 to 450 bp in length, which did not correspond in sequence to any bee or human genes (identity of less than 21 consecutive bases), were selected for *Varroa* dsRNA production. Table I below details the sequences of the primers used for preparation of the dsRNA, and the length of the amplicon, excluding the T7 promoter sequence

TABLE I

Primers for dsRNA preparation

| Varroa-specific dsRNA SEQUENCE (SEQ ID NO:) | Primers (F = Forward; R = Reverse) /SEQ ID NO: | Amplicon (bp) |
|---|---|---|
| SEQ ID NO: 93 | F: 5' C**TAATACGACTCACTATAGGGCGA**ATGGAGAACATCGCACAG3'/SEQ ID NO: 107 | 411 bp |
| | R: 5' C**TAATACGACTCACTATAGGGCGA**TTCCAGTACGTTATGTTGCTC3'/SEQ ID NO: 108 | |
| SEQ ID NO: 94 | F: 5' C**TAATACGACTCACTATAGGGCGA**GGTCTTGACAACACATGCTAC 3'/SEQ ID NO: 109 | 277 bp |
| | R: 5' C**TAATACGACTCACTATAGGGCGA**CTCAGCAGAAATGATCGG3'/SEQ ID NO: 110 | |
| SEQ ID NO: 95 | F: 5' C**TAATACGACTCACTATAGGGCGA**AACGCTGTGCTTCACGTA 3'/SEQ ID NO: 111 | 329 bp |
| | R: 5' C**TAATACGACTCACTATAGGGCGA**TCACGAGTAATCTCCACGA 3'/SEQ ID NO: 112 | |
| SEQ ID NO: 96 | F: 5' C**TAATACGACTCACTATAGGGCGA**TCAGATGATTGGAACGGA 3'/SEQ ID NO: 113 | 380 bp |
| | R: 5' C**TAATACGACTCACTATAGGGCGA**AACAGGTCTTCAAACAGCAG 3'/SEQ ID NO: 114 | |
| SEQ ID NO: 97 | F: 5' C**TAATACGACTCACTATAGGGCGA**TCAATTCGTCTGCAGATCTC 3'/SEQ ID NO: 115 | 426 bp |
| | R: 5' C**TAATACGACTCACTATAGGGCGA**CATAAATGGCGATAAGCG 3'/SEQ ID NO: 116 | |
| SEQ ID NO: 98 | F: 5' C**TAATACGACTCACTATAGGGCGA**AATGAGTGTTGAGCGCGG 3'/SEQ ID NO: 117 | 366 bp |
| | R: 5' C**TAATACGACTCACTATAGGGCGA**CTCCGATCATTTGGCGTT 3'/SEQ ID NO: 118 | |
| SEQ ID NO: 99 | F: 5' C**TAATACGACTCACTATAGGGCGA**AGGTGACATCCGTGTTCG 3'/SEQ ID NO: 119 | 324 bp |
| | R: 5' C**TAATACGACTCACTATAGGGCGA**ATGAAGACATATAGGGTCGCT 3'/SEQ ID NO: 120 | |
| SEQ ID NO: 100 | F: 5' C**TAATACGACTCACTATAGGGCGA**CTGTACAGGGTCCGAATATAAA 3'/SEQ ID NO: 121 | 311 bp |
| | R: 5' C**TAATACGACTCACTATAGGGCGA**TTCGAGTTICTCAAAGGITG 3'/SEQ ID NO: 122 | |

TABLE I-continued

| Primers for dsRNA preparation | | |
|---|---|---|
| Varroa-specific dsRNA SEQUENCE (SEQ ID NO:) | Primers (F = Forward; R = Reverse) /SEQ ID NO: | Amplicon (bp) |
| SEQ ID NO: 101 | F: 5' C**TAATACGACTCACTATAGGGCGA**CAATTGAATATGGACGTCACTC 3'/SEQ ID NO: 123 | 201 bp |
| | R: 5' C**TAATACGACTCACTATAGGGCGA**TTGAAAGCCAGCAGTAAACG 3'/SEQ ID NO: 124 | |
| SEQ ID NO: 102 | F: 5' C**TAATACGACTCACTATAGGGCGA**CATCATCTTCTTCATCTGCTTG 3'/SEQ ID NO: 125 | 290 bp |
| | R: 5' C**TAATACGACTCACTATAGGGCGA**GGTTCCCACGGTTGGTAT 3'/SEQ ID NO: 126 | |
| SEQ ID NO: 103 | F: 5' C**TAATACGACTCACTATAGGGCGA**AATGGTTTCTGCTACCTGTG 3'/SEQ ID NO: 127 | 263 bp |
| | R: 5' C**TAATACGACTCACTATAGGGCGA**ATTGGAAGCTGATACATTGG 3'/SEQ ID NO: 128 | |
| SEQ ID NO: 104 | F: 5' C**TAATACGACTCACTATAGGGCGA**TGGCTAATTAATAGTAGGCCG 3'/SEQ ID NO: 129 | 277 bp |
| | R: 5' C**TAATACGACTCACTATAGGGCGA**TGGAGTTTGCTACCAACCT 3'/SEQ ID NO: 130 | |
| SEQ ID NO: 105 | F: 5' C**TAATACGACTCACTATAGGGCGA**AGCCGGCTTCTTCTTCCT 3'/SEQ ID NO: 131 | 263 bp |
| | R: 5' C**TAATACGACTCACTATAGGGCGA**AGTCACTGCCTGTTCCTCC 3'/SEQ ID NO: 132 | |
| SEQ ID NO: 106 | F: 5' C**TAATACGACTCACTATAGGGCGA**TTCCGCTTCATTTGAGAAC 3'/SEQ ID NO: 133 | 282 bp |
| | R: 5' C**TAATACGACTCACTATAGGGCGA**TCTGAATCAACCTCATCGG 3'/SEQ ID NO: 134 | |
| SEQ ID NO: 92 | F: 5' **TAATACGACTCACTATAGGGCGA**GCCAACACTTGTCACTACTAGAAAGAGAA 3'/SEQ ID NO: 135 | 431 bp |
| | R: 5' **TAATACGACTCACTATAGGGCGA**AGGTAATGGITGTCTGGTAAAGGAC 3'/SEQ ID NO: 136 | |

RNA Extraction and Analysis:

Total RNA for dsRNA-GFP detection experiments was isolated from a single honeybee or from 10 *Varroa* mites, using phenol-chloroform extraction (peqGOLD Trifast™, Peqlab). Total RNA for *Varroa* dsRNA experiments was isolated from 5 *Varroa* mites by tissue homogenization binding to a mini-column, DNA-removal and RNA elution (ZR Tissue & Insect RNA MicroPrep, Zymo Research, Irvine Calif.). DNA was digested in the eluted RNA by nucleases (TURBO DNA-free kit, Ambion, Austin, Tex., USA) and the RNA was tested for DNA contamination. *Varroa* RNA was then co-precipitated with glycogen and 3 M sodium acetate in 70% ethanol and resuspended in 20 μl of RNAse-free water. The amount and quality of the RNA were determined spectrophotometrically using the nanodrop method (NanoDrop Technologies, Wilmington, Del., USA).

dsRNA-GFP Detection by RT-PCR:

dsRNA-GFP was detected by RT-PCR using Verso 1-Step RT-PCR (Thermo Scientific) with specific GFP primers (SEQ ID NOs. 135 and 136) using total RNA extracted from 10 *Varroa* or 1 honeybee as template.

Gene Expression: Real-Time RT-PCR and Semi-Quantitative RT-PCR:

RNA (400 ng) was subjected to reverse transcription with random hexamers (Verso cDNA kit, Thermo Scientific, Waltham Mass.). Each sample of the obtained cDNA was diluted 1:50 before amplification. Real-time quantitative PCR was performed by LightCycler 480 (Roche, Indianapolis, Ind.) and results analyzed with the instrument's software. Primers and probes were as detailed in Table II.

TABLE II

List of primers and probes used for real-time and semi-quantitative RT-PCR assays.

| Sequence (SEQ ID NO) | Primers/SEQ ID NO: | Amplicon (bp) |
|---|---|---|
| Varroa RNA Polymerase III (SEQ ID NO: 96) | F: 5' AAAGGGCAGGTGCTTATCAA 3'/137<br>R: 5' TGTCCAGGGTCGAGAGTAGC 3'/138 | 65 |
| Varroa vacuolar proton ATPase (SEQ ID NO: 101) | F: 5' ACCTTTTTCAAAGACCGAACC 3'/139<br>R: 5' CGAAGACTCCGTTCGAAAAC 3'/140 | 62 |
| Varroa IAP1 and IAP2, reverse (SEQ ID NO: 106) | F: 5' CTAGTTAATGGCGCGGTAGC 3'/141<br>R: 5' TCCTCCCGGTTCTACTTCAC 3'/142 | 63 |

TABLE II-continued

List of primers and probes used for real-time and semi-quantitative RT-PCR assays.

| Sequence (SEQ ID NO) | Primers/SEQ ID NO: | Amplicon (bp) |
|---|---|---|
| Varroa 18S RNA | F: 5' AATGCCATCATTACCATCCTG 3'/143<br>R: 5' CAAAAACCAATCGGCAATCT 3'/144 | 60 |
| Varroa Apoptosis Inhibitor FAS (SEQ ID NO: 104) | F: 5' ATCTGCCCACGTCAGCGTTT 3'/145<br>R: 5' GTCCGTCATTTCGGCTTTGG 3'/146 | 317 |
| Varroa Actin | F: 5' AAGTCGTACGAGCTTCCCGAC 3'/147<br>R: 5' ACAGGGAGGCAAGGATGGAAC 3'/148 | 336 |

The real-time PCR program was as follows: 95° C. for 10 min, followed by 45 cycles of 95° C. for 10 seconds and 60° C. for 30 seconds, and finally 40° C. for 30 seconds. 18S rRNA was used as an internal control for the standardization of RNA levels.

The semi-quantitative PCR program was as follows: 95° C. for 10 min, followed by 40 cycles, each consisting of 95° C. for 10 seconds and 65° C. and 55° C. for 30 seconds for the apoptosis inhibitor (FAS, primers were SEQ ID Nos. 145 and 146) and its internal standardization control (actin, primers were SEQ ID Nos. 147 and 148), respectively, followed by 72° C. for 30 seconds. Reaction products were sampled every three cycles starting from cycle 31 for FAS and from cycle 29 for actin, the sample incubated for 5 min at 72° C. and stored at −20° C. Samples were analyzed on a 1.2% agarose gel. Each semi-quantitative PCR experiment was repeated three times.

Regimen of dsRNA-GFP Feeding:

1-day-old bees were placed in four plastic containers (30 bees per container). Two containers were fed with 30 μg dsRNA-GFP in 200 μl of 50% sucrose solution for 8 days, and the other two control containers fed 50% sucrose solution without dsRNA. Mite infestation was initiated by introduction of adult female *Varroa* (n=30) into each container on day 5. After 3 days, *Varroa* that were attached to bees were removed and collected, and their RNA isolated for dsRNA-GFP analysis. To test for bidirectional transfer of dsRNA-GFP from bee to mite and on to another bee, newly emerged, untreated bees were infested by some of the *Varroa* that had been detached from the dsRNA-fed bees for 4 days and the bee's RNA isolated for dsRNA-GFP analysis. Each day, bees in all containers were given an additional 1 ml sucrose solution after finishing their treatment. In addition, bees had free access to a pollen patty consisting of 70% pollen mixed with sugar powder.

To test for indirect transfer of dsRNA-GFP from adult bee to bee larva and on to mite feeding on the hemolymph of the developing bee in a sealed cell, a cup of bees (about 250) and a laying queen were introduced into each mini-hive (two repetitions in each of two enclosures). dsRNA-GFP (200 μg per hive) was provided daily in 5 ml 50% sucrose solution for 8 days. Thirty *Varroa* mites were introduced to the hives on the fifth day. Adult female *Varroa* were collected from sealed cells from day 11 till day 30 and their RNA was isolated for dsRNA-GFP analysis.

Figure 8:
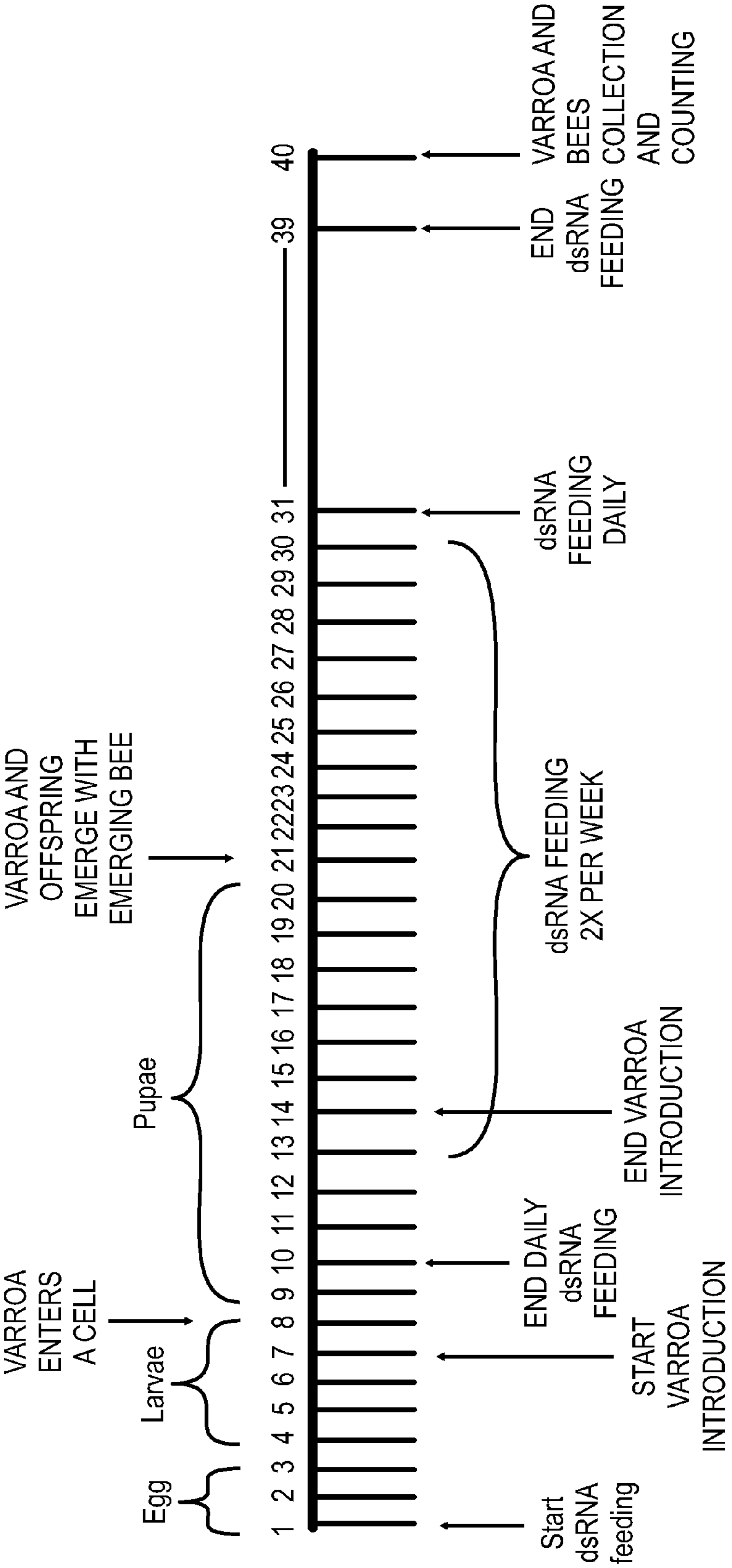
FIG. 8 is a schematic representation of a 60-day feeding experiment for *Varroa*-specific dsRNA, including honeybee feeding regimen and testing schedule for *Varroa* gene expression (bottom) and the honeybee feeding *Varroa* mite life cycle.
Figures 9A, 9B, 9C, 9D, 9E, 9F:
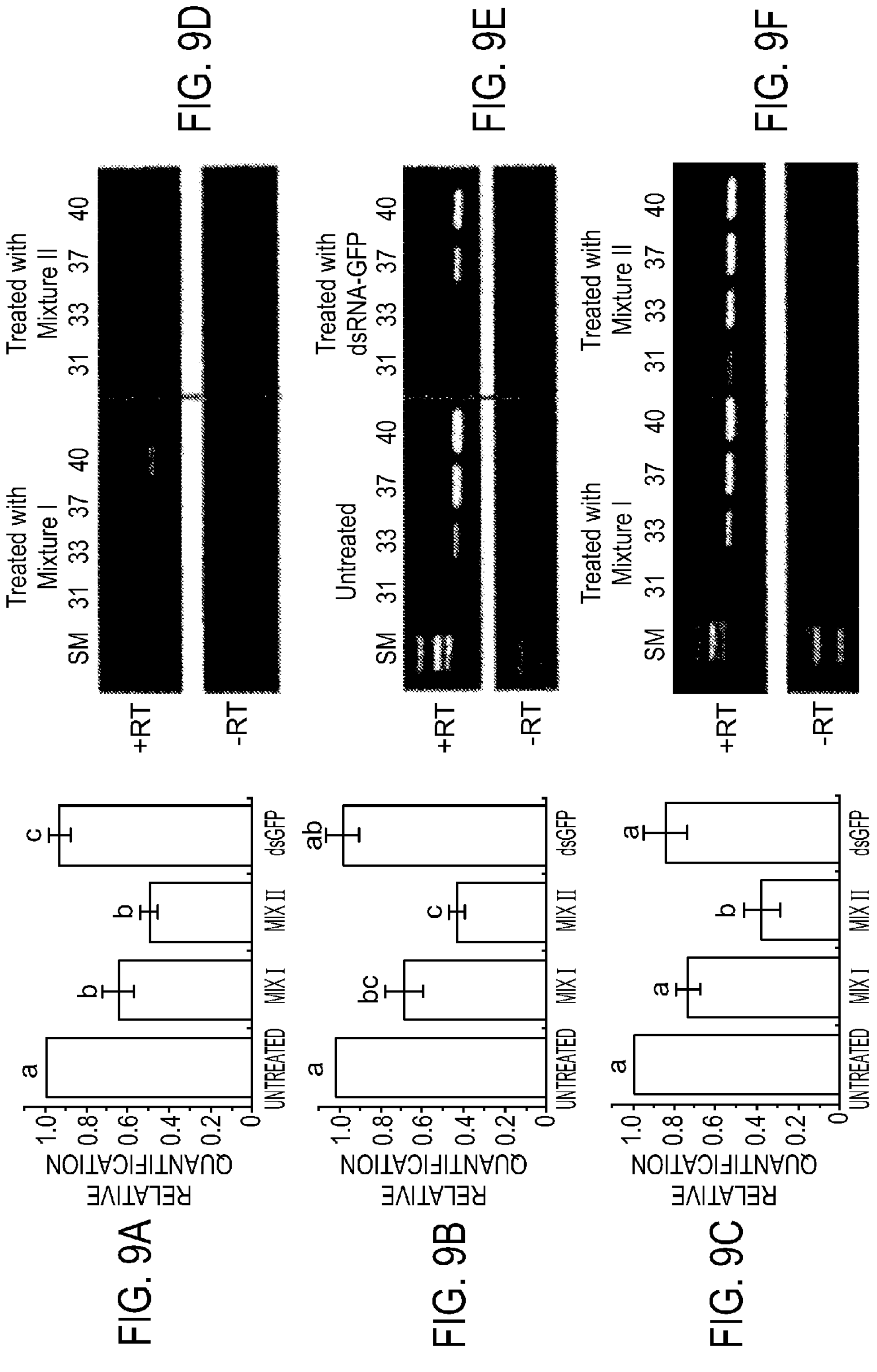
FIGS. 9A-9F illustrate silencing of *Varroa* gene expression following horizontal transfer of *Varroa*-specific dsRNA from bee to *Varroa* mite.

Feeding *Varroa*-Specific dsRNA Sequences:

The experiment with *Varroa* dsRNA was conducted in mini-hives, 12 mini-hives per repetition, for three repetitions. In each repetition, a cup of bees and a laying queen were placed in each mini-hive. Three mini-hives were randomly assigned to one of four netted enclosures, each representing a different feeding treatment. Bees were fed 5 ml of 50% sucrose solution in troughs placed in each mini-hive. The four treatments were: 1) sucrose solution only (untreated control), 2) Mixture I (200 μg each of five dsRNAs added to the sugar solution), 3) Mixture II (200 μg each of 14 dsRNAs added to the sugar solution), and 4) dsRNA-GFP (200 μg dsRNA) serving as a dsRNA-positive control. Bees that fully consumed the treatment solutions were supplemented with candy (67% sugar powder and 33% honey). In addition, the bees were routinely fed pollen patties (70% pollen and 30% sugar powder). Each repetition of the experiment lasted for 60 days (FIG. 8). Bees in each treatment were fed the respective solution daily for the first 10 days and for the last 14 days, and twice a week in the interim. Infestation with *Varroa* mites was initiated by introducing mites into each mini-hive from day 7 until day 14. In the first repetition, 30 mites were introduced into each mini-hive; in the latter two repetitions, 100 mites were introduced into each mini-hive. On day 60, all mature bees were collected, counted and shaken with 70% ethanol overnight in order to collect and count *Varroa* mites falling off the bees. All capped brood cells were opened to collect and count *Varroa* mites. Number of mites per bee included mature and developing (capped brood) bees. *Varroa* mites, adult bees, emerging bees and pupae were stored for molecular analyses.

Statistical Analysis:

Statistical analyses were conducted with JMP statistical software version 9 (SAS Institute, Cary, N.C., USA). Statistical significance was set at $P<0.05$. To test for significant differences in relative expression, one-way ANOVA was conducted on ddCt values. Treatment was the main factor. To test for differences in *Varroa* mite population, two-way ANOVA was conducted on numbers of *Varroa* per bee in a block design with treatment as main effect and experimental replicate as block. To test for differences in total bee population, a similar two-way ANOVA was conducted on the total number of bees (capped brood and adults). Significant differences between treatments were tested by the Tukey-Kramer (HSD) test.

Results

Direct and Indirect Horizontal Transfer of dsRNA Between Bees and *Varroa* Mites:

As shown in Examples 1 and 2, bees fed with dsRNA can transfer dsRNA sequences to *Varroa* mites via infestation, and to bee larva and pupae via feeding by dsRNA-bearing bees.

Figure 6:
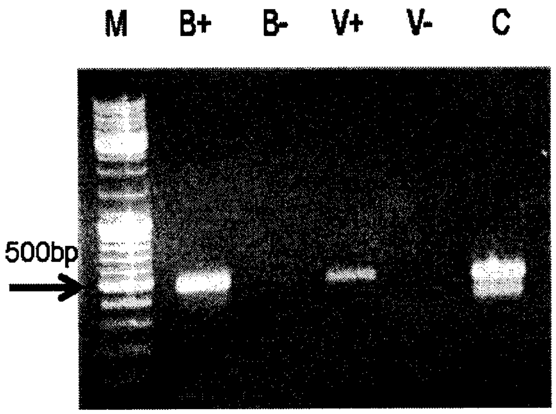
FIG. 6 is a photograph illustrating dsRNA transmission from adult bees to *Varroa* mites. RT-PCR was performed on RNA from bees fed with GFP-specific dsRNA and untreated control bees (lanes B+, B−, respectively) and RNA from *Varroa* mites parasitizing the treated or untreated control bees (lanes V+ and V−, respectively). Lane C: Positive control (GFP-bearing plasmid). M=size markers.
Figure 7:
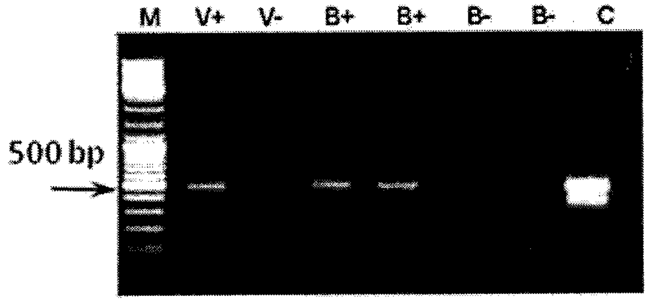
FIG. 7 is a photograph illustrating dsRNA transmission from bees to *Varroa* and *Varroa* back to bees. Bees were infested with either *Varroa* mites carrying the GFP dsRNA or siRNA(V+) or control mites (V) devoid of GFP-specific dsRNA or siRNA. B+ is RNA amplified from bees infested with GFP-dsRNA or siRNA-fed mites, B− is RNA amplified from bees infested with control mites devoid of GFP-specific dsRNA or siRNA. Lane C: Positive control (GFP-bearing plasmid). M=size markers.

Direct transfer of GFP-specific sequences from adult bees fed with dsRNA-GFP in a 50% sucrose solution for 8 days to *Varroa* mites via infestation on the fifth day of feeding was verified by RT-PCR of the mite RNA after 3 days of infestation (FIG. 6, see lanes B+ and V+).

Indirect horizontal transfer of GFP-specific sequences from bees to mites via larva/pupae was verified by detection, by PCR, of GFP-specific sequences in *Varroa* RNA collected from mites feeding on larval/pupae fed by nurse bees ingesting GFP-specific dsRNA-containing sugar solution (results not shown).

To test for bidirectional horizontal transfer, mites feeding on bees ingesting GFP-specific dsRNA were removed from the bees after 3 days and introduced into a container with untreated, "naïve" bees for 4 days. RT-PCR of *Varroa* and bee RNA reveals that GFP-specific RNA sequences were detectable in RNA extracts of "naïve" bees which had been parasitized by *Varroa* mites previously infesting bees carrying GFP-dsRNA (see FIG. 7, lanes B− and B+). The presence of GFP-specific sequences in the parasitized "naïve" bees indicates reciprocal, bi-directional transfer of the GFP-specific sequences derived from dsRNA, from bee to *Varroa* and then to another bee by mite infestation.

These results clearly point to a surprising additional means for transmission, from dsRNA-fed bees to mites and back to "naïve" bees, of RNAi sequences derived from the dsRNA. Such bi-directional transmission can be effective in further disseminating the silencing effect of ectoparasite (e.g. mite)-specific dsRNA fed to bees.

Example 5

Silencing of *Varroa* Gene Expression Mediated by Bees Ingesting dsRNA

Specific silencing of *Varroa* gene expression via feeding of dsRNA to the bees was tested in mini-hives consisting of about 250 worker bees and a laying queen. Minihives were provided with bee feed (sucrose solution) with either one of two mixtures of the *Varroa* dsRNA: Mixture I contained sequences derived from five *Varroa* gene sequences (SEQ ID NOs. 93, 96, 100, 104 and 106) or Mixture II contained 14 *Varroa* gene sequences (SEQ ID NOs. 93-106). Note that sequence represented by SEQ ID NO: 101 does not appear in Mixture I. Controls were mini-hives fed with an irrelevant dsRNA (dsGFP) or only sucrose solution.

*Varroa* mites were introduced following 1 week of feeding, the mites added every day for a week (see protocol in FIG. 8). At the end of 60 days *Varroa* mites were samples from all four treatment groups, and transcription levels of four selected *Varroa* genes determined by real-time or semi-quantitative RT-PCR, as described in Example 4.

Results

Real-Time PCR of *Varroa* RNA (FIGS. 9A-9C) clearly indicates approximately 35 to 60% reduction in expression of three representative *Varroa*-specific genes (RNA polymerase III, 9A; IAP1 and IAP2, 9B and Vacuolar proton ATPase, 9C) resulting from feeding the bees *Varroa*-specific dsRNA. Semi-quantitative PCR of *Varroa* RNA (FIG. 9D) illustrates even more dramatic, potentially disruptive silencing of *Varroa* apoptosis-inhibiting FAS gene expression by feeding bees apoptosis inhibitor FAS-specific dsRNA, in a highly specific manner (see FIGS. 9E and 9F).

Effect of Gene Silencing of *Varroa* Gene Expression on *Varroa* Infestation in Hives:

Following detecting the silencing of several *Varroa* genes, the effect on mite infestation was investigated.

Figure 10:
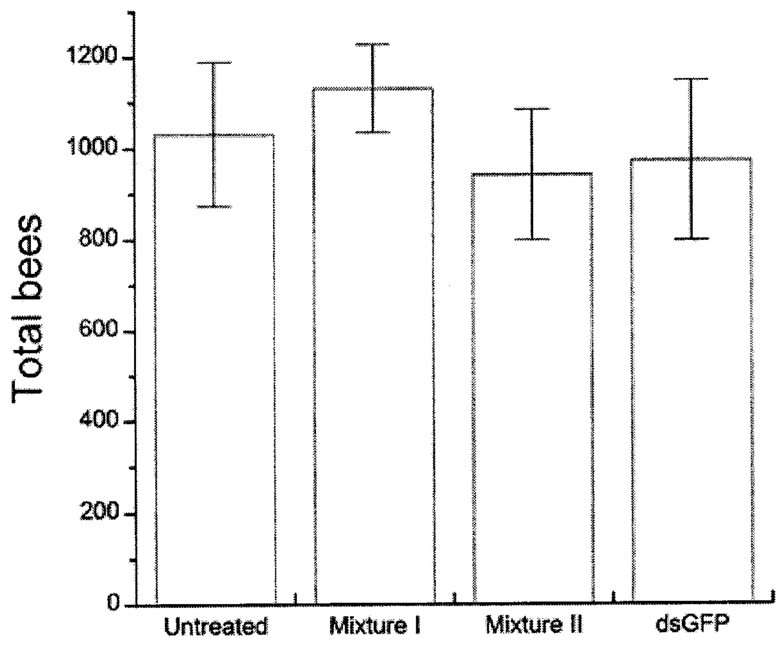
FIG. 10 is a graph showing the mean (±SE) total number of bees (capped brood and adults) in bees fed a mixture of 5 *Varroa*-specific dsRNAs (Mixture I) or a mixture of 14 *Varroa*-specific dsRNAs (Mixture II), or control bees fed irrelevant (dsGFP) dsRNA or untreated (Untreated). No significant differences were detected.

In order to determine whether feeding the dsRNA mixtures affected bee survival, all mature bees and sealed brood in the mini-hives at completion of the protocol (see FIG. 8) were counted. Bee population size did not differ between control and dsRNA-treated mini-hives ($F_{3,29}$=0.62, P=0.608; FIG. 10). The results were similar when brood and adult bees were analyzed separately (not shown). Thus, feeding the dsRNA mixtures is not deleterious to bees, indicating no off-target effect of the feeding.

In order to determine whether bee-mediated silencing of *Varroa* genes could be employed for control of mite infestation in hives, the number of *Varroa* individuals per bee was determined by actual examination of the mite population on mature bees and in sealed brood cells at the completion of the protocol.

*Varroa* infestation was reduced in bees of mini-hives fed with *Varroa* dsRNA compared to the controls ($F_{3,29}$=5.65, P=0.0035; FIG. 11). The effect was even more significant in bees of hives fed Mixture II, which targeted more genes than Mixture I, reducing *Varroa* infestation by an average 53% compared to control hives fed the dsRNA-GFP control, and by 61% compared to hives receiving no dsRNA control.

Taken together, these results indicate that feeding bees *Varroa*-specific dsRNA results in both direct and indirect transmission of mite-specific dsRNA and siRNA to mites feeding off the bees and larval/pupae in the hives, as well as bi-directional transmission of the *Varroa*-specific RNA sequences from parasitizing mites back to "naïve" bees, and that feeding the *Varroa*-specific dsRNA is an effective and safe method for reducing mite infestation in the hives.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of providing a nucleic acid agent to a *Varroa destructor* mite, comprising feeding a bee parasitized by the *Varroa destructor* mite a bee-ingestible composition comprising the nucleic acid agent, wherein the nucleic acid agent is double stranded RNA (dsRNA) comprising a nucleic acid sequence complementary to at least 21 nucleotides of *Varroa destructor* mite mRNA.

2. The method of claim 1, wherein the nucleic acid agent down-regulates expression of a gene product of the *Varroa destructor* mite.

3. The method of claim 1, wherein the bee-ingestible composition is selected from the group consisting of a liquid bee-ingestible composition and a solid bee-ingestible composition.

4. The method of claim 1, wherein the bee is in the larval stage.

5. The method of claim 1, wherein the bee is an adult.

6. The method of claim 1, wherein the bee-ingestible composition comprises protein.

7. The method of claim 1, wherein the bee-ingestible composition comprises pollen.

8. The method of claim 1, wherein the bee-ingestible composition comprises a carbohydrate.

9. The method of claim 8, wherein the carbohydrate is selected from the group consisting of sucrose and corn syrup.

10. The method of claim 1, wherein the *Varroa destructor* mite mRNA encodes a polypeptide selected from the group consisting of ATPase subunit A, RNA polymerase I, RNA polymerase III, Inhibitor of apoptosis (IAP), FAS apoptotic inhibitor and α-Tubulin.

11. A method of down-regulating expression of a gene product in a *Varroa destructor* mite, the method comprising administering a double stranded RNA (dsRNA) comprising a nucleic acid sequence complementary to at least 21 nucleotides of *Varroa destructor* mite mRNA of said gene product to a bee parasitized by the *Varroa destructor* mite, wherein an RNA silencing agent complementary to said nucleic acid sequence is provided to the *Varroa destructor* mite in the bee's hemolymph and downregulates expression of the gene product in the *Varroa destructor* mite.

12. The method of claim 11, wherein the bee is in the larval stage.

13. The method of claim 11, wherein the bee is an adult.

14. The method of claim 11, wherein the dsRNA is administered to the bee by feeding the bee a bee-ingestible composition comprising the dsRNA.

15. The method of claim 14, wherein the bee-ingestible composition is selected from the group consisting of a liquid bee-ingestible composition and a solid bee-ingestible composition.

16. The method of claim 15, wherein the bee-ingestible composition comprises one or more of a protein and a carbohydrate.

17. The method of claim 16, wherein the carbohydrate is selected from the group consisting of sucrose and corn syrup.

18. The method of claim 11, wherein the *Varroa destructor* mite mRNA encodes a polypeptide selected from the group consisting of ATPase subunit A, RNA polymerase I, RNA polymerase III, Inhibitor of apoptosis (IAP), FAS apoptotic inhibitor and α-Tubulin.

* * * * *

SEQUENCE LISTING

<160> NUMBER OF SEQ ID NOS: 148

<210> SEQ ID NO 1
<211> LENGTH: 371
<212> TYPE: DNA
<213> ORGANISM: Varroa destructor

<400> SEQUENCE: 1
gttagccgtc tgaagcaatg cttgactgta cagggtccga atataaaact tcatacattc 60
aaaatcacgt atcaggatta tgctaaacat cgcaccataa aaatcttcac taaagttatt 120
ttacgcttca ggatagtggt ccgttatgag tgttgcggta ttagtgcgtt tacaaatttg 180
ctaacgatat taacaagctt atttcactcg ttggcaggtt ttctagaacg cgaggtgagg 240
aaggataacc ttccgatgat gtcattcggc gacaatcctg aggcgcctca gcctcgggag 300
atgattgatc tagaagcaac ctttgagaaa ctcgaaaacg aactcaatga ggtagttttc 360
tgtgttgaaa t 371

<210> SEQ ID NO 2
<211> LENGTH: 313
<212> TYPE: DNA
<213> ORGANISM: Varroa destructor

<400> SEQUENCE: 2
ctgtacaggg tccgaatata aaacttcata cattcaaaat cacgtatcag gattatgcta 60
aacatcgcac cataaaaatc ttcactaaag ttattttacg cttcaggata gtggtccgtt 120
atgagtgttg cggtattagt gcgtttacag atttgctaac gttattaaca agctaatttc 180
actcgttggc aggttttcta gaacgcgagg tgaggaagga taaccttccg atgatgtcat 240
tcggcgacaa tcctgaggcg cctcagcctc gggagatgat tgatctagaa gcaacctttg 300
agaaactcga aaa 313

<210> SEQ ID NO 3
<211> LENGTH: 304
<212> TYPE: DNA
<213> ORGANISM: Varroa destructor

<400> SEQUENCE: 3
ttcgagtttc tcaaaggttg cttctagatc aatcatctcc cgaggctgag gcgcctcagg 60
attgtcgccg aatgacatca tcggaaggtt atccttcctc acctcgcgtt ctagaaaacc 120
tgccaacgag tgaaattagc ttgttaataa cgttagcaaa tctgtaaacg cactaatacc 180
gcaacactca taacggacca ctatcctgaa gcgtaaaata actttagtga agatttttat 240
ggtgcgatgt ttagcataat cctgatacgt gattttgaat gtatgaagtt ttatattcgg 300
accc 304

<210> SEQ ID NO 4
<211> LENGTH: 242
<212> TYPE: DNA
<213> ORGANISM: Varroa destructor

<400> SEQUENCE: 4
caactcatta aaatgaaatc agtattccac atcatgaatc aattgaatat ggacgtcact 60
cagaagtgtc ttattgccga atgctggatt cctgatcgcg atgtagcaaa ggtacaagct 120
gccctgcgac gtggaacgga agcggctgga agcagcttcc cgtgtatcat taaccggttg 180
gaaacggacc aagctccacc gacgttctac agaacgaact cgtttactgc tggctttcaa 240
aa 242

<210> SEQ ID NO 5
<211> LENGTH: 213
<212> TYPE: DNA

-continued

<213> ORGANISM: Varroa destructor

<400> SEQUENCE: 5
caattcgtga ttcaattgaa tatggacgtc actcagaagt gtcttattgc cgaatgctgg 60
attcctgatc gcgatgtagc aaaggtacaa gctgccctgc gacgtggaac ggaagcggct 120
ggaagcagct tcccgtgtat cattaaccgg ttggaaacgg acaaagctcc accgacgttc 180
tacagaacga actcgtttac tgctggcttt caa 213

<210> SEQ ID NO 6
<211> LENGTH: 201
<212> TYPE: DNA
<213> ORGANISM: Varroa destructor

<400> SEQUENCE: 6
caattgaata tggacgtcac tcagaagtgt cttattgccg aatgctggat tcctgatcgc 60
gatgtagcaa aggtacaagc tgccctgcga cgtggaacgg aagcggctgg aagcagcttc 120
ccgtgtatca ttaaccggtt ggaaacggac aaagctccac cgacgttcta cagaacgaac 180
tcgtttattg ctggctttca a 201

<210> SEQ ID NO 7
<211> LENGTH: 307
<212> TYPE: DNA
<213> ORGANISM: Varroa destructor

<400> SEQUENCE: 7
aatcacaatt ttctacatca tcttcttcat ctgcttggcg gcattctgga cggttatgct 60
ggtcatcttc tatcagacac tcgatgcctt ccagccaaag tggaccctgg acgctagtct 120
cattggcact gtaccgggat taggcttcag gccacgccca ccgctgtcta acatcgactc 180
aacactcatc tatttcaagg tatctaagcc gttagtgtat atgttatatt atagcgctct 240
ttgttatgtg gaaagacgcc agggcgcgta tctatatggt ggttttcata ccaaccgtgg 300
gaaccca 307

<210> SEQ ID NO 8
<211> LENGTH: 290
<212> TYPE: DNA
<213> ORGANISM: Varroa destructor

<400> SEQUENCE: 8
ggttcccacg gttggtatga aaaccaccat atagatacgc gccctggcgt ctttccacat 60
aacaaagagc gctataatat aacatataca ctaacggctt agataccttg aaatagatga 120
gtgttgagtc gatgttagac agcggtgggc gtggcctgaa gcctaatccc ggtacagtgc 180
caatgagact agcgtccagg gtccactttg gctggaaggc atcgagtgtc tgatagaaga 240
tgaccagcat aaccgtccag aatgccgcca agcagatgaa gaagatgatg 290

<210> SEQ ID NO 9
<211> LENGTH: 290
<212> TYPE: DNA
<213> ORGANISM: Varroa destructor

<400> SEQUENCE: 9
catcatcttc ttcatctgct tggcggcatt ctggacggtt atgctggtca tcttctatca 60
gacactcgat gccttccagc caaagtggac cctggacgct agtctcattg gcactgtacc 120
gggattaggc ttcaggccac gcccaccgct gtctaacatc gactcaacac tcatctattt 180
caaggtatct aagccgttag tgtatatgtt atattatagc gctctttgtt atgtggaaag 240
acgccagggc gcgtatctat atggtggttt tcataccaac cgtgggaacc 290

<210> SEQ ID NO 10
<211> LENGTH: 357
<212> TYPE: DNA
<213> ORGANISM: Varroa destructor

<400> SEQUENCE: 10
gaggtgacat ccgtgttcgc cgtgtacggc atcaaagtgg atccaagaca tctaagtctg 60
gtaggggact acatgacttt cgacggagct taccgcgcct tcaacagaat ccacatggca 120
aacaatgcat cgccactcca gcagatgagc tttgaaacga cgtgcacatt tatgaaaaac 180
gctgctttat ttggtacgaa atcccctaag acagatacga agacaatctt tgccatgcta 240
atagtgtttc tgtttttagt gcctggtacg atcattaatt acggcgttga aagtaactcc 300
aaacagcgac cctatatgtc ttcatacaag agacttagtt ctaggaaagc aaataca 357

<210> SEQ ID NO 11
<211> LENGTH: 325
<212> TYPE: DNA
<213> ORGANISM: Varroa destructor

<400> SEQUENCE: 11
tatgaagaca tatagggtcg ctgtttggag ttactttcaa cgccgtaatt aatgatcgta 60
ccaggcacta aaaacagaaa cactattagc atggcaaaga ttgtcttcgt atctgtctta 120
ggggatttcg taccaaataa agcagcgttt ttcataaatg tgcacgtcgt ttcaaagctc 180
atctgctgga gtggcgatgc attgtttgcc atgtggattc tgttgaaggc gcggtaagct 240
ccgtcgaaag tcatgtagtc ccctaccaga cttagatgtc ttggatccac tttgatgccg 300
tacacggcga acacggatgt cacct 325

<210> SEQ ID NO 12
<211> LENGTH: 324
<212> TYPE: DNA
<213> ORGANISM: Varroa destructor

<400> SEQUENCE: 12
atgaagacat atagggtcgc tgtttggagt tactttcaac gccgtaatta atgatcgtac 60
caggcactaa aaacagaaac actattagca tggcaaagat tgtcttcgta tctgtcttag 120
gggatttcgt accaaataaa gcagcgtttt tcataaatgt gcacgtcgtt tcaaagctca 180
tctgctggag tggcgatgca ttgtttgcca tgtggattct gttgaaggcg cggtaagctc 240
cgtcgaaagt catgtagtcc cctaccagac ttagatgtct tggatccact ttgatgccgt 300
acacggcgaa cacggatgtc acct 324

<210> SEQ ID NO 13
<211> LENGTH: 406
<212> TYPE: DNA
<213> ORGANISM: Varroa destructor

<400> SEQUENCE: 13
cctgcgcatc catcagatga ttggaacgga ggaaaatgtc caagtagcat tcgtgggctc 60
gattgtcgag tgtcacaagc tcaaggtgtt tactcaggaa gaagcactga gattccttgc 120
ggcaaagatg aagcagcgga tgtttggacc acagaaagcg gaagacccct tgacaaggca 180

-continued

```
tgggaagccg tactttcatc cgtagtcaac catattcccg ttcaatcgcc tgactacaat    240

atgactgtcc gggcacacta tcttgcacta atggtgcgtc gcatcattca ggcgcgttat    300

gatcgccgct tcattgacga tcgcgactat tacggcaaca aacgaattga gcttccgggt    360

tcgatgatat cgctgctgtt tgaagacctg ttaaaaaagg ttaatg                   406


<210> SEQ ID NO 14
<211> LENGTH: 283
<212> TYPE: DNA
<213> ORGANISM: Varroa destructor

<400> SEQUENCE: 14

tcagatttca gatgattgga acggaggaaa atgtccaagt agcattcgtg ggctcgattg     60

tcgagtgtca caagctcaag gtgtttactc aggaagaagc actgagattc cttgcggcaa    120

agatgaagca gcggatgttt ggaccacaga aagcggaaga ccccccttgac aaggcatggg   180

aagccgtact ttcatccgta gtcaaccata ttcccgttca atcgcctgac tacaatatga    240

ccgtccgggc acactatctt gcactaatgg tgcgtcacat cat                      283


<210> SEQ ID NO 15
<211> LENGTH: 381
<212> TYPE: DNA
<213> ORGANISM: Varroa destructor

<400> SEQUENCE: 15

tcagatgatt ggaacggagg aaaatgtcca agtagcattc gtgggctcga ttgtcgagtg     60

tcacaagctc aaggtgttta ctcaggaaga agcactgaga ttccttgcgg caaagatgaa    120

gcagcggatg tttggaccac agaaagcgga agacccccctt gacaaggcat gggaagccgt   180

actttcatcc gtagtcaacc atattcccgt tcaatcgcct gactacaata tgaccgtccg    240

ggcacactat cttgcactaa tggtgcgtca catcattcag gcgcgttatg atcgccgctt    300

cattgacgat cgcgactatt acggcaacaa acgaattgag cttccgggtt cgatgatatc    360

gctgctgttt gaagacctgt t                                              381


<210> SEQ ID NO 16
<211> LENGTH: 446
<212> TYPE: DNA
<213> ORGANISM: Varroa destructor

<400> SEQUENCE: 16

aatcaattcg tctgcagatc tcaccgattt tctgatatcg ctgggagtcc aggatattcg     60

actactatgc ggagctgaat tcagcaaaac acacgtctac tatgtattcc acaacggtgt    120

tattaaaggc gtcgttgagg atcatcgcag gcttatcaac gagattcggc aatttcgtcg    180

gaagggatac ttgtcgcctt acttatcagt ttatccaaat catctacatc gctgtgtgta    240

tattgtaact gacggtggtc gtttctgcag gccgtttatc attgttgagg atggtcagcc    300

aaaagttacg cagaaacatt tggacgacct caaagccaat atatataact tccaagactt    360

cctggacatg ggctttgtag agtttctcga tgtaaatgag gaaaacgacg cgcttatcgc    420

catttatgaa aaagatatca caatca                                         446


<210> SEQ ID NO 17
<211> LENGTH: 428
<212> TYPE: DNA
<213> ORGANISM: Varroa destructor

<400> SEQUENCE: 17
```

-continued

```
ttcataaatg gcgataagcg cgtcgttttc ctcatttaca tcgagaaact ctacaaagcc     60

catgtccagg aagtcttgga agttatatat attggctttg aggtcgtcca aatgtttctg    120

cgtaactttt ggctgaccat cctcaacaat gataaacggc ctgcagaaac gaccaccgtc    180

agttacaata tacacacagc gatgtagatg atttggataa actgataagt aaggcgacaa    240

ctatcccttc cgacgaaatt gccgaatctc gttgataagc ctgcgatgat cctcaacgac    300

gcctttaata acaccgttgt ggaatacata gtagacgtgt gttttgctga attcagctcc    360

gcatagtagt cgaatatcct ggactcccag cgatatcaga aaatcggtga gatctgcaga    420

cgaattga                                                             428
```

<210> SEQ ID NO 18
<211> LENGTH: 426
<212> TYPE: DNA
<213> ORGANISM: Varroa destructor

<400> SEQUENCE: 18

```
tcaattcgtc tgcagatctc accgattttc tgatatcgct gggaatccag gatattcgac     60

tactatgcgg agctgaattc agcaaaacac acgtctacta tgtattccac aacggtgtta    120

ttaaaggcgt cgttgaggat catcgcaggc ttatcaacga gattcggcaa tttcgtcgga    180

agggatactt gtcgccttac ttatcagttt atccaaatca tctacatcgc tgtgtgtata    240

ttgtaactga cggtggtcgt ttctgcaggc cgtttatcat tgttgaggat ggtcagccaa    300

aagttacgca gaaacatttg gacgacctca aagccaatat atataacttc caagacttcc    360

tggacatggg ctttgtagag tttctcgatg taaatgagga aaacgacgcg cttatcgcca    420

tttatg                                                               426
```

<210> SEQ ID NO 19
<211> LENGTH: 378
<212> TYPE: DNA
<213> ORGANISM: Varroa destructor

<400> SEQUENCE: 19

```
gttttgaaca aaatgagtgt tgagcgcgga tttaaggccg gtgtagtata taaaacagaa     60

acgatcaatt tgcgtaagtt atctggggat gtgggagtcc agacatcgtg cgtttttggt    120

cgaaaggcag gagattctga gttacagaaa tttgtagatg ttgatggcct gccatacatc    180

ggcagcaggg tagtacaggg agatccggta tgtgcatata taaatttgac cacgggacaa    240

ctgaagactg taaggtatta ctcgaccgag ccagcaatcg tgcatgaagt gaaaattctt    300

ggtaatgatt ccggtacaga caccctccaa caaatccagt tgacgtatct tattgatcga    360

acgccaaatg atcggaga                                                  378
```

<210> SEQ ID NO 20
<211> LENGTH: 367
<212> TYPE: DNA
<213> ORGANISM: Varroa destructor

<400> SEQUENCE: 20

```
aatgagtgtt gagcgcggat ttaaggccgg tgtagtatat aaaacagaaa cgatcaattt     60

gcgtaagtta tctggggatg tgggagtcca gacatcgtgc gtttttggtc gaaaggcagg    120

agattctgag ttacagaaat ttgtagatgt tgatggcctg ccatacatcg gcagcagggt    180

agtacaggga gatccggtat gtgcatatat aaatttgacc acgggacaac tgaagactgt    240
```

-continued

```
aaggtattac tcgaccgagc cagcaatcgt gcatgaagtg aaaattcttg gtaatgattc    300

cggtacagac accctccaac aaatccagtt gacgtatctt gttgatcgaa cgccaaatga    360

tcggaga                                                              367


<210> SEQ ID NO 21
<211> LENGTH: 366
<212> TYPE: DNA
<213> ORGANISM: Varroa destructor

<400> SEQUENCE: 21

aatgagtgtt gagcgcggat ttaaggccgg tgtagtatat aaaacagaaa cgatcaattt     60

gcgtaagtta tctggggatg tgggagtcca gacatcgtgc gtttttggtc gaaaggcagg    120

agattctgag ttacagaaat ttgtagatgt tgatggcctg ccatacatcg gcagcagggt    180

agtacaggga gatccggtat gtgcatatat aaatttgacc acgggacaac tgaagactgt    240

aaggtattac tcgaccgagc cagcaatcgt gcatgaagtg aaaattcttg gtaatgattc    300

cggtacagac accctccaac aaatccagct gacgtatctt gttgatcgaa cgccaaatga    360

tcggag                                                               366


<210> SEQ ID NO 22
<211> LENGTH: 268
<212> TYPE: DNA
<213> ORGANISM: Varroa destructor

<400> SEQUENCE: 22

aatggtttct gctacctgtg aggatagtat gcgggatgct tgtattcgtt ttcttgcctc     60

gaaagtcaat ctcaaagcgc ttgacagtga gacagagctt atgctcattg aagaggccgg    120

caaagtggca gccctcgtcg gtggagagga gtttgtgctg ctggttaagc tcctcaattc    180

attaaaggta gattgtacat tttggcgtct tctcgaacaa gttagaatct atttagcaaa    240

gtgccaatgt atcagcttcc aatacgca                                       268


<210> SEQ ID NO 23
<211> LENGTH: 263
<212> TYPE: DNA
<213> ORGANISM: Varroa destructor

<400> SEQUENCE: 23

attggaagct gatacattgg cactttgcta aatagattct aacttgttcg agaagacgcc     60

aaaatgtaca atctaccttt aatgaattga ggagcttaac cagcagcaca aactcctctc    120

caccgacgag ggctgccact ttgccggcct cttcaatgag cataagctct gtctctctgt    180

caagcgcttt gagattgact ttcgaggcaa gaaaacgaat acaagcatcc cgcatactat    240

cctcacaggt agcagaaacc att                                            263


<210> SEQ ID NO 24
<211> LENGTH: 263
<212> TYPE: DNA
<213> ORGANISM: Varroa destructor

<400> SEQUENCE: 24

attggaagct gatacattgg cactttgcta aatagattct aacttgttcg agaagacgcc     60

aaaatgtaca atctaccttt aatgaattga ggagcttaac cagcagcaca aactcctctc    120

caccgacgag ggctgccact ttgccggcct cttcaatgag cataagctct gtctctctgt    180

caagcgcttt gagattgact ttcgaggcaa gaaaacgaat acaagcatcc cgcatactat    240
```

-continued cctcacaggt agcagaaacc att 263

<210> SEQ ID NO 25
<211> LENGTH: 279
<212> TYPE: DNA
<213> ORGANISM: Varroa destructor

<400> SEQUENCE: 25
gatcttgttg aagccggctt cttcttcctt ggcatgcacg attacacgaa atgcttccat 60
tgcgacggcg gtctgtgtaa ttgggagaca ggtgacgacc cctgggtaga gcatgcccgc 120
tggttccctg aatgtcaatt cgttcagcta agcaagggcg gagcattcat cgctgagtgc 180
caacaacgtc acgaaaaact agttaatggc gcggtagccc aggcagaact tcaggctttt 240
agtgaagtag aaccgggagg aacaggcagt gactcaaat 279

<210> SEQ ID NO 26
<211> LENGTH: 263
<212> TYPE: DNA
<213> ORGANISM: Varroa destructor

<400> SEQUENCE: 26
agtcactgcc tgttcctccc ggttctactt cactaaaagc ctgaagttct gcctgggcta 60
ccgcgccatt aactagtttt tcgtgacgtt gttggcactc agcgatgaat gctccgccct 120
tgcttagctg aacgaattga cattcaggga accagcgggc atgctctacc caggggtcgt 180
cacctgtctc ccaattacac agaccgccgt cgcaatggaa gcatttcgtg taatcgtgca 240
tgccaaggaa gaagaagccg gct 263

<210> SEQ ID NO 27
<211> LENGTH: 299
<212> TYPE: DNA
<213> ORGANISM: Varroa destructor

<400> SEQUENCE: 27
ttccgcttca tttgagaact gagcttgaag aaataatgca gtcgcccgtc gtcaagttct 60
acctcgagaa aggtgtaccg aaacaagtga ttcgaatgac cgtaaaaaat atatgcttga 120
caacgagcgc ggtttccgtg atcttgacga aattacacac gtactcggac aggtgctcag 180
cttcggcaac aagaagactg cgcctgccaa tgaaaaaggt aggtggatac cggatatttg 240
tcgggaattc aatgcagctg aacccgatga ggttgattca gaattggcat acaatagaa 299

<210> SEQ ID NO 28
<211> LENGTH: 284
<212> TYPE: DNA
<213> ORGANISM: Varroa destructor

<400> SEQUENCE: 28
ttccgcttca tttgagaact gagcttgaag aaataatgca gtcgcccgtc gtcaagttct 60
acctcgagaa aggtgtaccg aaacaagtga ttcgaatgac cgtaaaaaaa tatatgcttg 120
acaacgagcg cggtttccgt gatcttgacg aaattacaca cgtactcgga caggtgctca 180
gcttcggcaa caagaagact gcgcctgcca atgaaaaagg taggtggata ccggatattt 240
gtcgggaatt caatgcagct gaacccgatg aggttgattc agaa 284

<210> SEQ ID NO 29
<211> LENGTH: 283
<212> TYPE: DNA

<213> ORGANISM: Varroa destructor

<400> SEQUENCE: 29
ttccgcttca tttgagaact gagcttgaag aaataatgca gtcgcccgtc gtcaagttct 60
acctcgagaa aggtgtaccg aaacaagtga ttcgaatgac cgtgaaaaaa tatatgcttg 120
acaacgagcg cggtttccgt gatcttgacg aaattacaca cgtactcgga caggtgctca 180
gcttcggcaa caagaagact gcgcctgcca atgaaaaagg taggtggata ccggatattt 240
gtcgggaatt caatgcagct gaacccgatg aggttgattc aga 283

<210> SEQ ID NO 30
<211> LENGTH: 279
<212> TYPE: DNA
<213> ORGANISM: Varroa destructor

<400> SEQUENCE: 30
tggctaatta atagtaggcc gaagaacttt ttgagtggcc tcgatatgtc cgacgttgtg 60
gcttcgtggg aggttccttt ggttggccaa gcttaccgag tcgaattcga acacggaagt 120
gcaacgggta aacgtgttgt gtacgttaat ggactcgagg tgttacgaaa acactggctt 180
tttaagcttg ttggcgagga aagctttgac atattgggac ataagtgcat catttctatc 240
aaagccgtag gaggcttcag gttggtagca aactccagt 279

<210> SEQ ID NO 31
<211> LENGTH: 277
<212> TYPE: DNA
<213> ORGANISM: Varroa destructor

<400> SEQUENCE: 31
tggctaatta atagtaggcc gaagaacttt ttgagtggcc tcgatatgtc cgacgttgtg 60
gcttcgtggg aggttccttt ggttggccaa gcttaccgag tcgaattcga acacggaagt 120
gcaacgggta aacgtgttgt gtacgttaat ggactcgagg tgttacgaaa acactggctt 180
tttaagcttg ttggcgagga aagctttgac atattgggac ataagtgcat catttctatc 240
aaagccgtag gaggcttcag gttggtagca aactcca 277

<210> SEQ ID NO 32
<211> LENGTH: 277
<212> TYPE: DNA
<213> ORGANISM: Varroa destructor

<400> SEQUENCE: 32
tggagtttgc taccaacctg aagcctccta cggctttgat agaaatgatg cacttatgtc 60
ccaatatgtc aaagctttcc tcgccaacaa gcttaaaaag ccagtgtttt cgtaacacct 120
cgagtccatt aacgtacaca acacgtttac ccgttgcact tccgtgttcg aattcgactc 180
ggtaagcttg gccaaccaaa ggaacctccc acgaagccac aacgtcggac atatcgaggc 240
cactcaaaaa gttcttcggc ctactattaa ttagcca 277

<210> SEQ ID NO 33
<211> LENGTH: 283
<212> TYPE: DNA
<213> ORGANISM: Varroa destructor

<400> SEQUENCE: 33
ggtcttgaca acacatgcta ccctcgaaca cgccgactgc gtcttcatga tggacaatga 60
ggccatctat cagatctgcc gtcggaacct tggagtcgag cgaccggcgt accagaatct 120
caaccgtctg atcagtcagg ccgtttcggc gattaccgct tctctacgtt tctccggagc 180
gctgaatgtt gatcttaacg agttccaaac taatttagtt ccatacccgc gaatccattt 240
tcccctcgtc acttacgctc cgatcatttc tgctgagaag gct 283

<210> SEQ ID NO 34
<211> LENGTH: 279
<212> TYPE: DNA
<213> ORGANISM: Varroa destructor

<400> SEQUENCE: 34
ggtcttgaca acacatgcta ccctcgaaca cgccgactgc gtcttcatga tggacaatga 60
ggccatctat cagatctgcc gtcggaacct tggagtcgag cgaccggcgt accagaatct 120
caaccgtctg atcagtcagg ccgtttcggc gattaccgct tctctacgtt tctccggagc 180
gctgaatgtt gatcttaacg agttccaaac taatttagtt ccatacccgc gaatccattt 240
tccccccgtc acttacgctc cgatcatttc tgctgagaa 279

<210> SEQ ID NO 35
<211> LENGTH: 277
<212> TYPE: DNA
<213> ORGANISM: Varroa destructor

<400> SEQUENCE: 35
ctcagcagaa atgatcggag cgtaagtgac ggggggaaaa tggattcgcg ggtatggaac 60
taaattagtt tggaactcgt taagatcaac attcagcgct ccggagaaac gtagagaagc 120
ggtaatcgcc gaaacggcct gactgatcag acggttgaga ttctggtacg ccggtcgctc 180
gactccaagg ttccgacggc agatctgata gatggcctca ttgtccatca tgaagacgca 240
gtcggcgtgt tcgagggtag catgtgttgt caagacc 277

<210> SEQ ID NO 36
<211> LENGTH: 332
<212> TYPE: DNA
<213> ORGANISM: Varroa destructor

<400> SEQUENCE: 36
caacgctgtg cttcacgtag actccacgtt cgaaaatgtc gactgcacgt ttatggttga 60
taatcaaaca ctcttcaagc tttgtcgaga ccggctaaag attaggagtc catcttatga 120
caacgcaaat gctgtcattt cccagggttt ttcgtcaatc atgaattcgg tggggctgga 180
tggatccttg aatgtggacc tcagcgagtt ccaaacaaat ctcgtccctt ttggaagatt 240
acattttacg atgatgagct acagtccatt cgttacatcc ggacaccgcg atctaagccg 300
tgagacgtcc gtcgtggaga ttactcgtga cc 332

<210> SEQ ID NO 37
<211> LENGTH: 330
<212> TYPE: DNA
<213> ORGANISM: Varroa destructor

<400> SEQUENCE: 37
caacgctgtg cttcacgtag actccacgtt cgaaaatgtc gactgcacgt ttatggttga 60
taatcaaaca ctcctcaagc tttgtcgaga ccggctaaag gttaggagtc catcttatga 120
caacgcaaat gctgtcattt cccagggttt ttcgtcaatc atgaattcgg tggggctgga 180
tggatccttg aatgtggacc tcagcgagtt ccaaacaagt ctcgtccctt ttggaagatt 240

```
acattttacg atgatgagct acagtccatt cgttacatcc ggacaccgcg atctaagccg    300

tgagacgtcc gtcgtggaga ttactcgtga                                     330


<210> SEQ ID NO 38
<211> LENGTH: 329
<212> TYPE: DNA
<213> ORGANISM: Varroa destructor

<400> SEQUENCE: 38

aacgctgtgc ttcacgtaga ctccacgttc gaaaatgtcg actgcacgtt tatggttgat     60

aatcaaacac tcctcaagct ttgtcgagac cggctaaagg ttaggagtcc atcttatgac    120

aacgcaaatg ctgtcatttc ccagggtttt tcgtgaatca tgaattcggt ggggctggat    180

ggatccttga atgtggacct cagcgagttc caaacaagtc tcgtcccttt tggaagatta    240

cattttacga tgatgagcta cagtccattc gttacatccg gacaccgcga tctaagccgt    300

gagacgtccg tcgtggagat tactcgtga                                      329


<210> SEQ ID NO 39
<211> LENGTH: 415
<212> TYPE: DNA
<213> ORGANISM: Varroa destructor

<400> SEQUENCE: 39

tatggagaac atcgcacagg acttcggtaa aaagtgccga ttgggcttcg ccatctaccc     60

ggctccgcag gtttccactg ccgttgtcga accatacaac tcggttttga cgacacatgc    120

caccctcgaa cacgctgact gcgtattcat gatggataat gaggcgatct atcagatctg    180

tcgtcggaat cttggagttg aacgaccggc gtatcaaaat ctcaatcgac tgattagcca    240

ggccgtttcg gcgataaccg cttctctacg tttttccgga gcgttgaatg ttgacctcaa    300

cgaatttcag acgaatctcg tcccctaccc gcgaatccat ttcccgctcg tcacttatgc    360

tccgattatt tcggctgaga aggctcatca cgagcaacat aacgtactgg aaatc         415


<210> SEQ ID NO 40
<211> LENGTH: 412
<212> TYPE: DNA
<213> ORGANISM: Varroa destructor

<400> SEQUENCE: 40

atggagaaca tcgcacagga cttcggtaaa aagtgccgat tgggcttcgc catctacccg     60

gctccgcagg tttccactgc cgttgtcgaa ccatacaact cggttttgac gacacatgcc    120

accctcgaac acgctgactg cgtattcatg atggataatg aggcgatcta tcagatctgt    180

cgtcggaatc ttggagttga acgaccggcg tatcaaaatc tcaatcgact gattagccag    240

gccgtttcgg cgataaccgc ttctctacgt ttttccggag cgttgaatgt tgacctcaac    300

gaatttcaga cgaatctcgt cccctacccg cgaatccatt tcccgctcgt cacttatgct    360

ccgattattt cggctgagaa ggctcatcac gagcaacata acgtactgga aa            412


<210> SEQ ID NO 41
<211> LENGTH: 411
<212> TYPE: DNA
<213> ORGANISM: Varroa destructor

<400> SEQUENCE: 41

atggagaaca tcgcacagga cttcggtaaa aagtgccgat tgggcttcgc catctacccg     60

gctccgcagg tttccactgc cgttgtcgaa ccatacaact cggttttgac gacacatgcc    120
```

-continued

```
accctcgaac acgctgactg cgtattcatg atggataatg aggcgatcta tcagatctgt    180

cgtcggaatc ttggagttga acgaccggcg tatcaaaatc tcaatcgact gattagccag    240

gccgtttcgg cgataaccgc ttctctacgt ttttccggag cgttgaatgt tgacctcaac    300

gaatttcaga cgaatctcgt cccctacccg cgaatccatt tcccgctcgt cacttatgct    360

ccgattattt cggctgagaa ggctcatcac gagcaacata acgtactgga a             411


<210> SEQ ID NO 42
<211> LENGTH: 266
<212> TYPE: DNA
<213> ORGANISM: Varroa destructor

<400> SEQUENCE: 42

attttattca attaaagtat ttaccaattg gaataaagat aggattaatg ataatttttt     60

taagtttaag tggaatacct ccctttatag gatttatttc taagataact gttttgttga    120

tgtattttga gaatcaaaaa ataatttttt taattatatt attagtatct gtaataagaa    180

tatatattta tataaattat tttatgaaga gtttattttt tataagatta ggttataata    240

aaaataaaaa tataggaata agaaga                                          266


<210> SEQ ID NO 43
<211> LENGTH: 99
<212> TYPE: DNA
<213> ORGANISM: Varroa destructor

<400> SEQUENCE: 43

atacctcaaa tgtatccttc atattgagta ttaattcata tagtatttat attgaattat     60

tatataataa taatttatta ttattttata tttaagtaa                            99


<210> SEQ ID NO 44
<211> LENGTH: 501
<212> TYPE: DNA
<213> ORGANISM: Varroa destructor

<400> SEQUENCE: 44

ggccaatccc gattccggcg acacaaagaa attacaagaa gctatagacc gttttcatcg     60

agccggaaga tggattaaga aaaaatttcg agatctattc atgctatgtt cgggtaaaca    120

gcgcaaccag atctcggatc aaacctacgc cgaagacctg gacctcgaca caggggtcat    180

tattatggat ggacaggtta ttaagaagga tagccccacg cccgaactca tcgatgggtt    240

ggatgttggt tttcaagctg ataagcaaca ggcgcaggtg attgtaatgc aaaagcttaa    300

aaacaattcc cgacctatca ttggcgactc aaaggaattt agcaacaaag ttcatccagg    360

ccccgacttt tgcctggtaa agccgaacga caacggcgaa ggcctcgtgc aagacaccga    420

gcttggggcc tccacgccgc tcagctcgcc ttcctgtata gttgaacagc ctctgtctca    480

cgacagtgtg ggcctgccac c                                              501


<210> SEQ ID NO 45
<211> LENGTH: 21
<212> TYPE: DNA
<213> ORGANISM: Artificial sequence
<220> FEATURE:
<223> OTHER INFORMATION: Exemplary siRNA targeting sequence

<400> SEQUENCE: 45

attttattca attaaagtat t                                               21
```

<210> SEQ ID NO 46
<211> LENGTH: 21
<212> TYPE: DNA
<213> ORGANISM: Artificial sequence
<220> FEATURE:
<223> OTHER INFORMATION: Exemplary siRNA targeting sequence

<400> SEQUENCE: 46
atacctcaaa tgtatccttc a 21

<210> SEQ ID NO 47
<211> LENGTH: 21
<212> TYPE: DNA
<213> ORGANISM: Artificial sequence
<220> FEATURE:
<223> OTHER INFORMATION: Exemplary siRNA targeting sequence

<400> SEQUENCE: 47
ggccaatccc gattccggcg a 21

<210> SEQ ID NO 48
<211> LENGTH: 24
<212> TYPE: DNA
<213> ORGANISM: Artificial sequence
<220> FEATURE:
<223> OTHER INFORMATION: T7 promoters

<400> SEQUENCE: 48
ctaatacgac tcactatagg gcga 24

<210> SEQ ID NO 49
<211> LENGTH: 24
<212> TYPE: DNA
<213> ORGANISM: Artificial sequence
<220> FEATURE:
<223> OTHER INFORMATION: T7 promoters (reverse complement orientation)

<400> SEQUENCE: 49
tcgccctata gtgagtcgta ttag 24

<210> SEQ ID NO 50
<211> LENGTH: 419
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (395)..(419)
<223> OTHER INFORMATION: Promoter

<400> SEQUENCE: 50
ctaatacgac tcactatagg gcgagttagc cgtctgaagc aatgcttgac tgtacagggt 60
ccgaatataa aacttcatac attcaaaatc acgtatcagg attatgctaa acatcgcacc 120
ataaaaatct tcactaaagt tattttacgc ttcaggatag tggtccgtta tgagtgttgc 180
ggtattagtg cgtttacaaa tttgctaacg atattaacaa gcttatttca ctcgttggca 240
ggttttctag aacgcgaggt gaggaaggat aaccttccga tgatgtcatt cggcgacaat 300
cctgaggcgc ctcagcctcg ggagatgatt gatctagaag caacctttga gaaactcgaa 360
aacgaactca atgaggtagt tttctgtgtt gaaattcgcc ctatagtgag tcgtattag 419

<210> SEQ ID NO 51
<211> LENGTH: 361
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (337)..(361)
<223> OTHER INFORMATION: Promoter

<400> SEQUENCE: 51
ctaatacgac tcactatagg gcgactgtac agggtccgaa tataaaactt catacattca 60
aaatcacgta tcaggattat gctaaacatc gcaccataaa aatcttcact aaagttattt 120
tacgcttcag gatagtggtc cgttatgagt gttgcggtat tagtgcgttt acagatttgc 180
taacgttatt aacaagctaa tttcactcgt tggcaggttt tctagaacgc gaggtgagga 240
aggataacct tccgatgatg tcattcggcg acaatcctga ggcgcctcag cctcgggaga 300
tgattgatct agaagcaacc tttgagaaac tcgaaaatcg ccctatagtg agtcgtatta 360
g 361

<210> SEQ ID NO 52
<211> LENGTH: 359
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (335)..(359)
<223> OTHER INFORMATION: Promoter

<400> SEQUENCE: 52
ctaatacgac tcactatagg gcgattcgag tttctcaaag gttgcttcta gatcaatcat 60
ctcccgaggc tgaggcgcct caggattgtc gccgaatgac atcatcggaa ggttatcctt 120
cctcacctcg cgttctagaa aacctgccaa cgagtgaaat tagcttgtta ataacgttag 180
caaatctgta aacgcactaa taccgcaaca ctcataacgg accactatcc tgaagcgtaa 240
aataacttta gtgaagattt ttatggtgcg atgtttagca taatcctgat acgtgatttt 300
gaatgtatga agttttatat tcggaccctg tacagtcgcc ctatagtgag tcgtattag 359

<210> SEQ ID NO 53
<211> LENGTH: 290
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:

<221> NAME/KEY: misc_feature
<222> LOCATION: (266)..(290)
<223> OTHER INFORMATION: Promoter

<400> SEQUENCE: 53
ctaatacgac tcactatagg gcgacaactc attaaaatga aatcagtatt ccacatcatg 60
aatcaattga atatggacgt cactcagaag tgtcttattg ccgaatgctg gattcctgat 120
cgcgatgtag caaaggtaca agctgccctg cgacgtggaa cggaagcggc tggaagcagc 180
ttcccgtgta tcattaaccg gttggaaacg gaccaagctc caccgacgtt ctacagaacg 240
aactcgttta ctgctggctt tcaaaatcgc cctatagtga gtcgtattag 290

<210> SEQ ID NO 54
<211> LENGTH: 261
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (237)..(261)
<223> OTHER INFORMATION: Promoter

<400> SEQUENCE: 54
ctaatacgac tcactatagg gcgacaattc gtgattcaat tgaatatgga cgtcactcag 60
aagtgtctta ttgccgaatg ctggattcct gatcgcgatg tagcaaaggt acaagctgcc 120
ctgcgacgtg gaacggaagc ggctggaagc agcttcccgt gtatcattaa ccggttggaa 180
acggacaaag ctccaccgac gttctacaga acgaactcgt ttactgctgg ctttcaatcg 240
ccctatagtg agtcgtatta g 261

<210> SEQ ID NO 55
<211> LENGTH: 249
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (225)..(249)
<223> OTHER INFORMATION: Promoter

<400> SEQUENCE: 55
ctaatacgac tcactatagg gcgacaattg aatatggacg tcactcagaa gtgtcttatt 60
gccgaatgct ggattcctga tcgcgatgta gcaaaggtac aagctgccct gcgacgtgga 120
acggaagcgg ctggaagcag cttcccgtgt atcattaacc ggttggaaac ggacaaagct 180
ccaccgacgt tctacagaac gaactcgttt attgctggct ttcaatcgcc ctatagtgag 240
tcgtattag 249

<210> SEQ ID NO 56
<211> LENGTH: 355
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (331)..(355)
<223> OTHER INFORMATION: Promoter

<400> SEQUENCE: 56
ctaatacgac tcactatagg gcgaaatcac aattttctac atcatcttct tcatctgctt 60
ggcggcattc tggacggtta tgctggtcat cttctatcag acactcgatg ccttccagcc 120
aaagtggacc ctggacgcta gtctcattgg cactgtaccg ggattaggct tcaggccacg 180
cccaccgctg tctaacatcg actcaacact catctatttc aaggtatcta agccgttagt 240
gtatatgtta tattatagcg ctctttgtta tgtggaaaga cgccagggcg cgtatctata 300
tggtggtttt cataccaacc gtgggaaccc actaatacga ctcactatag ggcga 355

<210> SEQ ID NO 57
<211> LENGTH: 338
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (314)..(338)
<223> OTHER INFORMATION: Promoter

<400> SEQUENCE: 57
ctaatacgac tcactatagg gcgaggttcc cacggttggt atgaaaacca ccatatagat 60
acgcgccctg gcgtctttcc acataacaaa gagcgctata atataacata tacactaacg 120
gcttagatac cttgaaatag atgagtgttg agtcgatgtt agacagcggt gggcgtggcc 180
tgaagcctaa tcccggtaca gtgccaatga gactagcgtc cagggtccac tttggctgga 240
aggcatcgag tgtctgatag aagatgacca gcataaccgt ccagaatgcc gccaagcaga 300
tgaagaagat gatgtcgccc tatagtgagt cgtattag 338

<210> SEQ ID NO 58
<211> LENGTH: 338
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (314)..(338)
<223> OTHER INFORMATION: Promoter

<400> SEQUENCE: 58
ctaatacgac tcactatagg gcgacatcat cttcttcatc tgcttggcgg cattctggac 60
ggttatgctg gtcatcttct atcagacact cgatgccttc cagccaaagt ggaccctgga 120
cgctagtctc attggcactg taccgggatt aggcttcagg ccacgcccac cgctgtctaa 180
catcgactca acactcatct atttcaaggt atctaagccg ttagtgtata tgttatatta 240
tagcgctctt tgttatgtgg aaagacgcca gggcgcgtat ctatatggtg gttttcatac 300
caaccgtggg aacctcgccc tatagtgagt cgtattag 338

<210> SEQ ID NO 59
<211> LENGTH: 405
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (381)..(405)
<223> OTHER INFORMATION: Promoter

<400> SEQUENCE: 59
ctaatacgac tcactatagg gcgagaggtg acatccgtgt tcgccgtgta cggcatcaaa 60
gtggatccaa gacatctaag tctggtaggg gactacatga ctttcgacgg agcttaccgc 120
gccttcaaca gaatccacat ggcaaacaat gcatcgccac tccagcagat gagctttgaa 180
acgacgtgca catttatgaa aaacgctgct ttatttggta cgaaatcccc taagacagat 240
acgaagacaa tctttgccat gctaatagtg tttctgtttt tagtgcctgg tacgatcatt 300
aattacggcg ttgaaagtaa ctccaaacag cgaccctata tgtcttcata caagagactt 360
agttctagga aagcaaatac atcgccctat agtgagtcgt attag 405

<210> SEQ ID NO 60
<211> LENGTH: 373
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (349)..(373)
<223> OTHER INFORMATION: Promoter

<400> SEQUENCE: 60
ctaatacgac tcactatagg gcgatatgaa gacatatagg gtcgctgttt ggagttactt 60
tcaacgccgt aattaatgat cgtaccaggc actaaaaaca gaaacactat tagcatggca 120
aagattgtct tcgtatctgt cttaggggat ttcgtaccaa ataaagcagc gtttttcata 180
aatgtgcacg tcgtttcaaa gctcatctgc tggagtggcg atgcattgtt tgccatgtgg 240
attctgttga aggcgcggta agctccgtcg aaagtcatgt agtcccctac cagacttaga 300
tgtcttggat ccactttgat gccgtacacg gcgaacacgg atgtcacctt cgccctatag 360
tgagtcgtat tag 373

<210> SEQ ID NO 61
<211> LENGTH: 372
<212> TYPE: DNA

<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (348)..(372)
<223> OTHER INFORMATION: Promoter

<400> SEQUENCE: 61
ctaatacgac tcactatagg gcgaatgaag acatataggg tcgctgtttg gagttacttt 60
caacgccgta attaatgatc gtaccaggca ctaaaaacag aaacactatt agcatggcaa 120
agattgtctt cgtatctgtc ttaggggatt tcgtaccaaa taaagcagcg tttttcataa 180
atgtgcacgt cgtttcaaag ctcatctgct ggagtggcga tgcattgttt gccatgtgga 240
ttctgttgaa ggcgcggtaa gctccgtcga aagtcatgta gtcccctacc agacttagat 300
gtcttggatc cactttgatg ccgtacacgg cgaacacgga tgtcaccttc gccctatagt 360
gagtcgtatt ag 372

<210> SEQ ID NO 62
<211> LENGTH: 453
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (429)..(453)
<223> OTHER INFORMATION: Promoter

<400> SEQUENCE: 62
ctaatacgac tcactatagg gcgacctgcg catccatcag atgattggaa cggaggaaaa 60
tgtccaagta gcattcgtgg gctcgattgt cgagtgtcac aagctcaagg tgtttactca 120
ggaagaagca ctgagattcc ttgcggcaaa gatgaagcag cggatgtttg gaccacagaa 180
agcggaagac cccttgacaa ggcatgggaa gccgtacttt catccgtagt caaccatatt 240
cccgttcaat cgcctgacta caatatgact gtccgggcac actatcttgc actaatggtg 300
cgtcgcatca ttcaggcgcg ttatgatcgc cgcttcattg acgatcgcga ctattacggc 360
aacaaacgaa ttgagcttcc gggttcgatg atatcgctgc tgtttgaaga cctgttaaaa 420
aaggttaatt cgccctatag tgagtcgtat tag 453

<210> SEQ ID NO 63
<211> LENGTH: 331
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (307)..(331)

<223> OTHER INFORMATION: Promoter

<400> SEQUENCE: 63

```
ctaatacgac tcactatagg gcgatcagat ttcagatgat tggaacggag gaaaatgtcc    60

aagtagcatt cgtgggctcg attgtcgagt gtcacaagct caaggtgttt actcaggaag   120

aagcactgag attccttgcg gcaaagatga agcagcggat gtttggacca cagaaagcgg   180

aagaccccct tgacaaggca tgggaagccg tactttcatc cgtagtcaac catattcccg   240

ttcaatcgcc tgactacaat atgaccgtcc gggcacacta tcttgcacta atggtgcgtc   300

acatcattcg ccctatagtg agtcgtatta g                                  331
```

<210> SEQ ID NO 64
<211> LENGTH: 429
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (405)..(429)
<223> OTHER INFORMATION: Promoter

<400> SEQUENCE: 64

```
ctaatacgac tcactatagg gcgatcagat gattggaacg gaggaaaatg tccaagtagc    60

attcgtgggc tcgattgtcg agtgtcacaa gctcaaggtg tttactcagg aagaagcact   120

gagattcctt gcggcaaaga tgaagcagcg gatgtttgga ccacagaaag cggaagaccc   180

ccttgacaag gcatgggaag ccgtactttc atccgtagtc aaccatattc ccgttcaatc   240

gcctgactac aatatgaccg tccgggcaca ctatcttgca ctaatggtgc gtcacatcat   300

tcaggcgcgt tatgatcgcc gcttcattga cgatcgcgac tattacggca acaaacgaat   360

tgagcttccg ggttcgatga tatcgctgct gtttgaagac ctgtttcgcc ctatagtgag   420

tcgtattag                                                           429
```

<210> SEQ ID NO 65
<211> LENGTH: 494
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (470)..(494)
<223> OTHER INFORMATION: Promoter
<400> SEQUENCE: 65
ctaatacgac tcactatagg gcgaaatcaa ttcgtctgca gatctcaccg attttctgat 60
atcgctggga gtccaggata ttcgactact atgcggagct gaattcagca aaacacacgt 120
ctactatgta ttccacaacg gtgttattaa aggcgtcgtt gaggatcatc gcaggcttat 180
caacgagatt cggcaatttc gtcggaaggg atacttgtcg ccttacttat cagtttatcc 240
aaatcatcta catcgctgtg tgtatattgt aactgacggt ggtcgtttct gcaggccgtt 300
tatcattgtt gaggatggtc agccaaaagt tacgcagaaa catttggacg acctcaaagc 360
caatatatat aacttccaag acttcctgga catgggcttt gtagagtttc tcgatgtaaa 420
tgaggaaaac gacgcgctta tcgccattta tgaaaaagat atcacaatca tcgccctata 480
gtgagtcgta ttag 494

<210> SEQ ID NO 66
<211> LENGTH: 476
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (452)..(476)
<223> OTHER INFORMATION: Promoter

<400> SEQUENCE: 66
ctaatacgac tcactatagg gcgattcata aatggcgata agcgcgtcgt ttcctcatt 60 tacatcgaga aactctacaa agcccatgtc caggaagtct tggaagttat atatattggc 120
tttgaggtcg tccaaatgtt tctgcgtaac ttttggctga ccatcctcaa caatgataaa 180
cggcctgcag aaacgaccac cgtcagttac aatatacaca cagcgatgta gatgatttgg 240
ataaactgat aagtaaggcg acaactatcc cttccgacga aattgccgaa tctcgttgat 300
aagcctgcga tgatcctcaa cgacgccttt aataacaccg ttgtggaata catagtagac 360
gtgtgttttg ctgaattcag ctccgcatag tagtcgaata tcctggactc ccagcgatat 420
cagaaaatcg gtgagatctg cagacgaatt gatcgcccta tagtgagtcg tattag 476

<210> SEQ ID NO 67
<211> LENGTH: 474
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (450)..(474)
<223> OTHER INFORMATION: Promoter

<400> SEQUENCE: 67
ctaatacgac tcactatagg gcgatcaatt cgtctgcaga tctcaccgat tttctgatat 60
cgctgggaat ccaggatatt cgactactat gcggagctga attcagcaaa acacacgtct 120
actatgtatt ccacaacggt gttattaaag gcgtcgttga ggatcatcgc aggcttatca 180
acgagattcg gcaatttcgt cggaagggat acttgtcgcc ttacttatca gtttatccaa 240
atcatctaca tcgctgtgtg tatattgtaa ctgacggtgg tcgtttctgc aggccgttta 300
tcattgttga ggatggtcag ccaaaagtta cgcagaaaca tttggacgac ctcaaagcca 360
atatatataa cttccaagac ttcctggaca tgggctttgt agagtttctc gatgtaaatg 420
aggaaaacga cgcgcttatc gccatttatg tcgccctata gtgagtcgta ttag 474

<210> SEQ ID NO 68
<211> LENGTH: 426
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (402)..(426)
<223> OTHER INFORMATION: Promoter

<400> SEQUENCE: 68
ctaatacgac tcactatagg gcgagttttg aacaaaatga gtgttgagcg cggatttaag 60
gccggtgtag tatataaaac agaaacgatc aatttgcgta agttatctgg ggatgtggga 120
gtccagacat cgtgcgtttt tggtcgaaag gcaggagatt ctgagttaca gaaatttgta 180
gatgttgatg gcctgccata catcggcagc agggtagtac agggagatcc ggtatgtgca 240
tatataaatt tgaccacggg acaactgaag actgtaaggt attactcgac cgagccagca 300
atcgtgcatg aagtgaaaat tcttggtaat gattccggta cagacaccct ccaacaaatc 360
cagttgacgt atcttattga tcgaacgcca aatgatcgga gatcgcccta tagtgagtcg 420
tattag 426

<210> SEQ ID NO 69
<211> LENGTH: 415
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (391)..(415)
<223> OTHER INFORMATION: Promoter

<400> SEQUENCE: 69
ctaatacgac tcactatagg gcgaaatgag tgttgagcgc ggatttaagg ccggtgtagt 60
atataaaaca gaaacgatca atttgcgtaa gttatctggg gatgtgggag tccagacatc 120
gtgcgttttt ggtcgaaagg caggagattc tgagttacag aaatttgtag atgttgatgg 180
cctgccatac atcggcagca gggtagtaca gggagatccg gtatgtgcat atataaattt 240
gaccacggga caactgaaga ctgtaaggta ttactcgacc gagccagcaa tcgtgcatga 300
agtgaaaatt cttggtaatg attccggtac agacaccctc caacaaatcc agttgacgta 360
tcttgttgat cgaacgccaa atgatcggag atcgccctat agtgagtcgt attag 415

<210> SEQ ID NO 70
<211> LENGTH: 414
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)

<223> OTHER INFORMATION: Promoter
<220> FEATURE:
<221> NAME/KEY: misc_feature
<222> LOCATION: (390)..(414)
<223> OTHER INFORMATION: Promoter

<400> SEQUENCE: 70
ctaatacgac tcactatagg gcgaaatgag tgttgagcgc ggatttaagg ccggtgtagt 60
atataaaaca gaaacgatca atttgcgtaa gttatctggg gatgtgggag tccagacatc 120
gtgcgttttt ggtcgaaagg caggagattc tgagttacag aaatttgtag atgttgatgg 180
cctgccatac atcggcagca gggtagtaca gggagatccg gtatgtgcat atataaattt 240
gaccacggga caactgaaga ctgtaaggta ttactcgacc gagccagcaa tcgtgcatga 300
agtgaaaatt cttggtaatg attccggtac agacaccctc caacaaatcc agctgacgta 360
tcttgttgat cgaacgccaa atgatcggag tcgccctata gtgagtcgta ttag 414

<210> SEQ ID NO 71
<211> LENGTH: 316
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (292)..(316)
<223> OTHER INFORMATION: Promoter

<400> SEQUENCE: 71
ctaatacgac tcactatagg gcgaaatggt ttctgctacc tgtgaggata gtatgcggga 60
tgcttgtatt cgttttcttg cctcgaaagt caatctcaaa gcgcttgaca gtgagacaga 120
gcttatgctc attgaagagg ccggcaaagt ggcagccctc gtcggtggag aggagtttgt 180
gctgctggtt aagctcctca attcattaaa ggtagattgt acattttggc gtcttctcga 240
acaagttaga atctatttag caaagtgcca atgtatcagc ttccaatacg catcgcccta 300
tagtgagtcg tattag 316

<210> SEQ ID NO 72
<211> LENGTH: 311
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (287)..(311)
<223> OTHER INFORMATION: Promoter

<400> SEQUENCE: 72
ctaatacgac tcactatagg gcgaattgga agctgataca ttggcacttt gctaaataga 60
ttctaacttg ttcgagaaga cgccaaaatg tacaatctac ctttaatgaa ttgaggagct 120
taaccagcag cacaaactcc tctccaccga cgagggctgc cactttgccg gcctcttcaa 180
tgagcataag ctctgtctct ctgtcaagcg ctttgagatt gactttcgag gcaagaaaac 240

```
gaatacaagc atcccgcata ctatcctcac aggtagcaga aaccatttcg ccctatagtg    300

agtcgtatta g                                                         311


<210> SEQ ID NO 73
<211> LENGTH: 311
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (287)..(311)
<223> OTHER INFORMATION: Promoter

<400> SEQUENCE: 73

ctaatacgac tcactatagg gcgaattgga agctgataca ttggcacttt gctaaataga     60

ttctaacttg ttcgagaaga cgccaaaatg tacaatctac ctttaatgaa ttgaggagct    120

taaccagcag cacaaactcc tctccaccga cgagggctgc cactttgccg gcctcttcaa    180

tgagcataag ctctgtctct ctgtcaagcg ctttgagatt gactttcgag gcaagaaaac    240

gaatacaagc atcccgcata ctatcctcac aggtagcaga aaccatttcg ccctatagtg    300

agtcgtatta g                                                         311


<210> SEQ ID NO 74
<211> LENGTH: 327
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (303)..(327)
<223> OTHER INFORMATION: Promoter

<400> SEQUENCE: 74

ctaatacgac tcactatagg gcgagatctt gttgaagccg gcttcttctt ccttggcatg     60

cacgattaca cgaaatgctt ccattgcgac ggcggtctgt gtaattggga gacaggtgac    120

gacccctggg tagagcatgc ccgctggttc cctgaatgtc aattcgttca gctaagcaag    180

ggcggagcat tcatcgctga gtgccaacaa cgtcacgaaa aactagttaa tggcgcggta    240

gcccaggcag aacttcaggc ttttagtgaa gtagaaccgg gaggaacagg cagtgactca    300

aattcgccct atagtgagtc gtattag                                        327


<210> SEQ ID NO 75
<211> LENGTH: 311
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
```

<220> FEATURE:
<221> NAME/KEY: misc_feature
<222> LOCATION: (287)..(311)
<223> OTHER INFORMATION: Promoter

<400> SEQUENCE: 75
ctaatacgac tcactatagg gcgaagtcac tgcctgttcc tcccggttct acttcactaa 60
aagcctgaag ttctgcctgg gctaccgcgc cattaactag tttttcgtga cgttgttggc 120
actcagcgat gaatgctccg cccttgctta gctgaacgaa ttgacattca gggaaccagc 180
gggcatgctc tacccagggg tcgtcacctg tctcccaatt acacagaccg ccgtcgcaat 240
ggaagcattt cgtgtaatcg tgcatgccaa ggaagaagaa gccggcttcg ccctatagtg 300
agtcgtatta g 311

<210> SEQ ID NO 76
<211> LENGTH: 347
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (323)..(347)
<223> OTHER INFORMATION: Promoter

<400> SEQUENCE: 76
ctaatacgac tcactatagg gcgattccgc ttcatttgag aactgagctt gaagaaataa 60
tgcagtcgcc cgtcgtcaag ttctacctcg agaaaggtgt accgaaacaa gtgattcgaa 120
tgaccgtaaa aaatatatgc ttgacaacga gcgcggtttc cgtgatcttg acgaaattac 180
acacgtactc ggacaggtgc tcagcttcgg caacaagaag actgcgcctg ccaatgaaaa 240
aggtaggtgg ataccggata tttgtcggga attcaatgca gctgaacccg atgaggttga 300
ttcagaattg gcatacaata gaatcgccct atagtgagtc gtattag 347

<210> SEQ ID NO 77
<211> LENGTH: 332
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (308)..(332)
<223> OTHER INFORMATION: Promoter

<400> SEQUENCE: 77
ctaatacgac tcactatagg gcgattccgc ttcatttgag aactgagctt gaagaaataa 60
tgcagtcgcc cgtcgtcaag ttctacctcg agaaaggtgt accgaaacaa gtgattcgaa 120
tgaccgtaaa aaaatatatg cttgacaacg agcgcggttt ccgtgatctt gacgaaatta 180
cacacgtact cggacaggtg ctcagcttcg gcaacaagaa gactgcgcct gccaatgaaa 240
aaggtaggtg gataccggat atttgtcggg aattcaatgc agctgaaccc gatgaggttg 300
attcagaatc gccctatagt gagtcgtatt ag 332

<210> SEQ ID NO 78
<211> LENGTH: 331
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (307)..(331)
<223> OTHER INFORMATION: Promoter

<400> SEQUENCE: 78
ctaatacgac tcactatagg gcgattccgc ttcatttgag aactgagctt gaagaaataa 60
tgcagtcgcc cgtcgtcaag ttctacctcg agaaaggtgt accgaaacaa gtgattcgaa 120
tgaccgtgaa aaaatatatg cttgacaacg agcgcggttt ccgtgatctt gacgaaatta 180
cacacgtact cggacaggtg ctcagcttcg gcaacaagaa gactgcgcct gccaatgaaa 240
aaggtaggtg gataccggat atttgtcggg aattcaatgc agctgaaccc gatgaggttg 300
attcagatcg ccctatagtg agtcgtatta g 331

<210> SEQ ID NO 79
<211> LENGTH: 327
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (303)..(327)
<223> OTHER INFORMATION: Promoter

<400> SEQUENCE: 79
ctaatacgac tcactatagg gcgatggcta attaatagta ggccgaagaa ctttttgagt 60
ggcctcgata tgtccgacgt tgtggcttcg tgggaggttc ctttggttgg ccaagcttac 120
cgagtcgaat tcgaacacgg aagtgcaacg ggtaaacgtg ttgtgtacgt taatggactc 180
gaggtgttac gaaaacactg gctttttaag cttgttggcg aggaaagctt tgacatattg 240
ggacataagt gcatcatttc tatcaaagcc gtaggaggct tcaggttggt agcaaactcc 300
agttcgccct atagtgagtc gtattag 327

<210> SEQ ID NO 80
<211> LENGTH: 325
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (301)..(325)

<223> OTHER INFORMATION: Promoter

<400> SEQUENCE: 80
ctaatacgac tcactatagg gcgatggcta attaatagta ggccgaagaa ctttttgagt 60
ggcctcgata tgtccgacgt tgtggcttcg tgggaggttc ctttggttgg ccaagcttac 120
cgagtcgaat tcgaacacgg aagtgcaacg ggtaaacgtg ttgtgtacgt taatggactc 180
gaggtgttac gaaaacactg gctttttaag cttgttggcg aggaaagctt tgacatattg 240
ggacataagt gcatcatttc tatcaaagcc gtaggaggct tcaggttggt agcaaactcc 300
atcgccctat agtgagtcgt attag 325

<210> SEQ ID NO 81
<211> LENGTH: 325
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (301)..(325)
<223> OTHER INFORMATION: Promoter

<400> SEQUENCE: 81
ctaatacgac tcactatagg gcgatggagt ttgctaccaa cctgaagcct cctacggctt 60
tgatagaaat gatgcactta tgtcccaata tgtcaaagct ttcctcgcca acaagcttaa 120
aaagccagtg ttttcgtaac acctcgagtc cattaacgta cacaacacgt ttacccgttg 180
cacttccgtg ttcgaattcg actcggtaag cttggccaac caaaggaacc tcccacgaag 240
ccacaacgtc ggacatatcg aggccactca aaaagttctt cggcctacta ttaattagcc 300
atcgccctat agtgagtcgt attag 325

<210> SEQ ID NO 82
<211> LENGTH: 331
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (307)..(331)
<223> OTHER INFORMATION: Promoter

<400> SEQUENCE: 82
ctaatacgac tcactatagg gcgaggtctt gacaacacat gctaccctcg aacacgccga 60
ctgcgtcttc atgatggaca atgaggccat ctatcagatc tgccgtcgga accttggagt 120
cgagcgaccg gcgtaccaga atctcaaccg tctgatcagt caggccgttt cggcgattac 180
cgcttctcta cgtttctccg gagcgctgaa tgttgatctt aacgagttcc aaactaattt 240
agttccatac ccgcgaatcc attttcccct cgtcacttac gctccgatca tttctgctga 300
gaaggcttcg ccctatagtg agtcgtatta g 331

<210> SEQ ID NO 83
<211> LENGTH: 327
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (303)..(327)
<223> OTHER INFORMATION: Promoter

<400> SEQUENCE: 83
ctaatacgac tcactatagg gcgaggtctt gacaacacat gctaccctcg aacacgccga 60
ctgcgtcttc atgatggaca atgaggccat ctatcagatc tgccgtcgga accttggagt 120
cgagcgaccg gcgtaccaga atctcaaccg tctgatcagt caggccgttt cggcgattac 180
cgcttctcta cgtttctccg gagcgctgaa tgttgatctt aacgagttcc aaactaattt 240
agttccatac ccgcgaatcc attttccccc cgtcacttac gctccgatca tttctgctga 300
gaatcgccct atagtgagtc gtattag 327

<210> SEQ ID NO 84
<211> LENGTH: 325
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (301)..(325)
<223> OTHER INFORMATION: Promoter

<400> SEQUENCE: 84
ctaatacgac tcactatagg gcgactcagc agaaatgatc ggagcgtaag tgacgggggg 60
aaaatggatt cgcgggtatg gaactaaatt agtttggaac tcgttaagat caacattcag 120
cgctccggag aaacgtagag aagcggtaat cgccgaaacg gcctgactga tcagacggtt 180
gagattctgg tacgccggtc gctcgactcc aaggttccga cggcagatct gatagatggc 240
ctcattgtcc atcatgaaga cgcagtcggc gtgttcgagg gtagcatgtg ttgtcaagac 300
ctcgccctat agtgagtcgt attag 325

<210> SEQ ID NO 85
<211> LENGTH: 380
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (356)..(380)
<223> OTHER INFORMATION: Promoter

<400> SEQUENCE: 85

```
ctaatacgac tcactatagg gcgacaacgc tgtgcttcac gtagactcca cgttcgaaaa     60

tgtcgactgc acgtttatgg ttgataatca aacactcttc aagctttgtc gagaccggct    120

aaagattagg agtccatctt atgacaacgc aaatgctgtc atttcccagg gtttttcgtc    180

aatcatgaat tcggtggggc tggatggatc cttgaatgtg gacctcagcg agttccaaac    240

aaatctcgtc ccttttggaa gattacattt tacgatgatg agctacagtc cattcgttac    300

atccggacac cgcgatctaa gccgtgagac gtccgtcgtg gagattactc gtgacctcgc    360

cctatagtga gtcgtattag                                                380
```

```
<210> SEQ ID NO 86
<211> LENGTH: 378
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (354)..(378)
<223> OTHER INFORMATION: Promoter

<400> SEQUENCE: 86

ctaatacgac tcactatagg gcgacaacgc tgtgcttcac gtagactcca cgttcgaaaa     60

tgtcgactgc acgtttatgg ttgataatca aacactcctc aagctttgtc gagaccggct    120

aaaggttagg agtccatctt atgacaacgc aaatgctgtc atttcccagg gtttttcgtc    180

aatcatgaat tcggtggggc tggatggatc cttgaatgtg gacctcagcg agttccaaac    240

aagtctcgtc ccttttggaa gattacattt tacgatgatg agctacagtc cattcgttac    300

atccggacac cgcgatctaa gccgtgagac gtccgtcgtg gagattactc gtgatcgccc    360

tatagtgagt cgtattag                                                  378
```

```
<210> SEQ ID NO 87
<211> LENGTH: 377
<212> TYPE: DNA
<213> ORGANISM: Artificial sequence
<220> FEATURE:
<223> OTHER INFORMATION: A double stranded RNA expressing construct
      targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (353)..(377)
<223> OTHER INFORMATION: Promoter

<400> SEQUENCE: 87

ctaatacgac tcactatagg gcgaaacgct gtgcttcacg tagactccac gttcgaaaat     60

gtcgactgca cgtttatggt tgataatcaa acactcctca agctttgtcg agaccggcta    120

aaggttagga gtccatctta tgacaacgca aatgctgtca tttcccaggg tttttcgtga    180

atcatgaatt cggtggggct ggatggatcc ttgaatgtgg acctcagcga gttccaaaca    240

agtctcgtcc cttttggaag attacatttt acgatgatga gctacagtcc attcgttaca    300

tccggacacc gcgatctaag ccgtgagacg tccgtcgtgg agattactcg tgatcgccct    360
```

atagtgagtc gtattag 377

<210> SEQ ID NO 88
<211> LENGTH: 463
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (439)..(463)
<223> OTHER INFORMATION: Promoter

<400> SEQUENCE: 88
ctaatacgac tcactatagg gcgatatgga gaacatcgca caggacttcg gtaaaaagtg 60
ccgattgggc ttcgccatct acccggctcc gcaggtttcc actgccgttg tcgaaccata 120
caactcggtt ttgacgacac atgccaccct cgaacacgct gactgcgtat tcatgatgga 180
taatgaggcg atctatcaga tctgtcgtcg gaatcttgga gttgaacgac cggcgtatca 240
aaatctcaat cgactgatta gccaggccgt ttcggcgata accgcttctc tacgtttttc 300
cggagcgttg aatgttgacc tcaacgaatt tcagacgaat ctcgtcccct acccgcgaat 360
ccatttcccg ctcgtcactt atgctccgat tatttcggct gagaaggctc atcacgagca 420
acataacgta ctggaaatct cgccctatag tgagtcgtat tag 463

<210> SEQ ID NO 89
<211> LENGTH: 460
<212> TYPE: DNA
<213> ORGANISM: Artificial sequence
<220> FEATURE:
<223> OTHER INFORMATION: A double stranded RNA expressing construct
targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (436)..(460)
<223> OTHER INFORMATION: Promoter

<400> SEQUENCE: 89
ctaatacgac tcactatagg gcgaatggag aacatcgcac aggacttcgg taaaaagtgc 60
cgattgggct tcgccatcta cccggctccg caggtttcca ctgccgttgt cgaaccatac 120
aactcggttt tgacgacaca tgccaccctc gaacacgctg actgcgtatt catgatggat 180
aatgaggcga tctatcagat ctgtcgtcgg aatcttggag ttgaacgacc ggcgtatcaa 240
aatctcaatc gactgattag ccaggccgtt tcggcgataa ccgcttctct acgtttttcc 300
ggagcgttga atgttgacct caacgaattt cagacgaatc tcgtccccta cccgcgaatc 360
catttcccgc tcgtcactta tgctccgatt atttcggctg agaaggctca tcacgagcaa 420
cataacgtac tggaaatcgc cctatagtga gtcgtattag 460

<210> SEQ ID NO 90
<211> LENGTH: 459
<212> TYPE: DNA
<213> ORGANISM: Artificial sequence
<220> FEATURE:
<223> OTHER INFORMATION: A double stranded RNA expressing construct targeting a Varroa gene
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (435)..(459)
<223> OTHER INFORMATION: Promoter

<400> SEQUENCE: 90
ctaatacgac tcactatagg gcgaatggag aacatcgcac aggacttcgg taaaaagtgc 60
cgattgggct tcgccatcta cccggctccg caggtttcca ctgccgttgt cgaaccatac 120
aactcggttt tgacgacaca tgccaccctc gaacacgctg actgcgtatt catgatggat 180
aatgaggcga tctatcagat ctgtcgtcgg aatcttggag ttgaacgacc ggcgtatcaa 240
aatctcaatc gactgattag ccaggccgtt tcggcgataa ccgcttctct acgtttttcc 300
ggagcgttga atgttgacct caacgaattt cagacgaatc tcgtccccta cccgcgaatc 360
catttcccgc tcgtcactta tgctccgatt atttcggctg agaaggctca tcacgagcaa 420
cataacgtac tggaatcgcc ctatagtgag tcgtattag 459

<210> SEQ ID NO 91
<211> LENGTH: 480
<212> TYPE: DNA
<213> ORGANISM: Artificial sequence
<220> FEATURE:
<223> OTHER INFORMATION: A double stranded RNA expressing construct
targeting GFP
<220> FEATURE:
<221> NAME/KEY: misc_feature
<222> LOCATION: (1)..(24)
<223> OTHER INFORMATION: Promoter
<220> FEATURE:
<221> NAME/KEY: misc_feature
<222> LOCATION: (456)..(480)
<223> OTHER INFORMATION: Promoter

<400> SEQUENCE: 91
ctaatacgac tcactatagg gcgagccaac acttgtcact actttcggtt atggtgttca 60
atgctttgcg agatacccag atcatatgaa acagcatgac tttttcaaga gtgccatgcc 120
tgaaggttat gtacaggaaa gaactatatt tttcaaagat gacgggaact acaagacacg 180
tgctgaagtc aagtttgaag gtgataccct tgttaataga atcgagttaa aaggtattga 240
ttttaaagaa gatggaaaca ttcttggaca caaattggaa tacaactata actcacacaa 300
tgtatacatc atggcagaca aacaaaagaa tggaatcaaa gttaacttca aaattagaca 360
caacattgaa gatggaagcg ttcaactagc agaccattat caacaaaata ctccaattgg 420
cgatggccct gtccttttac cagacaacca ttaccttcgc cctatagtga gtcgtattag 480

<210> SEQ ID NO 92
<211> LENGTH: 478
<212> TYPE: DNA
<213> ORGANISM: Artificial sequence
<220> FEATURE:
<223> OTHER INFORMATION: A double stranded RNA expressing construct
targeting GFP

<400> SEQUENCE: 92
taatacgact cactataggg cgagccaaca cttgtcacta ctttcggtta tggtgttcaa 60
tgctttgcga gatacccaga tcatatgaaa cagcatgact ttttcaagag tgccatgcct 120
gaaggttatg tacaggaaag aactatattt ttcaaagatg acgggaacta caagacacgt 180
gctgaagtca agtttgaagg tgataccctt gttaatagaa tcgagttaaa aggtattgat 240
tttaaagaag atggaaacat tcttggacac aaattggaat acaactataa ctcacacaat 300
gtatacatca tggcagacaa acaaaagaat ggaatcaaag ttaacttcaa aattagacac 360
aacattgaag atggaagcgt tcaactagca gaccattatc aacaaaatac tccaattggc 420
gatggccctg tccttttacc agacaaccat taccttcgcc ctatagtgag tcgtatta 478

<210> SEQ ID NO 93
<211> LENGTH: 459
<212> TYPE: DNA
<213> ORGANISM: Artificial sequence
<220> FEATURE:
<223> OTHER INFORMATION: A double stranded RNA expressing construct targeting a Varroa gene

<400> SEQUENCE: 93
ctaatacgac tcactatagg gcgaatggag aacatcgcac aggacttcgg taaaaagtgc 60
cgattgggct tcgccatcta cccggctccg caggtttcca ctgccgttgt cgaaccatac 120
aactcggttt tgacgacaca tgccaccctc gaacacgctg actgcgtatt catgatggat 180
aatgaggcga tctatcagat ctgtcgtcgg aatcttggag ttgaacgacc ggcgtatcaa 240
aatctcaatc gactgattag ccaggccgtt tcggcgataa ccgcttctct acgtttttcc 300
ggagcgttga atgttgacct caacgaattt cagacgaatc tcgtccccta cccgcgaatc 360
catttcccgc tcgtcactta tgctccgatt atttcggctg agaaggctca tcacgagcaa 420
cataacgtac tggaatcgcc ctatagtgag tcgtattag 459

<210> SEQ ID NO 94
<211> LENGTH: 325
<212> TYPE: DNA
<213> ORGANISM: Artificial sequence
<220> FEATURE:
<223> OTHER INFORMATION: A double stranded RNA expressing construct targeting a Varroa gene

<400> SEQUENCE: 94
ctaatacgac tcactatagg gcgaggtctt gacaacacat gctaccctcg aacacgccga 60
ctgcgtcttc atgatggaca atgaggccat ctatcagatc tgccgtcgga accttggagt 120
cgagcgaccg gcgtaccaga atctcaaccg tctgatcagt caggccgttt cggcgattac 180
cgcttctcta cgtttctccg gagcgctgaa tgttgatctt aacgagttcc aaactaattt 240
agttccatac ccgcgaatcc attttcccct cgtcacttac gctccgatca tttctgctga 300
gtcgccctat agtgagtcgt attag 325

<210> SEQ ID NO 95
<211> LENGTH: 377
<212> TYPE: DNA
<213> ORGANISM: Artificial sequence
<220> FEATURE:
<223> OTHER INFORMATION: A double stranded RNA expressing construct targeting a Varroa gene

<400> SEQUENCE: 95
ctaatacgac tcactatagg gcgaaacgct gtgcttcacg tagactccac gttcgaaaat 60
gtcgactgca cgtttatggt tgataatcaa acactcttca agctttgtcg agaccggcta 120
aagattagga gtccatctta tgacaacgca aatgctgtca tttcccaggg tttttcgtca 180
atcatgaatt cggtggggct ggatggatcc ttgaatgtgg acctcagcga gttccaaaca 240
aatctcgtcc cttttggaag attacatttt acgatgatga gctacagtcc attcgttaca 300
tccggacacc gcgatctaag ccgtgagacg tccgtcgtgg agattactcg tgatcgccct 360
atagtgagtc gtattag 377

<210> SEQ ID NO 96
<211> LENGTH: 428
<212> TYPE: DNA
<213> ORGANISM: Artificial sequence
<220> FEATURE:
<223> OTHER INFORMATION: A double stranded RNA expressing construct targeting a Varroa gene

<400> SEQUENCE: 96
ctaatacgac tcactatagg gcgatcagat gattggaacg gaggaaaatg tccaagtagc 60
attcgtgggc tcgattgtcg agtgtcacaa gctcaaggtg tttactcagg aagaagcact 120
gagattcctt gcggcaaaga tgaagcagcg gatgtttgga ccacagaaag cggaagaccc 180
cttgacaagg catgggaagc cgtactttca tccgtagtca accatattcc cgttcaatcg 240
cctgactaca atatgactgt ccgggcacac tatcttgcac taatggtgcg tcgcatcatt 300
caggcgcgtt atgatcgccg cttcattgac gatcgcgact attacggcaa caaacgaatt 360
gagcttccgg gttcgatgat atcgctgctg tttgaagacc tgtttcgccc tatagtgagt 420
cgtattag 428

<210> SEQ ID NO 97
<211> LENGTH: 474
<212> TYPE: DNA
<213> ORGANISM: Artificial sequence
<220> FEATURE:
<223> OTHER INFORMATION: A double stranded RNA expressing construct targeting a Varroa gene

<400> SEQUENCE: 97
ctaatacgac tcactatagg gcgatcaatt cgtctgcaga tctcaccgat tttctgatat 60
cgctgggagt ccaggatatt cgactactat gcggagctga attcagcaaa acacacgtct 120
actatgtatt ccacaacggt gttattaaag gcgtcgttga ggatcatcgc aggcttatca 180
acgagattcg gcaatttcgt cggaagggat acttgtcgcc ttacttatca gtttatccaa 240
atcatctaca tcgctgtgtg tatattgtaa ctgacggtgg tcgtttctgc aggccgttta 300
tcattgttga ggatggtcag ccaaaagtta cgcagaaaca tttggacgac ctcaaagcca 360
atatatataa cttccaagac ttcctggaca tgggctttgt agagtttctc gatgtaaatg 420
aggaaaacga cgcgcttatc gccatttatg tcgccctata gtgagtcgta ttag 474

<210> SEQ ID NO 98
<211> LENGTH: 414
<212> TYPE: DNA
<213> ORGANISM: Artificial sequence
<220> FEATURE:
<223> OTHER INFORMATION: A double stranded RNA expressing construct targeting a Varroa gene

<400> SEQUENCE: 98
ctaatacgac tcactatagg gcgaaatgag tgttgagcgc ggatttaagg ccggtgtagt 60
atataaaaca gaaacgatca atttgcgtaa gttatctggg gatgtgggag tccagacatc 120
gtgcgttttt ggtcgaaagg caggagattc tgagttacag aaatttgtag atgttgatgg 180
cctgccatac atcggcagca gggtagtaca gggagatccg gtatgtgcat atataaattt 240
gaccacggga caactgaaga ctgtaaggta ttactcgacc gagccagcaa tcgtgcatga 300
agtgaaaatt cttggtaatg attccggtac agacaccctc caacaaatcc agttgacgta 360
tcttattgat cgaacgccaa atgatcggag tcgccctata gtgagtcgta ttag 414

<210> SEQ ID NO 99
<211> LENGTH: 372
<212> TYPE: DNA
<213> ORGANISM: Artificial sequence
<220> FEATURE:
<223> OTHER INFORMATION: A double stranded RNA expressing construct targeting a Varroa gene

<400> SEQUENCE: 99
ctaatacgac tcactatagg gcgaaggtga catccgtgtt cgccgtgtac ggcatcaaag 60
tggatccaag acatctaagt ctggtagggg actacatgac tttcgacgga gcttaccgcg 120
ccttcaacag aatccacatg gcaaacaatg catcgccact ccagcagatg agctttgaaa 180
cgacgtgcac atttatgaaa aacgctgctt tatttggtac gaaatcccct aagacagata 240
cgaagacaat ctttgccatg ctaatagtgt ttctgttttt agtgcctggt acgatcatta 300
attacggcgt tgaaagtaac tccaaacagc gaccctatat gtcttcattc gccctatagt 360
gagtcgtatt ag 372

<210> SEQ ID NO 100
<211> LENGTH: 359
<212> TYPE: DNA
<213> ORGANISM: Artificial sequence
<220> FEATURE:
<223> OTHER INFORMATION: A double stranded RNA expressing construct targeting a Varroa gene

<400> SEQUENCE: 100
ctaatacgac tcactatagg gcgactgtac agggtccgaa tataaaactt catacattca 60
aaatcacgta tcaggattat gctaaacatc gcaccataaa aatcttcact aaagttattt 120
tacgcttcag gatagtggtc cgttatgagt gttgcggtat tagtgcgttt acaaatttgc 180
taacgatatt aacaagctta tttcactcgt tggcaggttt tctagaacgc gaggtgagga 240
aggataacct tccgatgatg tcattcggcg acaatcctga ggcgcctcag cctcgggaga 300
tgattgatct agaagcaacc tttgagaaac tcgaatcgcc ctatagtgag tcgtattag 359

<210> SEQ ID NO 101
<211> LENGTH: 249
<212> TYPE: DNA
<213> ORGANISM: Artificial sequence
<220> FEATURE:
<223> OTHER INFORMATION: A double stranded RNA expressing construct targeting a Varroa gene

<400> SEQUENCE: 101
ctaatacgac tcactatagg gcgacaattg aatatggacg tcactcagaa gtgtcttatt 60
gccgaatgct ggattcctga tcgcgatgta gcaaaggtac aagctgccct gcgacgtgga 120
acggaagcgg ctggaagcag cttcccgtgt atcattaacc ggttggaaac ggaccaagct 180
ccaccgacgt tctacagaac gaactcgttt actgctggct ttcaatcgcc ctatagtgag 240
tcgtattag 249

<210> SEQ ID NO 102
<211> LENGTH: 338

-continued

<212> TYPE: DNA
<213> ORGANISM: Artificial sequence
<220> FEATURE:
<223> OTHER INFORMATION: A double stranded RNA expressing construct
targeting a Varroa gene

<400> SEQUENCE: 102
ctaatacgac tcactatagg gcgacatcat cttcttcatc tgcttggcgg cattctggac 60
ggttatgctg gtcatcttct atcagacact cgatgccttc cagccaaagt ggaccctgga 120
cgctagtctc attggcactg taccgggatt aggcttcagg ccacgcccac cgctgtctaa 180
catcgactca acactcatct atttcaaggt atctaagccg ttagtgtata tgttatatta 240
tagcgctctt tgttatgtgg aaagacgcca gggcgcgtat ctatatggtg gttttcatac 300
caaccgtggg aacctcgccc tatagtgagt cgtattag 338

<210> SEQ ID NO 103
<211> LENGTH: 311
<212> TYPE: DNA
<213> ORGANISM: Artificial sequence
<220> FEATURE:
<223> OTHER INFORMATION: A double stranded RNA expressing construct
targeting a Varroa gene

<400> SEQUENCE: 103
ctaatacgac tcactatagg gcgaaatggt ttctgctacc tgtgaggata gtatgcggga 60
tgcttgtatt cgttttcttg cctcgaaagt caatctcaaa gcgcttgaca gtgagacaga 120
gcttatgctc attgaagagg ccggcaaagt ggcagccctc gtcggtggag aggagtttgt 180
gctgctggtt aagctcctca attcattaaa ggtagattgt acattttggc gtcttctcga 240
acaagttaga atctatttag caaagtgcca atgtatcagc ttccaattcg ccctatagtg 300
agtcgtatta g 311

<210> SEQ ID NO 104
<211> LENGTH: 325
<212> TYPE: DNA
<213> ORGANISM: Artificial sequence
<220> FEATURE:
<223> OTHER INFORMATION: A double stranded RNA expressing construct
targeting a Varroa gene

<400> SEQUENCE: 104
ctaatacgac tcactatagg gcgatggcta attaatagta ggccgaagaa ctttttgagt 60
ggcctcgata tgtccgacgt tgtggcttcg tgggaggttc ctttggttgg ccaagcttac 120
cgagtcgaat tcgaacacgg aagtgcaacg ggtaaacgtg ttgtgtacgt taatggactc 180
gaggtgttac gaaaacactg gctttttaag cttgttggcg aggaaagctt tgacatattg 240
ggacataagt gcatcatttc tatcaaagcc gtaggaggct tcaggttggt agcaaactcc 300
atcgccctat agtgagtcgt attag 325

<210> SEQ ID NO 105
<211> LENGTH: 311
<212> TYPE: DNA
<213> ORGANISM: Artificial sequence
<220> FEATURE:
<223> OTHER INFORMATION: A double stranded RNA expressing construct
targeting a Varroa gene

<400> SEQUENCE: 105
ctaatacgac tcactatagg gcgaagccgg cttcttcttc cttggcatgc acgattacac 60

-continued gaaatgcttc cattgcgacg gcggtctgtg taattgggag acaggtgacg acccctgggt 120
agagcatgcc cgctggttcc ctgaatgtca attcgttcag ctaagcaagg gcggagcatt 180
catcgctgag tgccaacaac gtcacgaaaa actagttaat ggcgcggtag cccaggcaga 240
acttcaggct tttagtgaag tagaaccggg aggaacaggc agtgacttcg ccctatagtg 300
agtcgtatta g 311

<210> SEQ ID NO 106
<211> LENGTH: 330
<212> TYPE: DNA
<213> ORGANISM: Artificial sequence
<220> FEATURE:
<223> OTHER INFORMATION: A double stranded RNA expressing construct targeting a Varroa gene

<400> SEQUENCE: 106
ctaatacgac tcactatagg gcgattccgc ttcatttgag aactgagctt gaagaaataa 60
tgcagtcgcc cgtcgtcaag ttctacctcg agaaaggtgt accgaaacaa gtgattcgaa 120
tgaccgtaaa aaatatatgc ttgacaacga gcgcggtttc cgtgatcttg acgaaattac 180
acacgtactc ggacaggtgc tcagcttcgg caacaagaag actgcgcctg ccaatgaaaa 240
aggtaggtgg ataccggata tttgtcggga attcaatgca gctgaacccg atgaggttga 300
ttcagatcgc cctatagtga gtcgtattag 330

<210> SEQ ID NO 107
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 107
ctaatacgac tcactatagg gcgaatggag aacatcgcac ag 42

<210> SEQ ID NO 108
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 108
ctaatacgac tcactatagg gcgattccag tacgttatgt tgctc 45

<210> SEQ ID NO 109
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 109
ctaatacgac tcactatagg gcgaggtctt gacaacacat gctac 45

<210> SEQ ID NO 110
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 110
ctaatacgac tcactatagg gcgactcagc agaaatgatc gg 42

<210> SEQ ID NO 111
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 111
ctaatacgac tcactatagg gcgaaacgct gtgcttcacg ta 42

<210> SEQ ID NO 112
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 112
ctaatacgac tcactatagg gcgatcacga gtaatctcca cga 43

<210> SEQ ID NO 113
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 113
ctaatacgac tcactatagg gcgatcagat gattggaacg ga 42

<210> SEQ ID NO 114
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 114
ctaatacgac tcactatagg gcgaaacagg tcttcaaaca gcag 44

<210> SEQ ID NO 115
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 115
ctaatacgac tcactatagg gcgatcaatt cgtctgcaga tctc 44

<210> SEQ ID NO 116
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 116
ctaatacgac tcactatagg gcgacataaa tggcgataag cg 42

<210> SEQ ID NO 117
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 117
ctaatacgac tcactatagg gcgaaatgag tgttgagcgc gg 42

<210> SEQ ID NO 118
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 118
ctaatacgac tcactatagg gcgactccga tcatttggcg tt 42

<210> SEQ ID NO 119
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 119
ctaatacgac tcactatagg gcgaaggtga catccgtgtt cg 42

<210> SEQ ID NO 120
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 120
ctaatacgac tcactatagg gcgaatgaag acatataggg tcgct 45

<210> SEQ ID NO 121
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 121
ctaatacgac tcactatagg gcgactgtac agggtccgaa tataaa 46

<210> SEQ ID NO 122
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 122
ctaatacgac tcactatagg gcgattcgag tttctcaaag gttg 44

<210> SEQ ID NO 123
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 123
ctaatacgac tcactatagg gcgacaattg aatatggacg tcactc 46

-continued

<210> SEQ ID NO 124
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 124
ctaatacgac tcactatagg gcgattgaaa gccagcagta aacg 44

<210> SEQ ID NO 125
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 125
ctaatacgac tcactatagg gcgacatcat cttcttcatc tgcttg 46

<210> SEQ ID NO 126
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 126
ctaatacgac tcactatagg gcgaggttcc cacggttggt at 42

<210> SEQ ID NO 127
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 127
ctaatacgac tcactatagg gcgaaatggt ttctgctacc tgtg 44

<210> SEQ ID NO 128
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 128
ctaatacgac tcactatagg gcgaattgga agctgataca ttgg 44

<210> SEQ ID NO 129
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 129
ctaatacgac tcactatagg gcgatggcta attaatagta ggccg 45

<210> SEQ ID NO 130
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 130
ctaatacgac tcactatagg gcgatggagt ttgctaccaa cct 43

<210> SEQ ID NO 131
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 131
ctaatacgac tcactatagg gcgaagccgg cttcttcttc ct 42

<210> SEQ ID NO 132
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 132
ctaatacgac tcactatagg gcgaagtcac tgcctgttcc tcc 43

<210> SEQ ID NO 133
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 133
ctaatacgac tcactatagg gcgattccgc ttcatttgag aac 43

<210> SEQ ID NO 134
<211> LENGTH: 43
<212> TYPE: DNA
<213> ORGANISM: Artificial sequence
<220> FEATURE:
<223> OTHER INFORMATION: Single strand DNA oligonucleotide

<400> SEQUENCE: 134
ctaatacgac tcactatagg gcgatctgaa tcaacctcat cgg 43

<210> SEQ ID NO 135
<211> LENGTH: 52
<212> TYPE: DNA
<213> ORGANISM: Artificial sequence
<220> FEATURE:
<223> OTHER INFORMATION: Single strand DNA oligonucleotide

<400> SEQUENCE: 135
taatacgact cactataggg cgagccaaca cttgtcacta ctagaaagag aa 52

<210> SEQ ID NO 136
<211> LENGTH: 48
<212> TYPE: DNA
<213> ORGANISM: Artificial sequence
<220> FEATURE:
<223> OTHER INFORMATION: Single strand DNA oligonucleotide

<400> SEQUENCE: 136
taatacgact cactataggg cgaaggtaat ggttgtctgg taaaggac 48

<210> SEQ ID NO 137

-continued

<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 137
aaagggcagg tgcttatcaa 20

<210> SEQ ID NO 138
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 138
tgtccagggt cgagagtagc 20

<210> SEQ ID NO 139
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 139
acctttttca aagaccgaac c 21

<210> SEQ ID NO 140
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 140
cgaagactcc gttcgaaaac 20

<210> SEQ ID NO 141
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 141
ctagttaatg gcgcggtagc 20

<210> SEQ ID NO 142
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 142
tcctcccggt tctacttcac 20

<210> SEQ ID NO 143
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 143

-continued

```
aatgccatca ttaccatcct g                                          21


<210> SEQ ID NO 144
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 144

caaaaaccaa tcggcaatct                                            20


<210> SEQ ID NO 145
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 145

atctgcccac gtcagcgttt                                            20


<210> SEQ ID NO 146
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 146

gtccgtcatt tcggctttgg                                            20


<210> SEQ ID NO 147
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 147

aagtcgtacg agcttcccga c                                          21


<210> SEQ ID NO 148
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 148

acagggaggc aaggatggaa c                                          21
```